US008067243B2

United States Patent
Erfurth et al.

(10) Patent No.: US 8,067,243 B2
(45) Date of Patent: Nov. 29, 2011

(54) METHODS AND SYSTEMS FOR ANALYZING MEDICATION LEVELS IN A SAMPLE

(75) Inventors: Stephen C. Erfurth, Eugene, OR (US); Grant D. Beardsley, Eugene, OR (US)

(73) Assignee: Oregon Medical Laboratories, Springfield, OR (US)

( * ) Notice: Subject to any disclaimer, the term of this patent is extended or adjusted under 35 U.S.C. 154(b) by 227 days.

(21) Appl. No.: 12/552,596

(22) Filed: Sep. 2, 2009

(65) Prior Publication Data

US 2010/0051801 A1   Mar. 4, 2010

Related U.S. Application Data

(60) Provisional application No. 61/093,888, filed on Sep. 3, 2008.

(51) Int. Cl.
G01N 33/00 (2006.01)
B01D 59/44 (2006.01)
B01D 59/00 (2006.01)

(52) U.S. Cl. .................. 436/161; 250/282; 250/281

(58) Field of Classification Search ............ 436/161; 250/282, 281
See application file for complete search history.

(56) References Cited

U.S. PATENT DOCUMENTS 5,776,783 A * 7/1998 Kell ......................... 436/111
6,940,065 B2   9/2005 Graber et al.
2005/0233459 A1 * 10/2005 Melker et al. ............. 436/56

OTHER PUBLICATIONS

Coles et al., Simultaneous Determination of Codeine, Morphine, Hydrocodone, Hydromorphone, Oxycodone, and 6-Acetylmorphine in Urine, Serum, Plasma, Whole Blood, and Meconium by LC-MS-MS; Journal of Analytical Toxicology, vol. 31, Jan./Feb. 2007.

* cited by examiner

Primary Examiner — Christine T Mui
(74) Attorney, Agent, or Firm — Myers Bigel Sibley & Sajovec

(57) ABSTRACT

Methods and systems for assessing patient compliance with opioid drug therapy are provided. A liquid chromatography tandem mass spectrometer (LC/MS/MS) can be used to simultaneously detect a set of measurements including an amount of at least ten opioids (and their metabolites) in a body fluids sample from a patient. The set of at least ten opioids can include at least oxymorphone and fentanyl. The amounts of opioids and their metabolites are analyzed. For example, the ratios of opioids and their respective metabolites can be used to determine which opioids a patient has been administered. A report of patient compliance is generated based on the set of measurements.

39 Claims, 38 Drawing Sheets

SUMMARY OF OPIATE/OPIOID METABOLISM

MAJOR METABOLISM
• CODEINE → MORPHINE
• HYDROCODONE → HYDROMORPHONE (DILAUDID)
• OXYCODONE (PERCOCET, OXYCOTIN) →
  OXYMORPHONE (OPANA)
• FENTANYL (DURAGESIC) → NORFENTANYL
• HEROIN → 6-MONOACETYLMORPHINE → MORPHINE

MINOR METABOLISM
• HIGH DOSE CODEINE → HYDROCODONE (VICODIN)
• HIGH DOSE MORPHINE → HYDROMORPHONE (DILAUDID)

JOHN SMITH, MD  PT: ▓▓▓▓▓  ACC# ▓▓▓▓▓
PAIN CARE NW  DOB: ▓▓▓▓▓  ID: ▓▓▓▓▓
12345 PARK AVENUE  GENDER: FEMALE  CTRL ▓▓▓▓▓
HERE, OR 97666  COL: 06/05/08 14:00  REP: 06/07/08 15:00

* PAIN MANAGEMENT PANEL, URINE *
ADDITIONAL INFORMATION:         NOBLE CUP
PRESCRIBED PAIN MEDICATIONS:    HYDROCODONE

| DRUG CLASS | RESULT | INTERPRETATIVE COMMENT |
|---|---|---|
| HYDROCODONE | POSITIVE | CONSISTENT WITH HYDROCODONE PRESCRIPTION |
| OXYCODONE | POSITIVE | DISCREPANT RESULTS; OXYCODONE SHOULD BE NEGATIVE. |

OPIOID PANEL-URINE (LC/MS/MS)

|  | RESULT | CONCENTRATION | THRESHOLD |
|---|---|---|---|
| →HYDROCODONE* | POSITIVE | 40 ng/mL | 5 ng/mL |
| HYDROMORPHONE | NEGATIVE |  | 5 ng/mL |
| →OXYCODONE* | POSITIVE | 70 ng/mL | 5 ng/mL |
| OXYMORPHONE* | NEGATIVE |  | 5 ng/mL |
| CODEINE* | NEGATIVE |  | 5 ng/mL |
| MORPHINE* | NEGATIVE |  | 5 ng/mL |
| 6-MONOACETYLMORPHINE | NEGATIVE |  | 5 ng/mL |
| MEPERIDINE | NEGATIVE |  | 5 ng/mL |
| FENTANYL | NEGATIVE |  | 2 ng/mL |
| NORFENTANYL | NEGATIVE |  | 2 ng/mL |

*DENOTES LABORATORY DETECTION OF NON-CONJUGATE ("FREE") DRUG

DRUGS OF ABUSE, URINE – 9 DRUGS

|  | RESULT | SCREENING THRESHOLD |
|---|---|---|
| AMPHETAMINES SCREEN | NEGATIVE | 300 ng/mL |
| BARBITURATES SCREEN | NEGATIVE | 200 ng/mL |
| →BENZODIAZEPINES SCREEN | POSITIVE | 200 ng/mL |
| COCAINE METABOLITE SCREEN | NEGATIVE | 300 ng/mL |
| PHENCYCLIDINE SCREEN | NEGATIVE | 25 ng/mL |
| MARIJUANA METAB. SCREEN | NEGATIVE | 20 ng/mL |
| METHADONE METAB. SCREEN | NEGATIVE | 300 ng/mL |
| PROPOXYPHENE SCREEN | NEGATIVE | 300 ng/mL |
| ETHANOL SCREEN | NEGATIVE | 0.02 g/dL |
| SPECIMEN VALIDITY TESTING | PASSED |  |
| SPECIMEN TEMPERATURE | WITHIN ACCEPTABLE RANGE |  |

FIG. 4A

| BARCODE | | | | XXXXXXXX | |
|---|---|---|---|---|---|
| XXXXXXXX | | | | | |

| PATIENT | LAST NAME | FIRST | MI | BILL TO: ☐ INSURANCE ☐ MEDICARE/MEDICAID ☐ PATIENT ☐ CLIENT/OFFICE | |
|---|---|---|---|---|---|
| | SEX | DOB | SSN | | |
| | PATIENT PHONE | CHART#/PID# | ☐ GENETIC OPT OUT | | |
| RESPONSIBLE PARTY | LAST NAME | FIRST | MI | LAB USE ONLY | |
| | MAILING ADDRESS | CITY | STATE | ZIP | 103 113 ☐ 95730 |
| | | | | | 104 115     VENIPUNCTURE |
| | INSURANCE CO | | | | 106 119 ☐ 95170 |
| | | | | | 107 120     HEEL/ |
| | MAILING ADDRESS | CITY | STATE | ZIP | 109 123     FINGER STICK |
| | | | | | 111 124 ☐ 95250 |
| | ID NO. | | GROUP NO. | | 112 126     HANDLING |

| SPECIMEN | SEND DUPLICATE REPORT TO: NAME & ADDRESS |
|---|---|
| | DATE AND TIME COLLECTED |
| | TEMPERATURE     ☐ WITHIN RANGE |
| | RANGE 90°-100°F  ☐ NOT WITHIN RANGE |

| BARCODE XXXXXXXX | BARCODE XXXXXXXX |
|---|---|
| FULL NAME | FULL NAME |
| BARCODE XXXXXXXX | BARCODE XXXXXXXX |
| FULL NAME | FULL NAME |

REPORT COMMENTS _____

| TEST ORDERED | |
|---|---|
| ▮▮▮▮▮ ◯ 36286 | PAIN MANAGEMENT PANEL (COMPONENTS LISTED BELOW) 6-MONOACETYLMORPHINE, AMPHETAMINES, BARBITURATES, BENZODIAZEPINES, COCAINE, CODEINE, ETHANOL, FENTANYL, HYDROCODONE, HYDROMORPHONE, MARIJUANA, MEPERIDINE, METHADONE, MORPHINE, NORFENTANYL, OXYCODONE, OXYMORPHONE, PHENCYCLIDINE, PROPOXYPHENE, SPECIMEN VALIDITY TESTING. |

| CIRCLE THE MEDICATIONS TAKEN IN THE LAST THREE DAYS | | | |
|---|---|---|---|
| YES CODEINE (TYLENOL 3, TYLENOL 4) | ▮▮▮▮ | YES METHADONE (DOLOPHINE, METHADOSE) | ▮▮▮▮ |
| YES BENZODIAZEPINE (VALIUM, RESTORIL, TEMAZEPAM, LIBRIUM, XANAX, DALMANE, CLONAPIN) | ▮▮▮▮ | YES MORPHINE (AVINZA, KADIAN, MS, CONTIN, MSIR ROXANOL) | ▮▮▮▮ |
| | | YES OXYCODONE (OXYCONTIN, PERCOCET, PERCODAN, ROXICODONE, TYLOX) | ▮▮▮▮ |
| YES FENTANYL (ACTIQ, DURAGESIC, FENTORA) | ▮▮▮▮ | YES OXYMORHONE (OPANA, OPANA ER, NUMORPHAN) | ▮▮▮▮ |
| YES HYDROCODONE (LORCET, LORTAB, NORCO, VICODIN) | ▮▮▮▮ | YES PORPOXYPHENE (DARVOCET, DARVON) | ▮▮▮▮ |
| YES HYDROMORPHONE (DILAUDID, HYDROSTAT IR) | ▮▮▮▮ | YES NO DRUGS PRESCRIBED | ▮▮▮▮ |
| YES MEPERIDINE (DEMEROL) | ▮▮▮▮ | YES UNKNOWN OR NOT PROVIDED | ▮▮▮▮ |

*FIG. 4B*

METHODS AND SYSTEMS FOR ANALYZING MEDICATION LEVELS IN A SAMPLE

RELATED APPLICATIONS

This application claims priority to Application Ser. No. 61/093,888 filed Sep. 3, 2008, the disclosure of which is incorporated by reference in its entirety.

FIELD OF THE INVENTION

The present invention relates to methods and systems for analyzing medication levels in a sample. In particular, the invention relates to methods and systems for analyzing opioid/opiate in a body fluids sample.

BACKGROUND

Promoting pain relief and preventing the abuse of pain medications can be difficult for health professionals to balance. Patients who use drugs of abuse are more likely to abuse pain medications and more likely to divert medication either for financial gain or to fund an addition to legal or illegal drugs. Patients who use drugs of abuse are also at higher risk of combining such use with the legal drugs that are prescribed to them, which puts them at risk for overdoses and accidents. Patients who take legally prescribed controlled medications may also be knowingly or unknowingly combining prescriptions from multiple prescribers, which can put them at risk for overdoses and accidents. The ingestion of multiple opioid/opiates can result in respiratory depression and/or fatal respiratory failure. Moreover, death rates from prescription opioid/opiate use are increasing, and the abuse of prescription opioid/opiate use is also increasing.

However, the interpretation of pain management opioid/opiate toxicology test data is complex. Physicians may lack the time and/or expertise to interpret pain management opioid/opiate toxicology data. In addition, opioid/opiate drug metabolism is complex, and some opioid/opiate drug metabolites are also available as prescription drugs, which makes the source of the opioid/opiate drug difficult to determine.

SUMMARY OF EMBODIMENTS OF THE INVENTION

Embodiments according to the present invention include methods and systems for assessing patient compliance with opioid drug therapy. A liquid chromatography tandem mass spectrometer (LC/MS/MS) can be used to simultaneously detect a set of measurements including an amount of at least ten opioids (and their metabolites) in a body fluids sample from a patient. The set of at least ten opioids can include at least oxymorphone and fentanyl. The amounts of opioids and their metabolites can be analyzed, and/or the ratios of opioids and their respective metabolites can be used to determine which opioids a patient has ingested. A report of patient compliance can be generated based on the set of measurements.

In some embodiments, the at least ten opioids that are simultaneously detected include the following: hydrocodone, hydromorphone, oxycodone, oxymorphone, codeine, morphine, 6-monoacetylmorphine, meperidine, fentanyl and/or nor-fentanyl. In particular embodiments, the detection threshold can be as low as 2-5 ng/mL. In addition, drugs of abuse can also be detected, such as alcohol, amphetamines, barbiturates, benzodiazepines, cocaine, marijuana, methadone, phencyclidine and/or propoxyphene.

In some embodiments, the report of patient compliance can be generated using data related to prescription information. The report can identify a set of discrepant and consistent results for the clinician. Accordingly, patient compliance with prescribed opioids can be assessed and/or additional prescription medications or other substances (e.g., drugs of abuse) can be detected and identified to the prescriber.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 4A is a sample patient compliance report according to some embodiments of the present invention.

FIG. 4B is a sample test requisition template for indicating prescription information according to some embodiments of the present invention.

DETAILED DESCRIPTION OF EMBODIMENTS OF THE INVENTION

Figure 1:
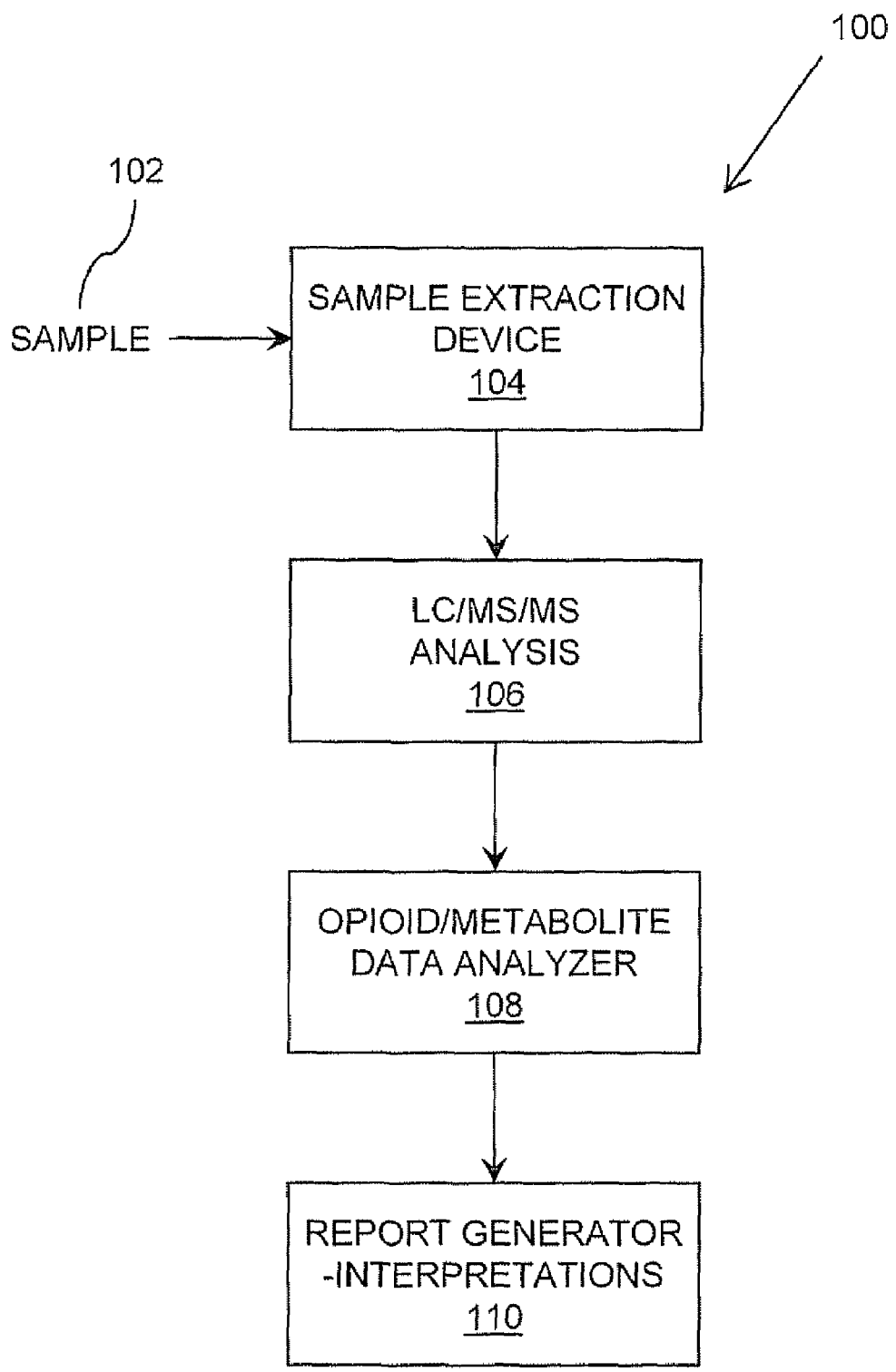
FIG. 1 is a block diagram of systems and methods according to some embodiments of the present invention.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable storage medium having computer-usable or computer-readable program code embodied in the medium for use by or in connection with an instruction execution system.

Embodiments according to the present invention include methods and systems for assessing patient compliance with opioid drug therapy. As shown in FIG. 1, a system 100 for assessing patient compliance includes a sample extraction device 104 and a liquid chromatography tandem mass spectrometer (LC/MS/MS) 106. The sample extraction device 104 can be a Hamilton MICROLAB® Starlet automated extraction device and can be configured to prepare or partially purify a sample for the LC/MS/MS 106. The LC/MS/MS 106 can be used to simultaneously detect a set of measurements including an amount of at least ten opioids (and their metabolites) in a body fluids sample 102 from a patient. The set of at least ten opioids can include at least oxymorphone and fentanyl. The amounts of opioids and their metabolites are analyzed by an opioid/metabolite analyzer 108. For example, the ratios of opioids and their respective metabolites can be used to determine which opioids a patient has taken or administered. A report generator 110 generates a report of patient compliance based on the set of measurements.

In some embodiments, the at least ten opioids that are simultaneously detected include the following: hydrocodone, hydromorphone, oxycodone, oxymorphone, codeine, morphine, 6-monoacetylmorphine, meperidine, fentanyl and/or nor-fentanyl. In particular embodiments, additional drugs (e.g., drugs of abuse) can be detected, such as alcohol, amphetamines, barbiturates, benzodiazepines, cocaine, marijuana, methadone, phencyclidine and/or propoxyphene. In some embodiments, drugs of abuse can be detected using immunoassays for a screen. If the screen is positive, it is confirmed using gas chromatography mass spectrometry.

The report of patient compliance can be generated based on the ratios of the concentrations of the opioid drugs and their metabolites to determine the opioid drug taken by or administered to the patient. In some embodiments, a set of discrepant and/or consistent results for a plurality of opioid drugs is determined by comparing the set of measurements with data relating to prescription information for the patient. The discrepant and consistent results can indicate whether a patient is taking opioid drugs being prescribed or taking additional drugs. As used herein, the terms "consistent" refers to a report result that is consistent with a probable opioid source, a safety standard and/or an expected result, such as an expected result based on patient prescription information. The terms "non-consistent" or "discrepant" refer to a report result that is not consistent with a probable opiod source, a safety standard and/or an expected result.

Although embodiments according to the present invention are described herein with respect to assessing patient compliance, for example, with a prescription, it should be understood that reports of probable opioid source(s) can be generated according to some embodiments for subjects for which prescription information is not provided or is unknown, including forensic sample tests or screening tests for patient safety before an opioid prescription is provided. An opioid source is an originally administered or ingested compound that manifests itself as a detected amount of opioid or opioid metabolite.

In some embodiments, the LC-MS-MS can detect threshold cutoff amounts of opioids or opioid metabolites below 10 ng/ml and as low as 2-5 ng/ml. For example, in some embodiments, oxymorphone, morphine, hydrocodone, hydromorphone, oxycodone, oxymorphone, codeine, morphine, 6-monoacetylmorphine and meperidine are detected to threshold cutoff amounts of 5 ng/ml, and fentanyl and nor-fentanyl are detected to threshold cutoff amounts of 2 ng/ml. By detecting opioid levels as low as 2-5 ng/ml, the occurrences of false negatives can be reduced, the time during which the test reliably detects a positive result can be increased, and the "fast metabolizers" of certain opioids can be detected.

LC/MS/MS is described, for example, in Coles et al. Journal of Analytical Toxicology, Vol. 31, January/February 2007 and U.S. Pat. No. 6,940,065 to Graber et al., the disclosures of which are hereby incorporated by reference in their entireties. LC/MS/MS can allow for testing for the free (non-conjugated) drug, which can avoid a hydrolysis step typically required for sample preparation in less sensitive methods, e.g., gas chromagraphy—mass spectrometry. In addition, 6-monoacetylmorphine, a metabolite of heroin, can be isolated with LC/MS/MS, which is definitive proof of heroin use. Hydrolysis will hydrolyze 6-monoacetylmorphine, which will prevent detection of this heroin metabolite.

In some embodiments, when a clinician receives a result that indicates the patient is taking a medication that was not prescribed, the patient is questioned about the source of the medication. In some cases, this may result in the patient's removal from the practice.

The interpretation of opiate/opioid results can be difficult because several commonly prescribed opiates (codeine) and opioids (hydrocodone and oxycodone) metabolize to active opiate/opioid drugs (codeine→morphine; hydrocodone→hydromorphone; and oxycodone→oxymorphone) which are also available by prescription.

In addition to the major metabolism that occurs in standard doses of opiate/opioids, when high doses of codeine or morphine are used in tolerant patients, alternative metabolism can occur to commonly prescribed opioids (codeine→hydrocodone; and morphine→hydromorphone).

Figures 2, 3:
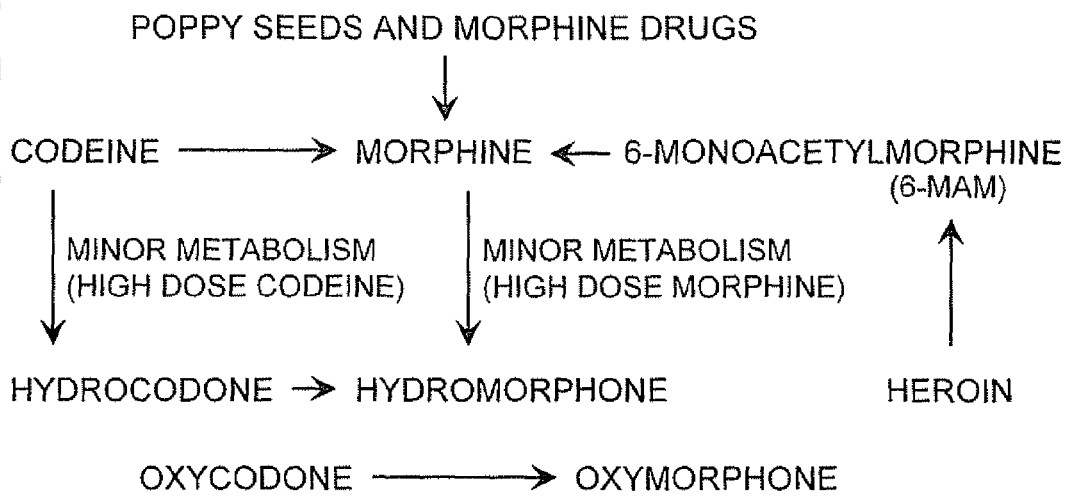
FIG. 2 is an exemplary diagram summary of opiate/opioid metabolism according to some embodiments of the present invention.
FIG. 3 is an exemplary diagram of the major and minor metabolic pathways for opiates and opioids according to some embodiments of the present invention.

A summary of the major and minor metabolism of opiate/opioids is provided in FIG. 2, and an opiate/opioid metabolism diagram is shown in FIG. 3.

For example, in heroin detection, the detection of 6-monoacetylmorphine is proof of heroin use. However, the absence of 6-monoacetylmorphine does not rule out heroin use when morphine is present. Common reasons for the presence of morphine include a morphine prescription, codeine prescription (because codeine metabolizes to morphine), dietary poppy seeds and heroin use. Therefore, determining whether a detected opiate/opioid is from a legitimate use or illicit use can be difficult.

In addition, patients may not have a drug present that was prescribed for a variety of reasons, including non-compliance with the prescription, diversion, fast metabolism, drug induced metabolism (e.g., rifampin), poor drug absorption (e.g., celiac disease) and/or dilute urine. Patients may also have a drug present that was not prescribed for various reasons, such as normal opiate/opioid metabolites from a legitimate prescription, opiate/opioid metabolite found when high doses of codeine or morphine are used (high dose codeine can metabolize to hydrocodone and high dose morphine can metabolize to hydromorphone), a prescription may have been obtained from another physician, the medication can be obtained from a spouse or friend, or/or there may be illicit use of a drug obtained without a prescription.

Methods and systems according to some embodiments of the present invention can test for the substances according to Tables 1-2 below.

TABLE 1

| Opiate/Opioid Panel | Generic or Brand Name | Retention Time | LC/MS-MS Threshold |
|---|---|---|---|
| Hydrocodone | Vicodin and others | 1-3 days | 5 ng/mL |
| Hydromorphone | Dilaudid | 2-4 days | 5 ng/mL |
| Oxycodone | Oxycontin, Tylox, Percoset | 1-3 days (SR 2-4 days) | 5 ng/mL |
| Oxymorphone | Numorphan, Opana | 1-3 days (SR 2-4 days) | 5 ng/mL |
| Codeine | Tylenol-3 | 1-3 days | 5 ng/mL |
| Morphine | MS Contin, Roxanol | 1-3 days | 5 ng/mL |
| 6-monoacetyl-morphine | Heroin metabolite | 1-3 days | 5 ng/mL |
| Meperidine | Demerol | 1-2 days | 5 ng/mL |
| Fentanyl | Durogesic, Actiq | 1-2 days | 2 ng/mL |
| Norfentanyl | Fentanyl metabolite | 1-4 days | 2 ng/mL |

TABLE 2

| Drug Screen | Generic Name | Retention Time | Screen/GC-MS Threshold |
|---|---|---|---|
| Alcohol | Ethanol | 2-14 hours | 0.02/0.02 g/dL |
| Amphetamines | Amphetamine MDMA, MDA Methamphetamine | 1-2 days | 300/150 ng/mL |
| Barbiturates | Amobarbital | 1-7 days | 200/200 ng/mL |
|  | Aprobarbital | 1-7 days |  |
|  | Butabarbital | 1-7 days |  |
|  | Butalbital | 1-48 hours |  |
|  | Pentobarbital | 1-24 hours |  |
|  | Phenobarbital | 1-3 weeks |  |
|  | Secobarbital | 1-24 hours |  |
| Benzodiazepines | Alprazolam metabolite | Therapeutic Dose: 3 days | 200/100 ng/mL |
|  | Chlordiazepoxide metabolite | Extended Dosage 4-6 weeks |  |
|  | Clonazepam metabolite |  |  |
|  | Clorazepate metabolite |  |  |
|  | Diazepam metabolite |  |  |
|  | Flunitrazepam metabolite |  |  |
|  | Flurazepam metabolite |  |  |
|  | Lorazepam |  |  |
|  | Nordiazepam |  |  |
|  | Oxazepam |  |  |
|  | Temazepam |  |  |
| Cocaine | Cocaine metabolite | 1-2 days | 300/150 ng/mL |
| Marijuana | THC metabolite | Heavy User: 4-6 weeks Moderate User: 2 weeks Light User: 0-4 days | 20/15 ng/mL |
| Methadone | Methadone metabolite | 3-11 days | 300/300 ng/mL |
| Phencyclidine | Phencyclidine | 8 days Chronic Use: up to 30 days | 25/25 ng/mL |
| Propoxyphene | Propoxyphene metabolite | 1-2 days | 300/300 ng/mL |

SR = Slow Release

An exemplary patient report is provided in FIG. 4A. As can be seen in FIG. 4, positive results for a drug are highlighted with an arrow indicating positive results. It should be understood that other techniques for visually drawing a viewer's attention to the positive results can be used, for example, by using all capital letters and/or color to indicate positive results. As can be seen in FIG. 4A, positive results are also printed at the beginning of the report with an interpretive comment, i.e., the hydrocodone positive result is consistent with a hydrocodone prescription, and the oxycodone positive result is discrepant because oxycodone should be negative. Accordingly, medical health professionals can quickly interpret the test results.

As shown in FIG. 4B, a requisition form can be used for ordering the test in which the ordering physician or other medical health professional identifies the drugs that the patient is currently taking, e.g., based on patient interviews, patient history, medical record(s), etc.). A box is checked next to each identified drug, and next to each box is a barcode for each specific prescription medication or class of prescription drug (e.g., in the case of non-opioids such as benzodiazepine). In particular embodiments, the practitioner can select barcodes (e.g., barcode stickers) corresponding to the prescriptions taken by the patient and affix the barcodes to the patient sample. In some embodiments, a barcode can be provided to indicate that prescription information is not known. Accordingly, the barcodes affixed to the patient sample (or provided with the patient sample) can be used to quickly and automatically enter patient information, such as prescription information, into an opioid/metabolite analyzer (such as the analyzer 108 in FIG. 1). Although FIG. 4B illustrates barcodes, it should be understood that other machine-readable codes can also be used, such as radio-frequency identification tags. For example, a barcode reader or other suitable automated reader can be used to receive the prescription information, and this reader can be included as part of the system 100 of FIG. 1. The prescription information can then be cross-checked, for example, using the bar coded patient record information for each specific drug or drug class and the flowcharts provided in FIGS. 5-28G. Accordingly, the report generation and cross-checking techniques described herein for comparing actual drug test results with prescribed medication can be fully or nearly fully automated.

Flowcharts for generating reports as shown in FIG. 4A are provided in FIGS. 5-28G. Where ratio percentages are provided, it should be understood that the ratios are between ±5%. For example, if a ratio is provided as less than 40%, the value should be understood to be less than about 35%-45%. The information derived from the flow charts provided in FIGS. 5-28G can be presented in any suitable form, including the exemplary patient report provided in FIG. 4A. For example, discrepant results can be highlighted and/or results that indicate the use of drugs of abuse or the use of drugs for which the patient does not have a prescription can be presented.

Figure 5:
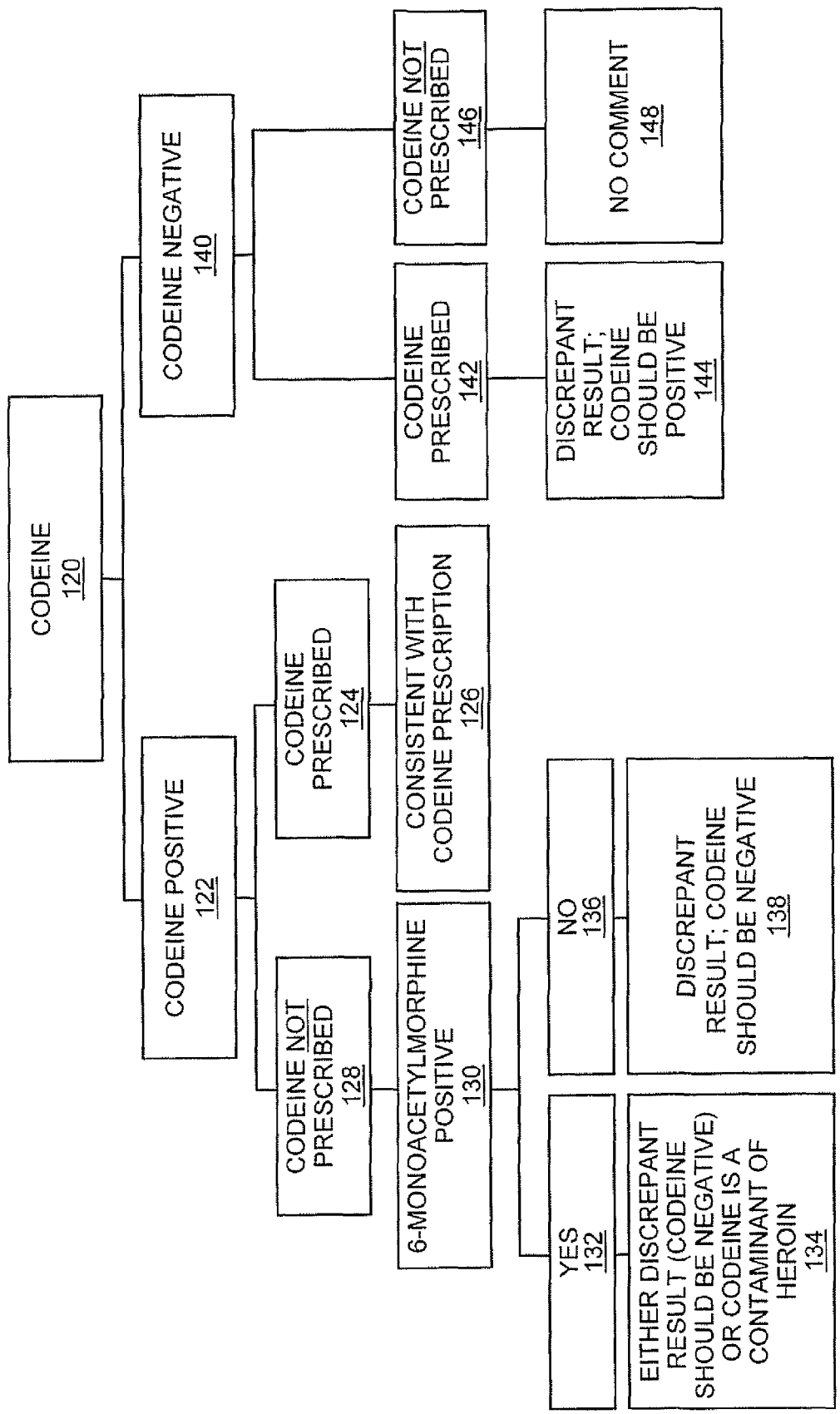
FIG. 5 is a block diagram of a medication/drug interpretation flow chart for codeine, in which prescription information has been considered according to some embodiments of the present invention.

For example, FIG. 5 illustrates a pain management or medication/drug interpretation flow chart for codeine 120, in which prescription information has been considered. If the test for codeine is positive at Block 122, and patient records indicate that codeine is prescribed at Block 124, then the result is considered consistent with codeine prescription at Block 126. If the test for codeine is positive at Block 122, and patient records indicate that codeine is not prescribed at Block 128, then it is determined whether 6-monoacetylmorphine is present at Block 130. If 6-monoacetylmorphine is positive at Block 132, then it is determined that there is either a discrepant result because the codeine test should be negative or the codeine is a contaminant of heroine (Block 134). If 6-monoacetylmorphine is negative at Block 136, then it is determined that there is a discrepant result because the codeine test should be negative (Block 138). If the test for codeine is negative at Block 140, and patient records indicate that codeine is prescribed at Block 142, then it is determined that there is a discrepant result because the codeine test should be positive (Block 144), which can indicate, e.g., patient non-compliance with a prescription. In contrast, there is no comment at Block 148 if patient records indicate that codeine is not prescribed (Block 146).

Figure 6:
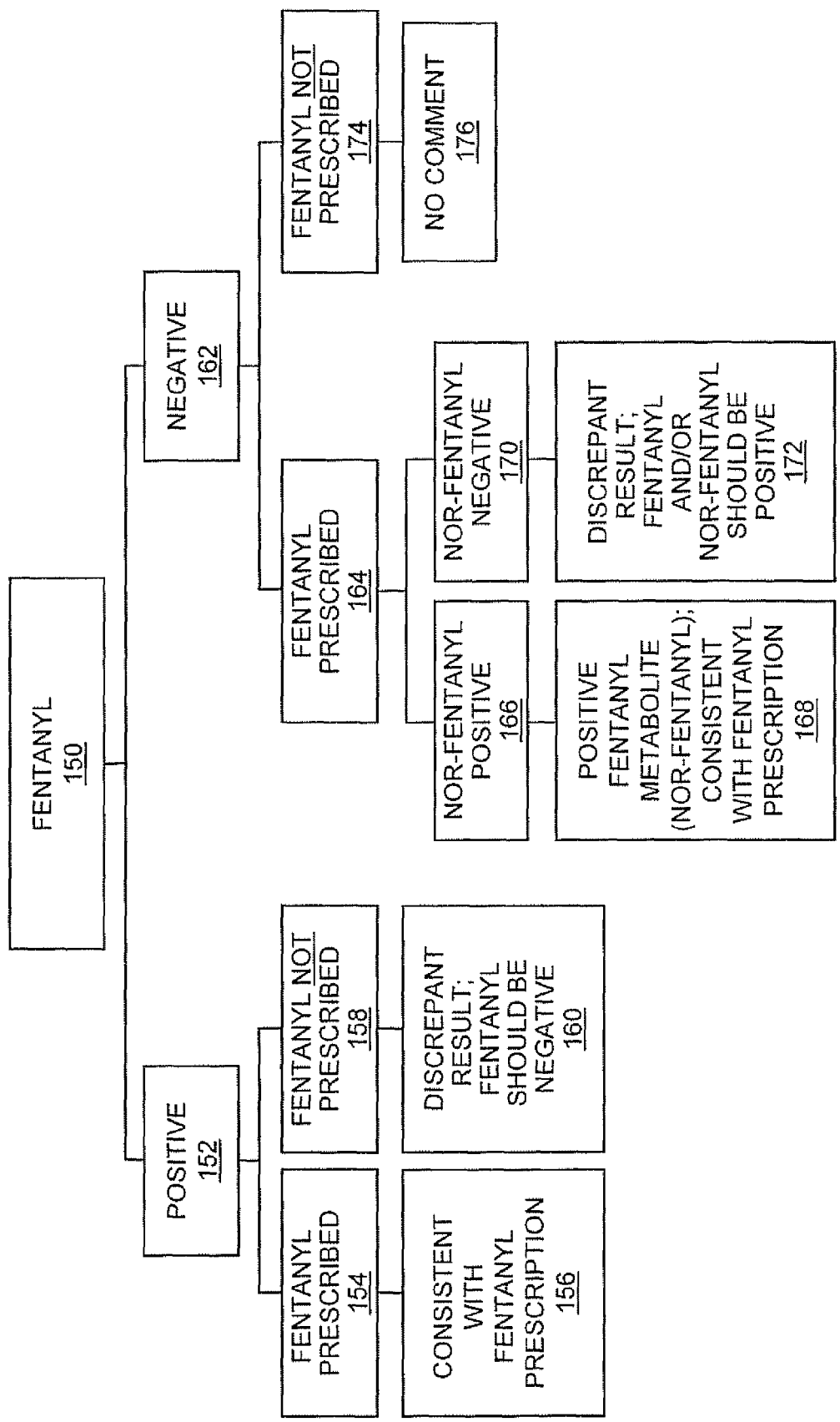
FIG. 6 is a block diagram of a medication/drug interpretation flow chart for fentanyl, in which prescription information has been considered according to some embodiments of the present invention.

Similarly, FIG. 6 illustrates a medication/drug interpretation flow chart for fentanyl 150, in which prescription information has been considered. If the test for fentanyl is positive at Block 152, and patient records indicate that fentanyl is prescribed at Block 154, then the result is considered consistent with fentanyl prescription at Block 156. If the test for codeine is positive at Block 152, and patient records indicate that fentanyl is not prescribed at Block 158, then it is determined that there is a discrepant result because the fentanyl test should be negative (Block 160). If the test for fentanyl is negative at Block 162 and patient records indicate that fentanyl is prescribed at Block 164, then it is determined whether nor-fentanyl is present. If the test for nor-fentanyl is positive at Block 166, then the result is considered consistent with fentanyl prescription at Block 168 because nor-fentanyl is a metabolite of fentanyl. If, however, the nor-fentanyl test is negative at Block 170, then it is determined that there is a discrepant result because fentanyl and/or nor-fentanyl should be positive (Block 172). In contrast, if the test for fentanyl is negative at Block 162 and patient records indicate that fentanyl is not prescribed at Block 174, then there is no comment at Block 176.

Figure 7:
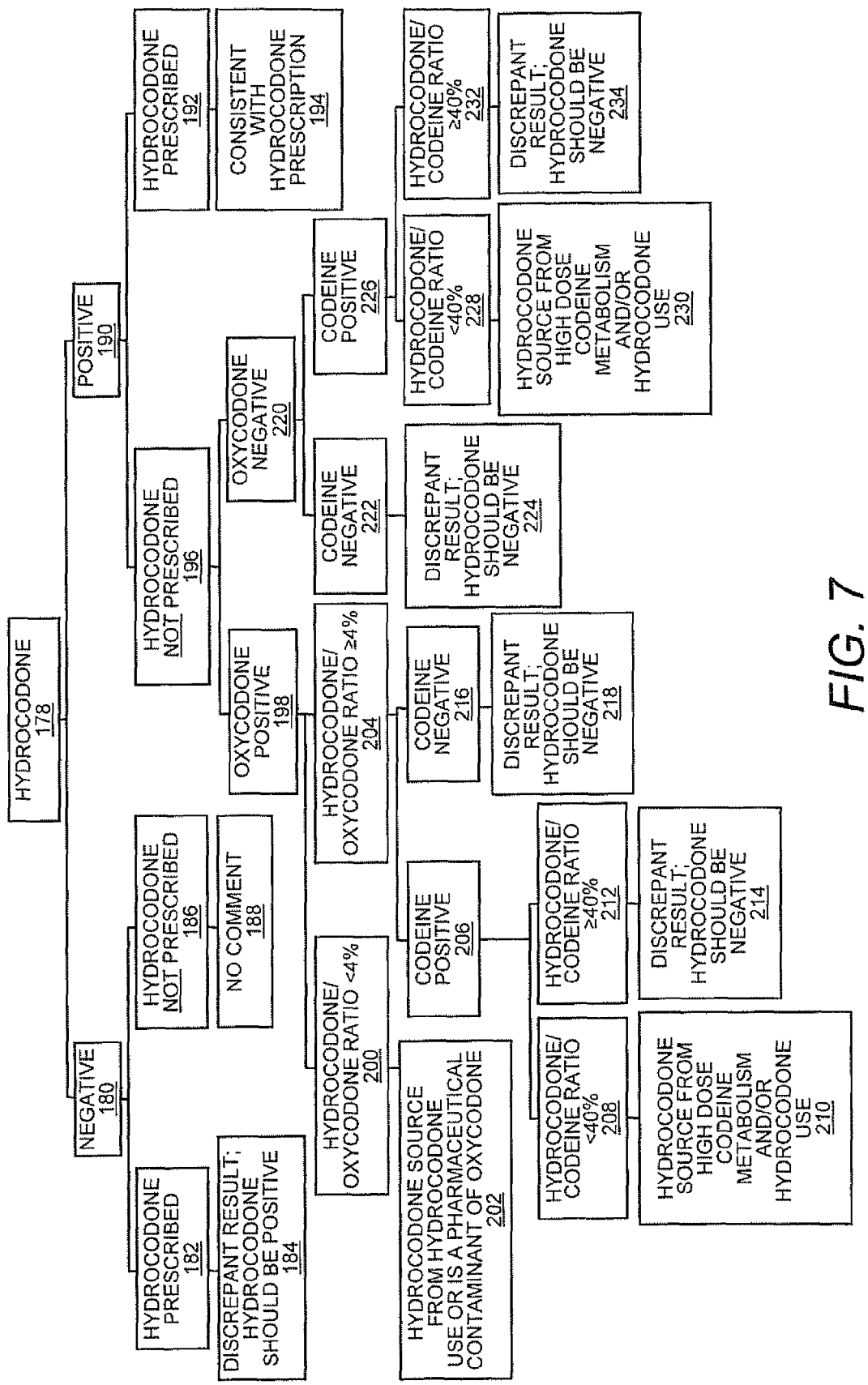
FIG. 7 is a block diagram of a medication/drug interpretation flow chart for hydrocodone, in which prescription information has been considered according to some embodiments of the present invention.

FIG. 7 shows a medication/drug interpretation flow chart for hydrocodone 178, in which prescription information has been considered. If the test for hydrocodone is negative in Block 180, and patient records indicate that hydrocodone is prescribed at Block 182, then it is determined that there is a discrepant result because the hydrocodone test should be positive (Block 184). If, however, the test for hydrocodone is negative in Block 180, and the patient records indicate that hydrocodone is not prescribed (Block 186), then there is no comment at Block 188. In contrast, if the test for hydrocodone is positive in Block 190, and patient records indicate that hydrocodone is prescribed at Block 192, then the result is considered consistent with hydrocodone prescription at Block 194. If, however, patient records indicate that hydrocodone is not prescribed at Block 196, then it is determined whether oxycodone is present. If the oxycodone test is positive at Block 198, then the ratio of hydrocodone/oxycodone is determined. If the hydrocodone/oxycodone ratio is <4% at Block 200, then it is determined that the hydrocodone source is from hydrocodone use or is a pharmaceutical contaminant of oxycodone at Block 202. If, however, the hydrocodone/oxycodone ratio is ≧4% at Block 204, then it is determined whether codeine is present. If the codeine test is positive at Block 206, then the ratio of hydrocodone/codeine is determined, in which a hydrocodone/codeine ratio of <40% at Block 208 indicates that the hydrocodone source is from high dose codeine metabolism and/or hydrocodone use (Block 210), whereas a hydrocodone/codeine ratio of ≧40% at Block 212 indicates a discrepant result at Block at 214, because hydrocodone should be negative. If, on the other hand, codeine is negative at Block 216, then it is determined that there is a discrepant result because hydrocodone should be negative (Block 218). A negative oxycodone result at Block 220 prompts a determination of whether codeine is present. If the codeine test is negative at Block 222, then it is determined that there is a discrepant result because hydrocodone should be negative (Block 224). If, however, the test for codeine is positive at Block 226, then the ratio of hydrocodone/codeine is determined. A hydrocodone/codeine ratio of <40% at Block 228 indicates that the hydrocodone source is from high dose codeine metabolism and/or hydrocodone use (Block 230), whereas a hydrocodone/codeine ratio of ≧40% at Block 232 indicates a discrepant result at Block at 234, because hydrocodone should be negative.

Figure 8A:
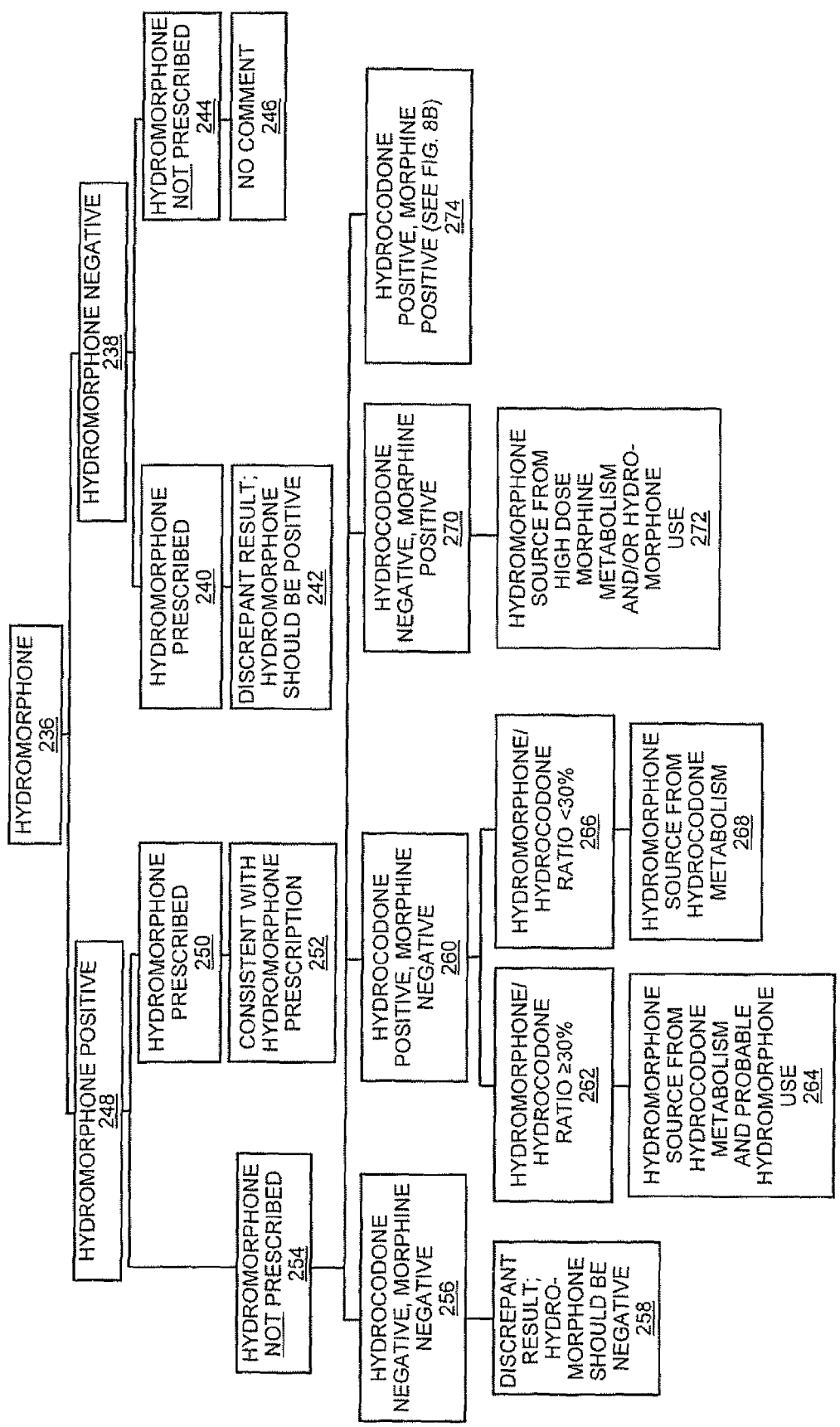
FIGS. 8A-8B are block diagrams of a medication/drug interpretation flow chart for hydromorphone, in which prescription information has been considered according to some embodiments of the present invention.
Figure 8B:
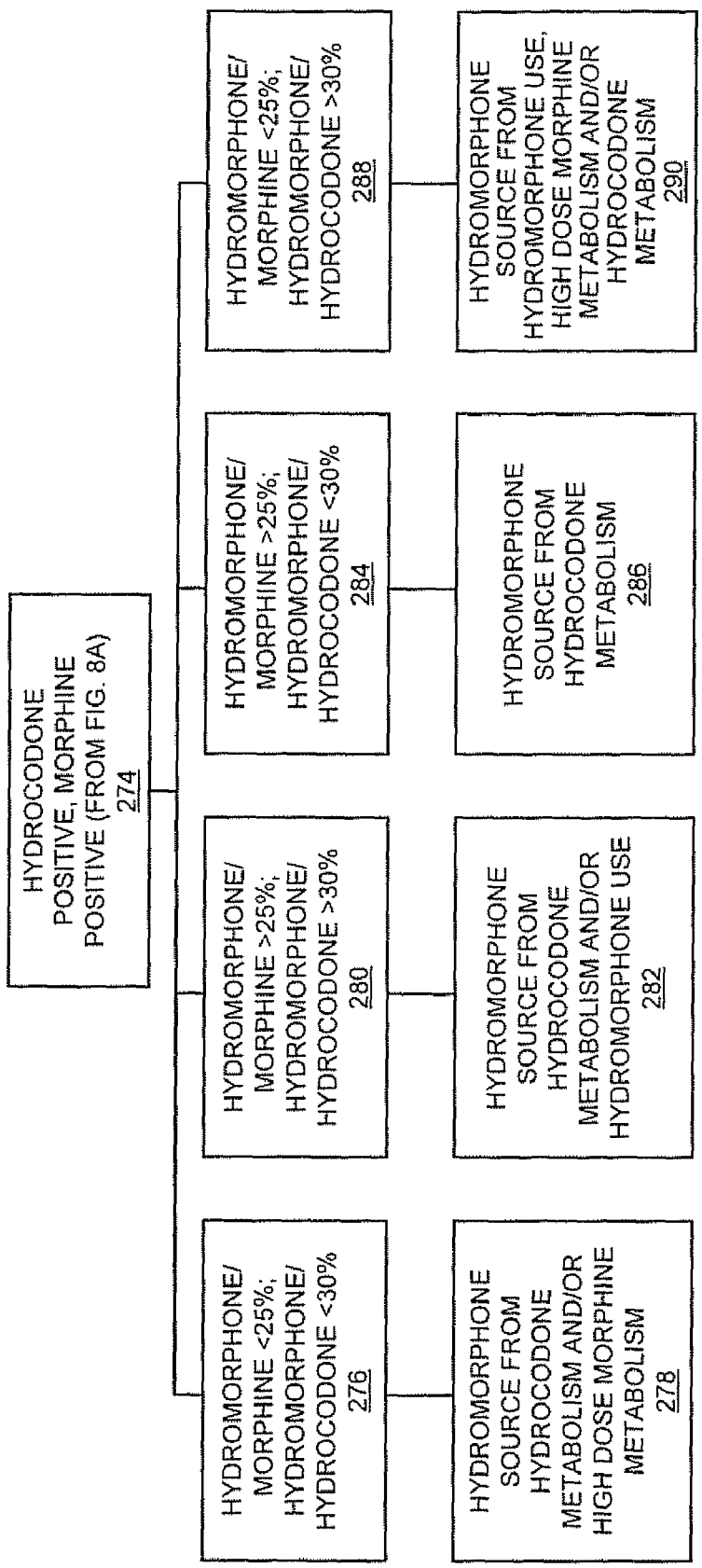

FIGS. 5A and 8B illustrate a medication/drug interpretation flow chart for hydromorphone 236, in which prescription information has been considered. If the test for hydromorphone is negative at Block 238, and patient records indicate that hydromorphone is prescribed (Block 240), then it is determined that there is a discrepant result because hydromorphone should be positive (Block 242). If, however, the patient records indicate that hydromorphone is not prescribed (Block 244), then there is no comment at Block 246. In contrast, a positive hydromorphone result at Block 248 and an indication in the patient records that hydromorphone is prescribed (Block 250) is consistent with hydromorphone prescription (Block 252). If, however, hydromorphone is positive in Block 248 and hydromorphone is not prescribed (Block 254), then it is determined whether hydrocodone and/or morphine are present. Negative hydrocodone and negative morphine tests at Block 256 indicates a discrepant results because hydromorphone should be present (Block 258). If the hydrocodone test is positive and the morphine test is negative (Block 260), the ratio of hydromorphone/hydrocodone is determined, in which a hydromorphone/hydrocodone ratio of ≧30% at Block 262 indicates that the hydromorphone source is from hydrocodone metabolism and probable hydromorphone use (Block 264), whereas a hydromorphone/hydrocodone ratio of <30% at Block 266 indicates that the hydromorphone source is from hydrocodone metabolism (Block 268). A negative hydrocodone test and positive morphine test at Block 270 indicates that the hydromorphone source is from high dose morphine metabolism and/or hydromorphone use (Block 272). When both hydrocodone and morphine tests are positive at Block 274, then hydromorphone/morphine and hydromorphone/hydrocodone ratios are determined as shown in FIG. 8B. With continued reference to FIG. 8B, hydromorphone/morphine ratio of <25% and hydromorphone/hydrocodone ratio of <30% (Block 276) indicates that the hydromorphone source is from hydrocodone metabolism and/or high dose morphine metabolism (Block 278). A hydromorphone/morphine ratio of >25% and hydromorphone/hydrocodone ratio of >30% (Block 280) indicates that the hydromorphone source is from hydrocodone metabolism and/or hydromorphone use (Block 282). A hydromorphone/morphine ratio of >25% and hydromorphone/hydrocodone ratio of <30% (Block 284) indicates that the hydromorphone source is from hydrocodone metabolism (Block 286). A hydromorphone/morphine ratio of <25% and hydromorphone/hydrocodone ratio of >30% (Block 288) indicates that the hydromorphone source is from hydromorphone use, high does morphine metabolism and/or hydrocodone metabolism (Block 290).

Figure 9:
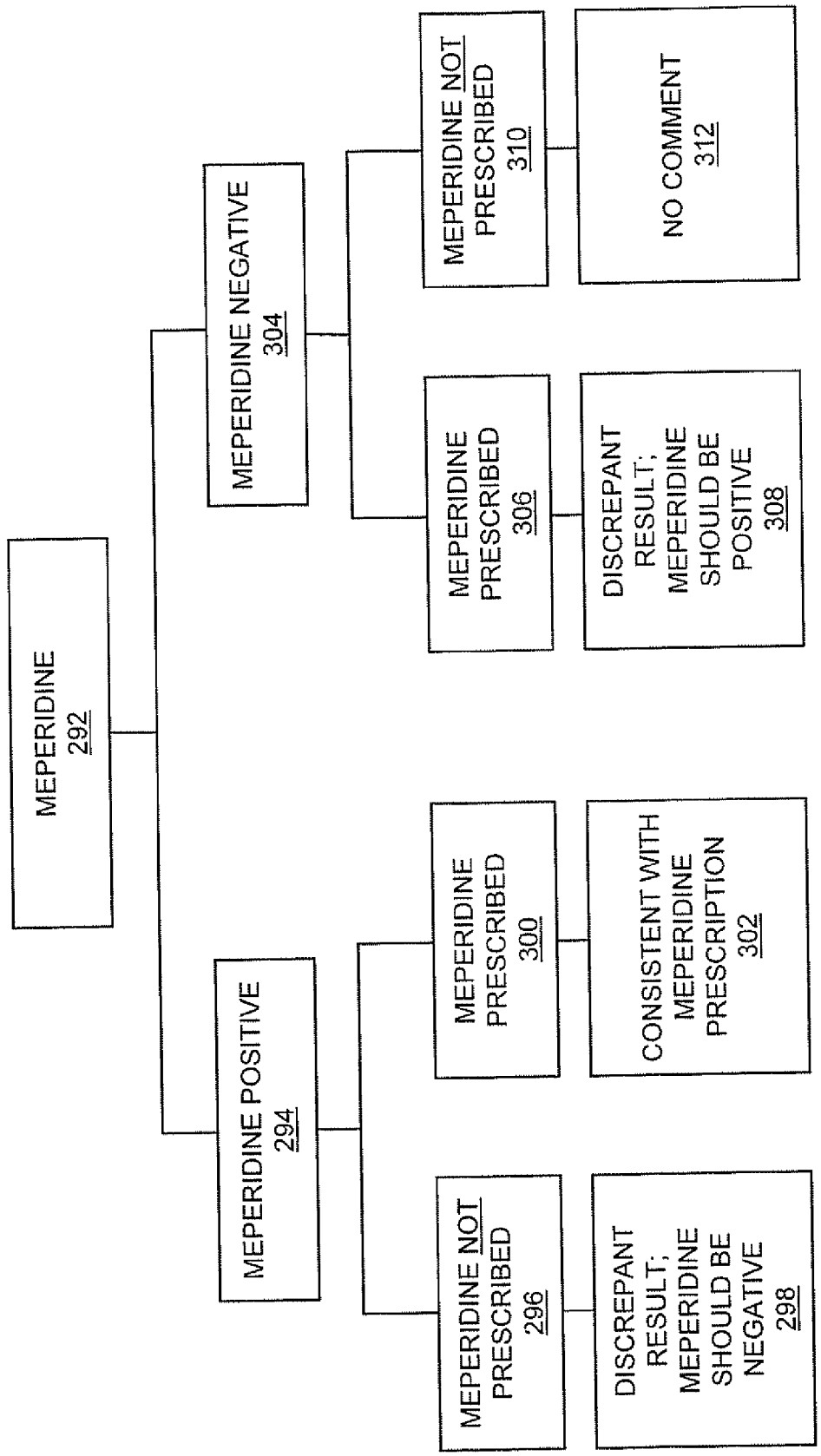
FIG. 9 is a block diagram of a medication/drug interpretation flow chart for meperidine, in which prescription information has been considered according to some embodiments of the present invention.

A medication/drug interpretation flow chart for meperidine 292, in which prescription information has been considered, is illustrated in FIG. 9. If the test for meperidine is positive in Block 294, and patient records indicate that meperidine is not prescribed at Block 296, then it is determined that there is a discrepant result because the meperidine test should be negative (Block 298). If, however, the test for meperidine is positive in Block 294, and the patient records indicate that meperidine is prescribed (Block 300), then the results are consistent with meperidine prescription (Block 302). In contrast, if the test for meperidine is negative in Block 304, and patient records indicate that meperidine is prescribed at Block 306, then it is determined that there is a discrepant result because the meperidine test should be positive (Block 308). If, however, patient records indicate that meperidine is not prescribed at Block 310, there is no comment in Block 312.

Figure 10:
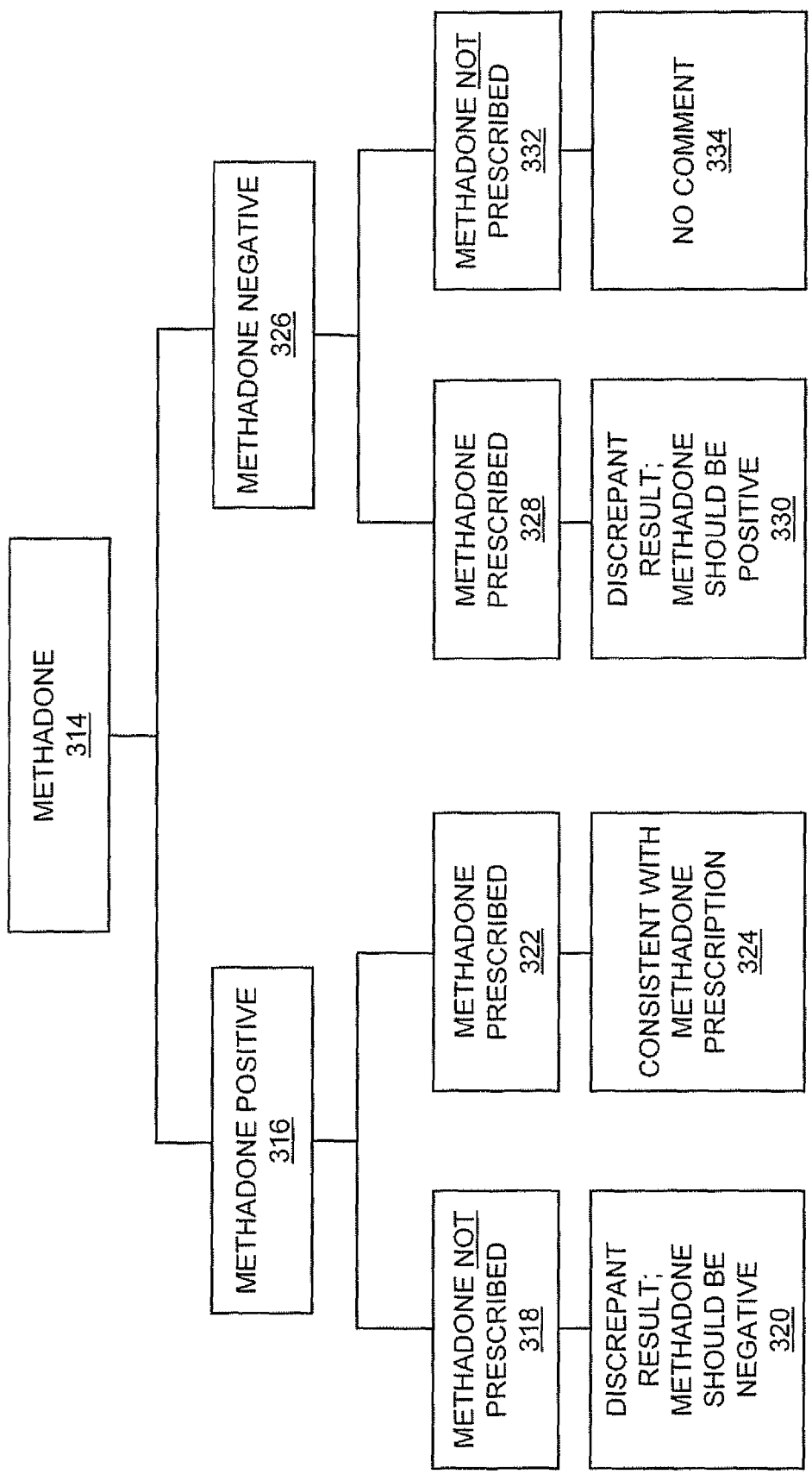
FIG. 10 is a block diagram of a medication/drug interpretation flow chart for methadone, in which prescription information has been considered according to some embodiments of the present invention.

A medication/drug interpretation flow chart for methadone 314, in which prescription information has been considered, is illustrated in FIG. 10. If the test for methadone is positive in Block 316, and patient records indicate that methadone is not prescribed at Block 318, then it is determined that there is a discrepant result because the methadone test should be negative (Block 320). If, however, the test for methadone is positive in Block 316, and the patient records indicate that methadone was prescribed (Block 322), then the results are considered consistent with methadone prescription (Block 324). In contrast, if the test for methadone is negative in Block 326, and patient records indicate that methadone is prescribed at Block 328, then it is determined that there is a discrepant result because the methadone test should be positive (Block 330). If, however, patient records indicate that methadone is not prescribed at Block 332, there is no comment in Block 334.

Figure 11:
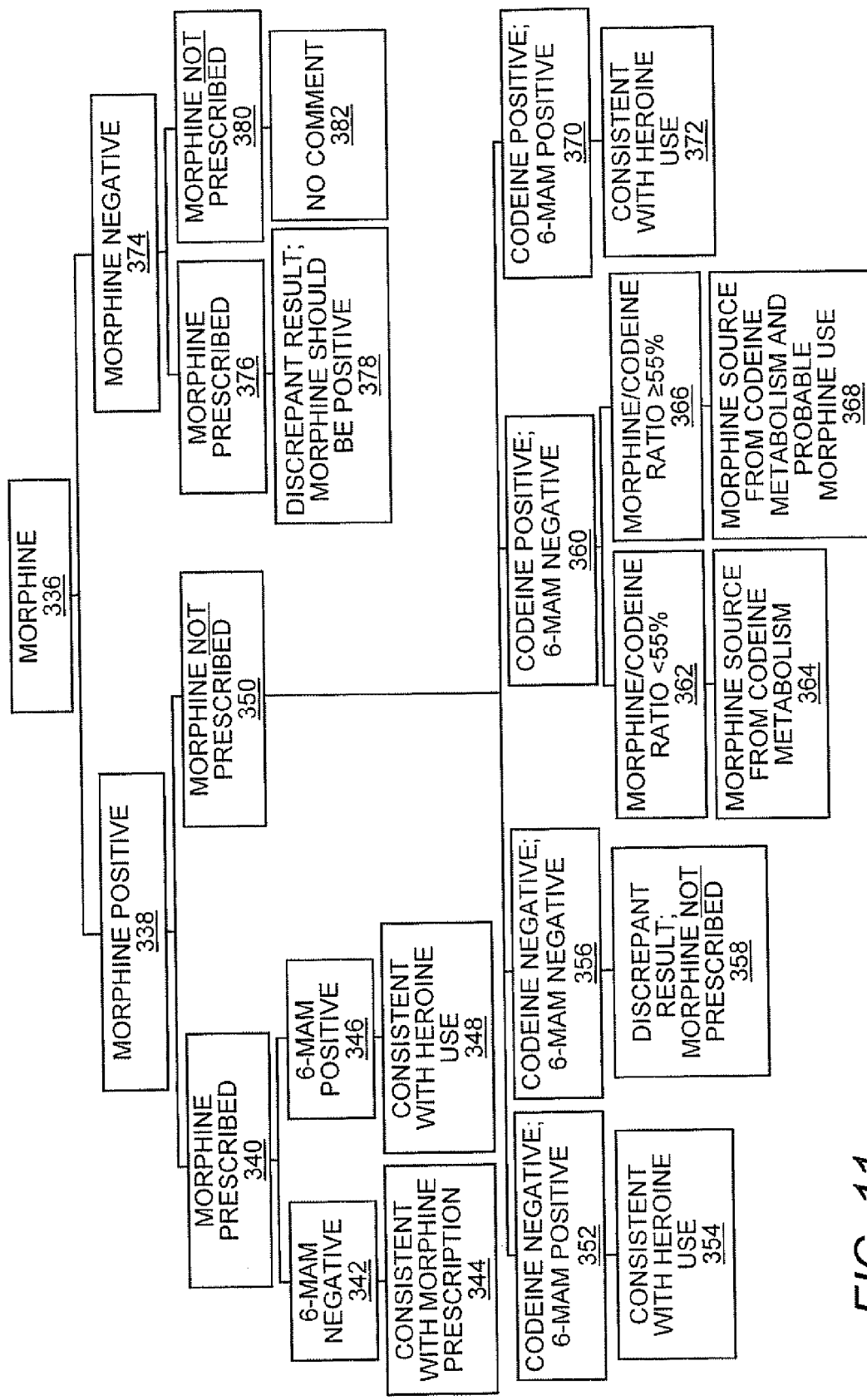
FIG. 11 is a block diagram of a medication/drug interpretation flow chart for morphine, in which prescription information has been considered according to some embodiments of the present invention.

FIG. 11 shows a medication/drug interpretation flow chart for morphine 336, in which prescription information has been considered. If the test for morphine is positive in Block 338 and patient records indicate that morphine is prescribed at Block 340, then it is determined whether 6-monoacetylmorphine (6-MAM) is present. A negative 6-MAM test result at Block 342 is consistent with a morphine prescription (Block 344). However, a positive 6-MAM test result at Block 346 is consistent with heroine use (Block 348). If the test for morphine is positive in Block 338 and patient records indicate that morphine is not prescribed at Block 350, then it is determined whether codeine and/or 6-MAM are present. A negative codeine test and positive 6-MAM test at Block 352 is consistent with heroine use (Block 354). When both codeine and 6-MAM tests are negative at Block 356, then it is determined that there is a discrepant result because morphine is not prescribed (Block 358). If the codeine test is positive and the 6-MAM test is negative (Block 360), then morphine/codeine ratios are determined. A morphine/codeine ratio <55% at Block 362 indicates that the morphine source is from codeine metabolism (Block 364), whereas a morphine/codeine ratio ≧55% at Block 366 indicates that the morphine source is from codeine metabolism and probable morphine use (Block 368). When both the codeine test and 6-MAM test are positive at Block 370, the results are determined to be consistent with heroine use (Block 372). If the test for morphine is negative in Block 374 and patient records indicate that morphine is prescribed at Block 376, then it is determined that there is a discrepant result because morphine should be positive (Block 378). If, however, the test for morphine is negative in Block 374 and patient records indicate that morphine is not prescribed at Block 380, then there is no comment at Block 382.

Figure 12:
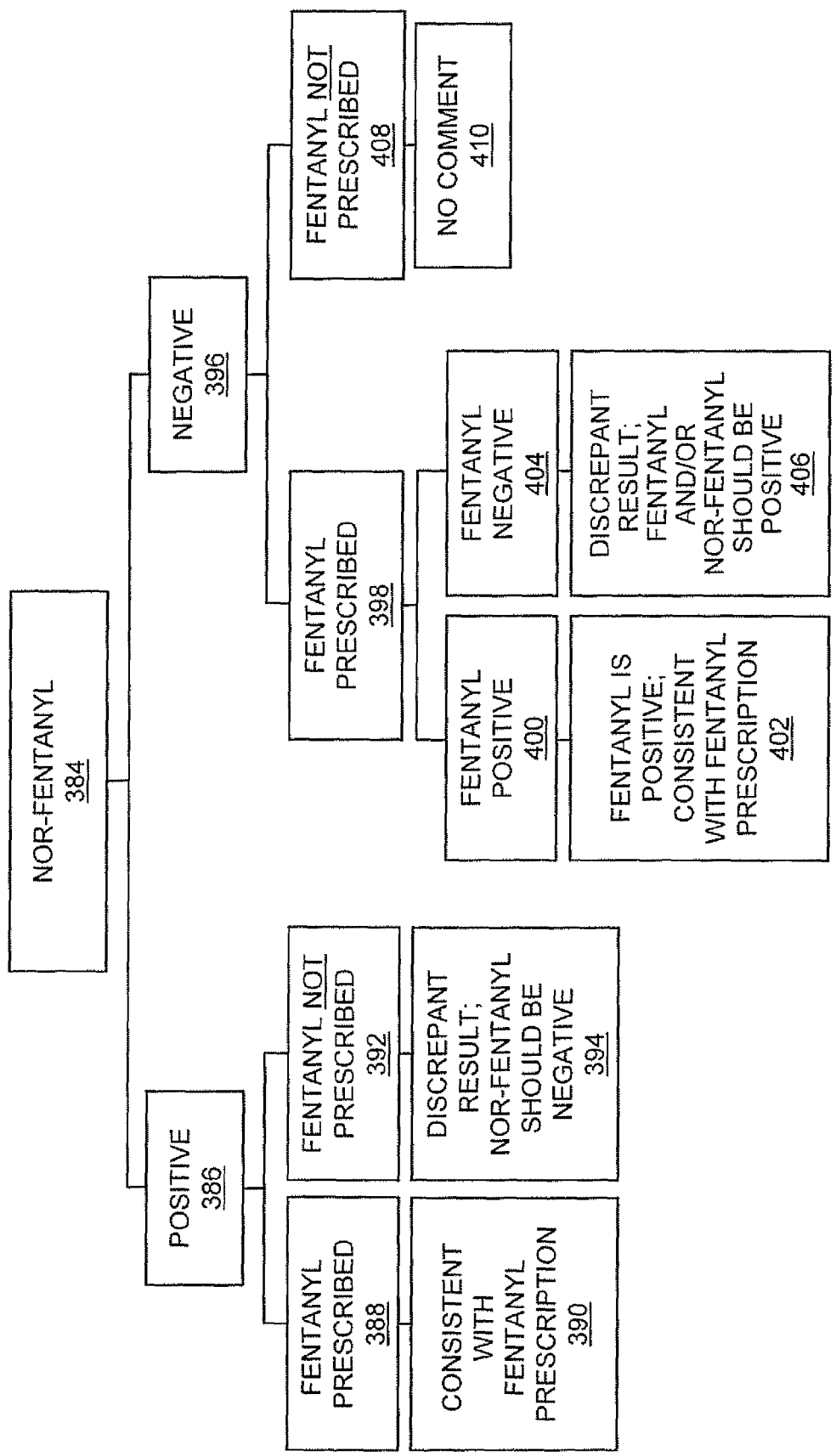
FIG. 12 is a block diagram of a medication/drug interpretation flow chart for nor-fentanyl, in which prescription information has been considered according to some embodiments of the present invention.

FIG. 12 illustrates a medication/drug interpretation flow chart for nor-fentanyl 384, in which prescription information has been considered. If the test for nor-fentanyl is positive in Block 386 and patient records indicate that fentanyl is prescribed at Block 388, then the results are considered consistent with fentanyl prescription (Block 390). If the test for nor-fentanyl is positive in Block 386 and patient records indicate that fentanyl is not prescribed (Block 392), then it is determined that there is a discrepant result because nor-fentanyl should be negative (Block 394). If the test for nor-fentanyl is negative in Block 396 and patient records indicate that fentanyl is prescribed at Block 398, then it is determined whether fentanyl is present. A positive fentanyl test at Block 400 is consistent with fentanyl prescription (Block 402), whereas a negative fentanyl test at Block 404 indicates a discrepant result because the fentanyl and/or nor-fentanyl test should be positive (Block 406). If, on the other hand, the test for nor-fentanyl is negative in Block 396 and patient records indicate that fentanyl is not prescribed at Block 408, then there is no comment in Block 410.

Figure 13:
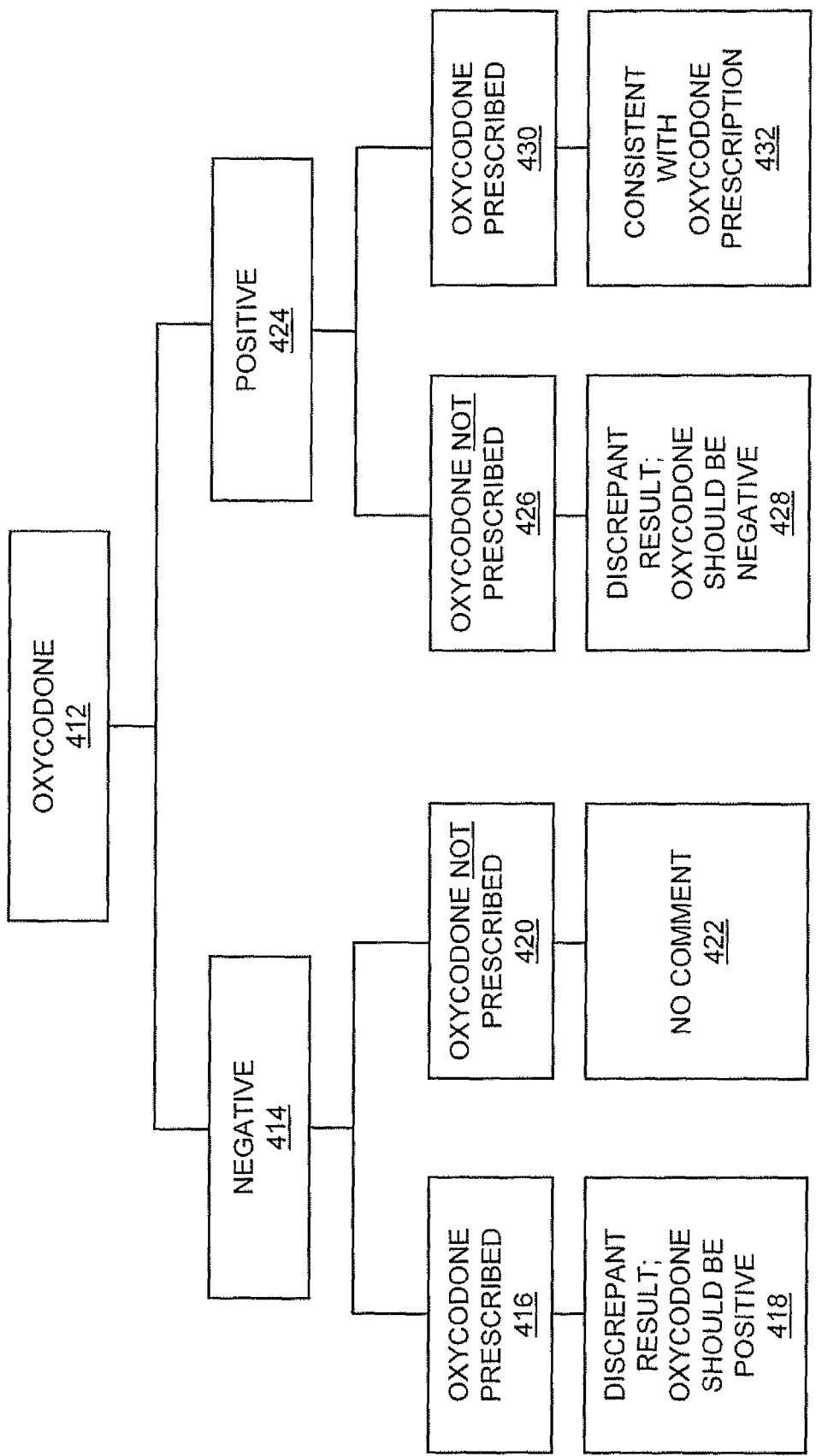
FIG. 13 is a block diagram of a medication/drug interpretation flow chart for oxycodone, in which prescription information has been considered according to some embodiments of the present invention.

A medication/drug interpretation flow chart for oxycodone 412, in which prescription information has been considered, is illustrated in FIG. 13. If the test for oxycodone is negative in Block 414, and patient records indicate that oxycodone is prescribed at Block 416, then it is determined that there is a discrepant result because the oxycodone test should be positive (Block 418). If, however, the test for oxycodone is negative in Block 414, and the patient records indicate that oxycodone is not prescribed (Block 420), then there is no comment (Block 422). In contrast, if the test for oxycodone is positive in Block 424, and patient records indicate that oxycodone is not prescribed at Block 426, then it is determined that there is a discrepant result because the oxycodone test should be negative (Block 428). If, however, patient records indicate that oxycodone is prescribed at Block 430, the results are considered consistent with oxycodone prescription (Block 432).

Figure 14:
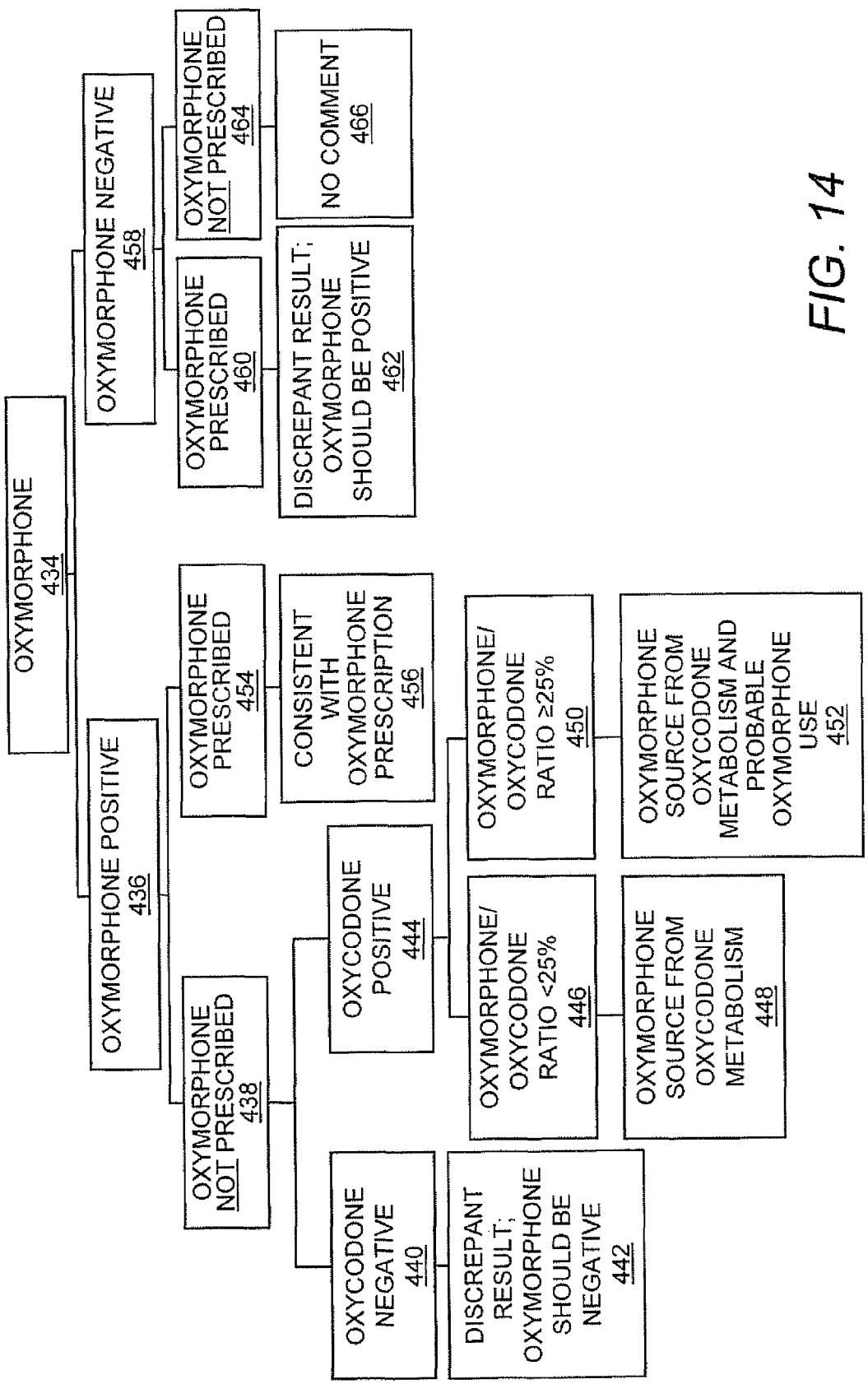
FIG. 14 is a block diagram of a medication/drug interpretation flow chart for oxymorphone, in which prescription information has been considered according to some embodiments of the present invention.

FIG. 14 illustrates a medication/drug interpretation flow chart for oxymorphone 434, in which prescription information has been considered. If the test for oxymorphone is positive in Block 436 and patient records indicate that oxymorphone is not prescribed at Block 438, then the presence of oxycodone is determined. If the test for oxycodone is negative (Block 440), then it is determined that there is a discrepant result because oxymorphone should be negative (Block 442). If, however, the oxycodone test is positive in Block 444, then the ratio of oxymorphone/oxycodone is compared, in which an oxymorphone/oxycodone ratio of <25% (Block 446) indicates that the source of oxymorphone is from oxycodone metabolism (Block 448), and an oxymorphone/oxycodone ratio of ≧25% (Block 450) indicates that the source of oxymorphone is from oxycodone metabolism and probable oxymorphone use (Block 452). If the test for oxymorphone is positive in Block 436 and patient records indicate that oxymorphone is prescribed at Block 454, the result is considered consistent with oxymorphone prescription (Block 456). If, one the other hand, the test for oxymorphone is negative in Block 458 and patient records indicate that oxymorphone is prescribed at Block 460, then it is determined that there is a discrepant result because oxymorphone should be positive (Block 462). If the oxymorphone test is negative in Block 458, and patient records indicate that oxymorphone is not prescribed (Block 464), then there is no comment in Block 466.

Figure 15:
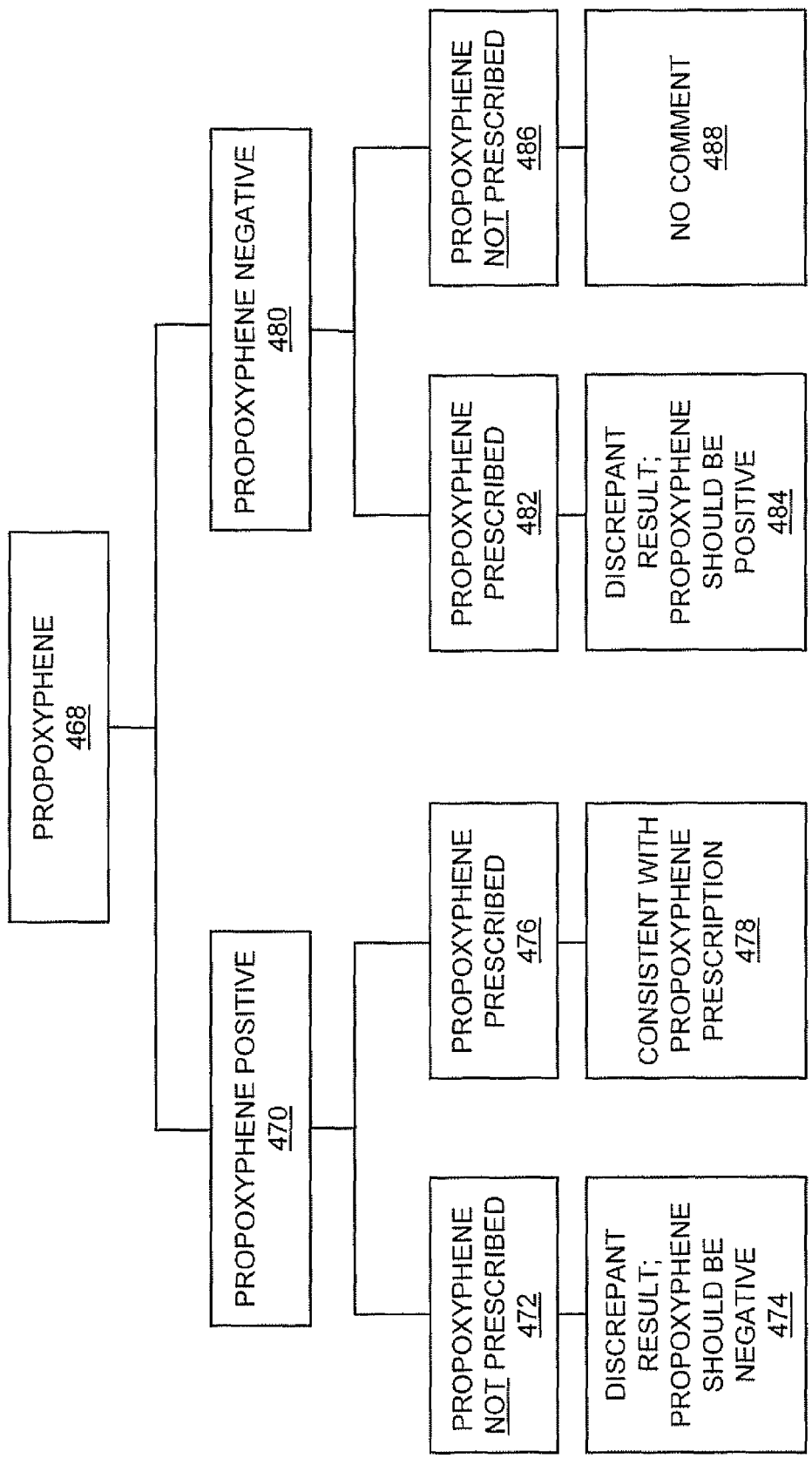
FIG. 15 is a block diagram of a medication/drug interpretation flow chart for propoxyphene, in which prescription information has been considered according to some embodiments of the present invention.

A medication/drug interpretation flow chart for propoxyphene 468, in which prescription information has been considered, is illustrated in FIG. 15. If the test for propoxyphene is positive in Block 470, and patient records indicate that propoxyphene is not prescribed at Block 472, then it is determined that there is a discrepant result because the propoxyphene test should be negative (Block 474). If, however, the test for propoxyphene is positive in Block 470, and the patient records indicate that propoxyphene is prescribed (Block 476), then the results are considered consistent with propoxyphene prescription (Block 478). In contrast, if the test for propoxyphene is negative in Block 480, and patient records indicate that propoxyphene is prescribed at Block 482, then it is determined that there is a discrepant result because the propoxyphene test should be positive (Block 484). If, however, patient records indicate that propoxyphene is not prescribed at Block 486, there is no comment in Block 488.

Figure 16A:
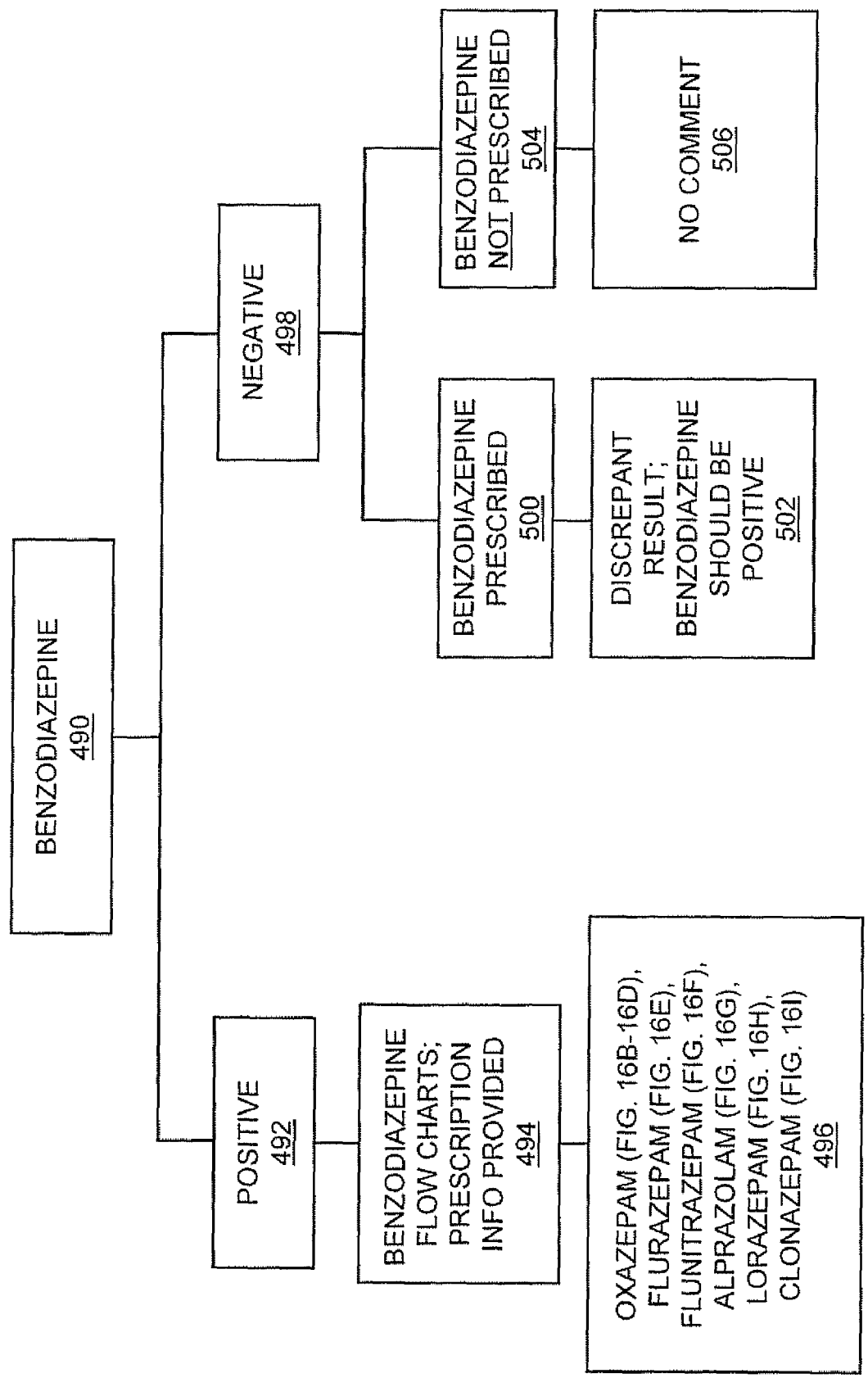
FIGS. 16A-16I are a block diagram of a medication/drug interpretation flow chart for benzodiazepine (FIG. 16A) and benzodiazepine derivatives oxazepam (FIG. 16B-16D), flurazepam (FIG. 16E), flunitrazepam (FIG. 16F), alprazolam (FIG. 16G), lorazepam (FIG. 16H), and clonazepam (FIG. 16I), in which prescription information has been considered according to some embodiments of the present invention.

FIG. 16A illustrates a medication/drug interpretation flow chart for benzodiazepine 490, in which prescription information has been considered. If the test for benzodiazepine is positive in Block 492, then the flowcharts for benzodiazepine derivatives are referenced in Block 494, with determinations for oxazepam (FIGS. 16B-16D), flurazepam (FIG. 16E), flunitrazepam (FIG. 16F), Alpraxolam (FIG. 16G), lorazepam (FIG. 16H) and clonazepam (FIG. 16I) being made in Block 496. If the test for benzodiazepine is negative in Block 498, and patient records indicate that benzodiazepine is prescribed at Block 500, then it is determined that there is a discrepant result because the benzodiazepine test should be positive (Block 502). If, however, the test for benzodiazepine is negative in Block 498, and the patient records indicate that benzodiazepine is not prescribed (Block 504), then there is no comment in Block 506.

Figure 16B:
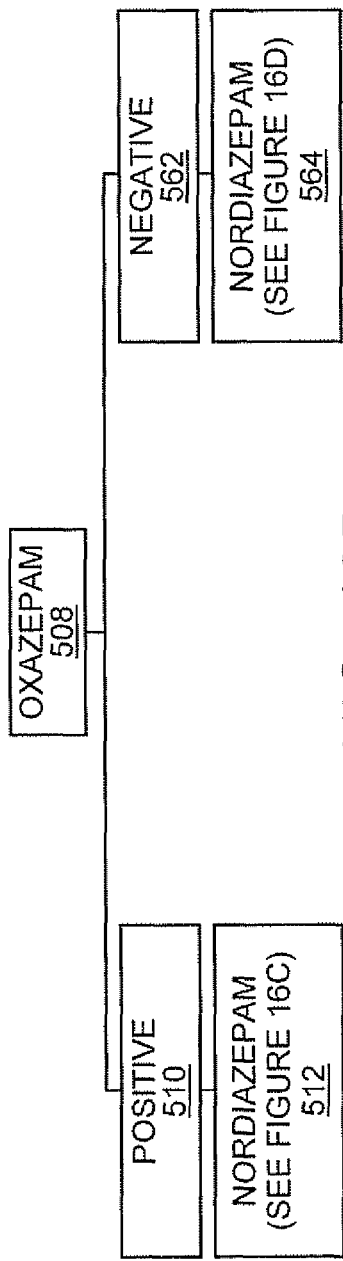
Figure 16E:
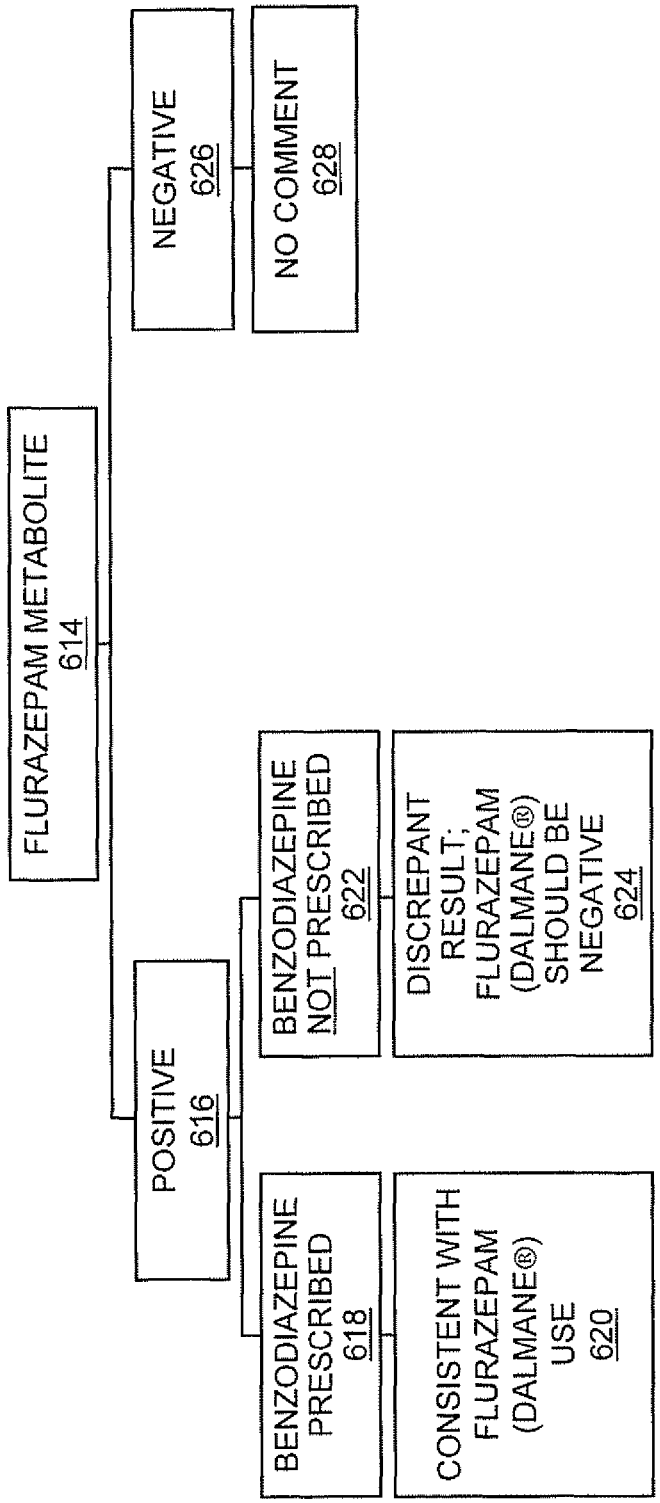
Figure 16C:
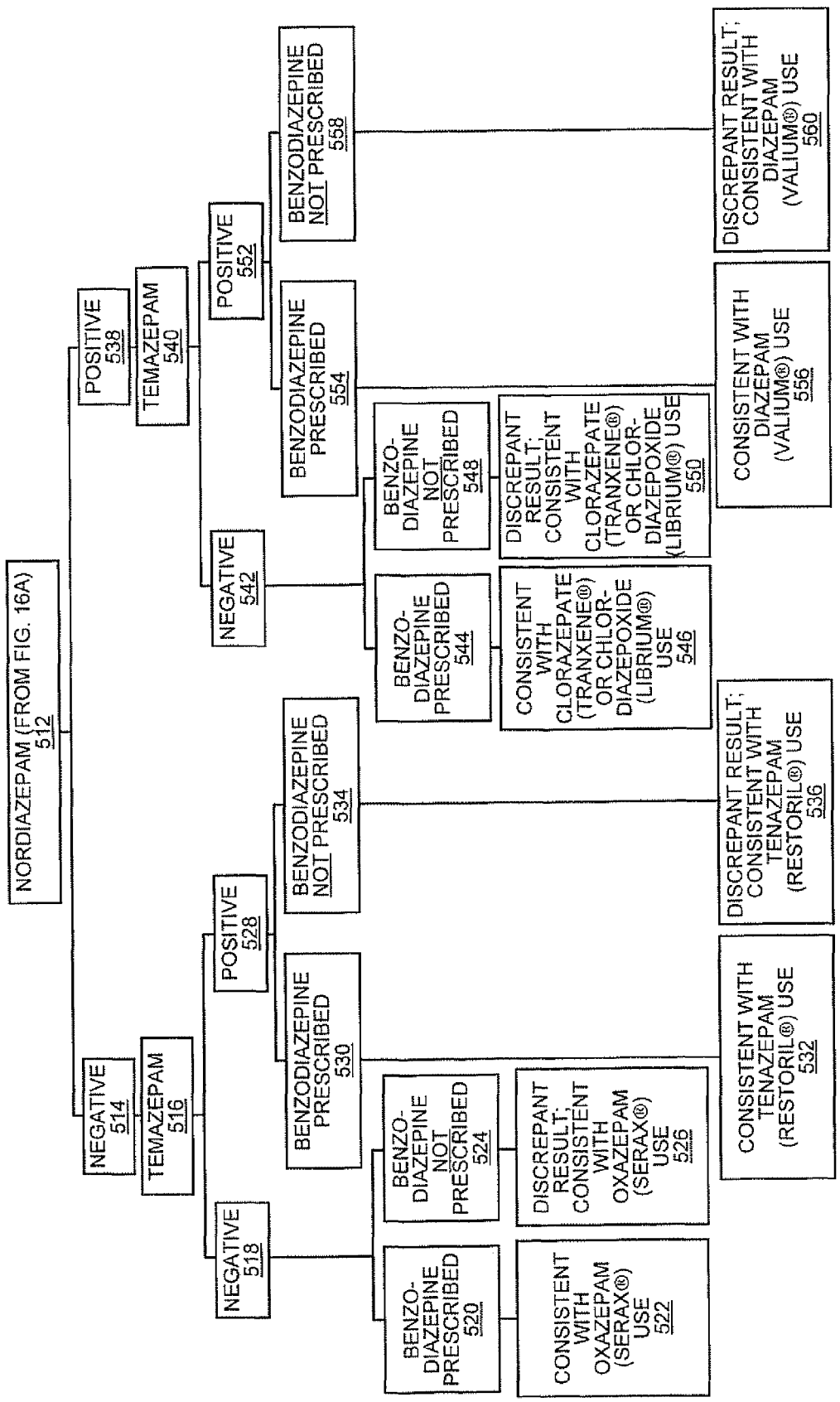
Figure 16D:
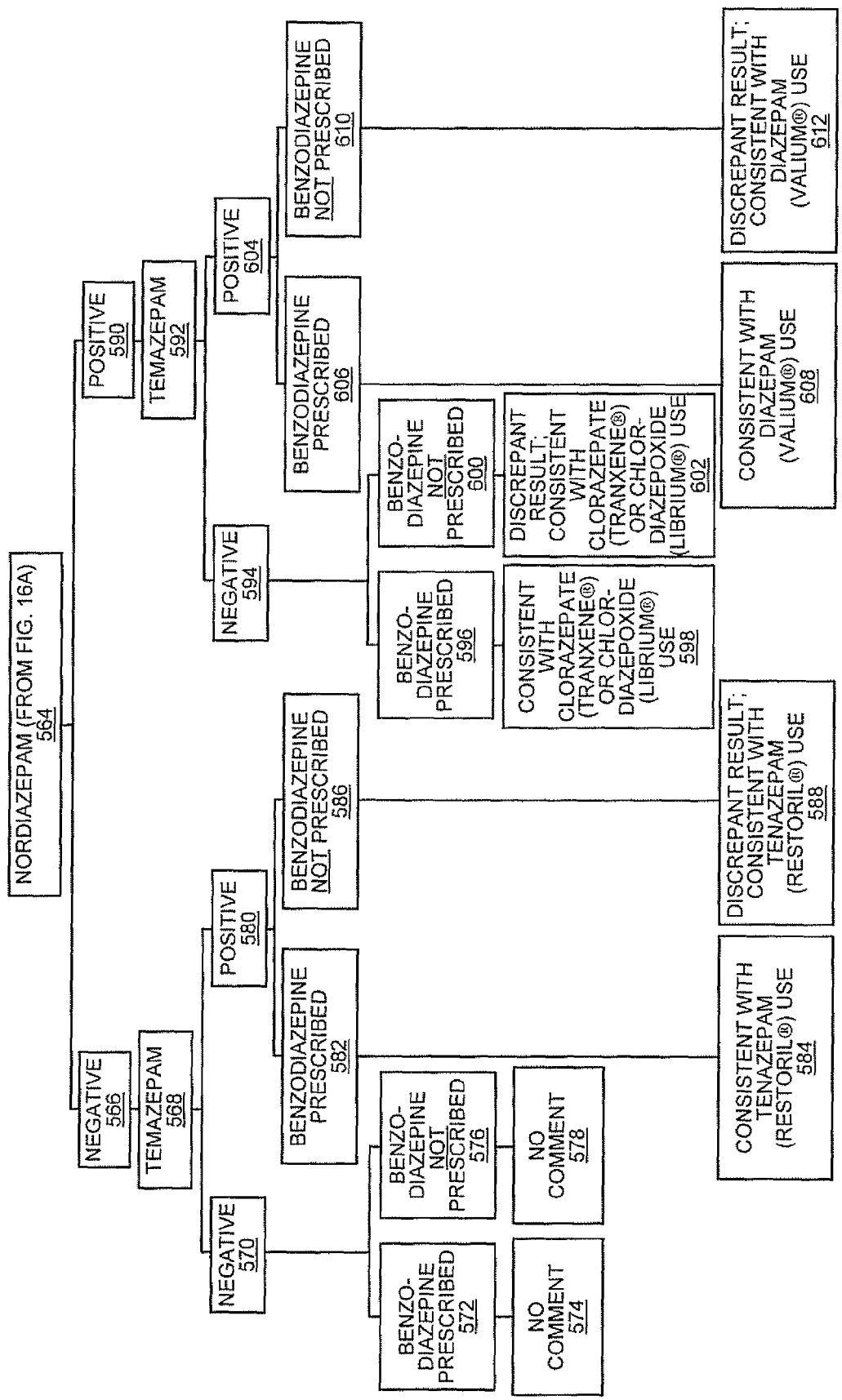

The pain management flow chart for oxazepam 508, in which prescription information has been considered, is illustrated in FIGS. 16B-16D. If the test for oxazepam is positive in Block 510, then the presence of nordiazepam is determined in Block 512 (FIG. 16C). If the test for nordiazepam is negative in Block 514, then the presence of temazepam is determined in Block 516. If the test for temazepam is negative in Block 518, and patient records indicate that benzodiazepine is prescribed (Block 520), the results are considered consistent with oxazepam (SERAX®) use (Block 522). If, however, the temazepam test is negative in Block 518, and patient records indicate that benzodiazepine is not prescribed (Block 524), then it is determined that there is a discrepant result consistent with oxazepam (SERAX®) use (Block 526). If the test for temazepam is positive in Block 528, and patient records indicate that benzodiazepine is prescribed (Block 530), the results are considered consistent with tenazepam (RESTORIL®) use (Block 532). If, however, the temazepam test is positive in Block 528, and patient records indicate that benzodiazepine is not prescribed (Block 534), then it is determined that there is a discrepant result consistent with tenazepam (RESTORIL®) use (Block 536). In contrast, if the test for nordiazepam is positive in Block 538, then the presence of temazepam is determined in Block 540. If the test for temazepam is negative in Block 542, and patient records indicate that benzodiazepine is prescribed (Block 544), the results are considered consistent with clorazepate (TRANXENE®) or chlordiazepoxide (LIBRIUM®) use (Block 546). If, however the temazepam test is negative in Block 542, and patient records indicate that benzodiazepine is not prescribed (Block 548), then it is determined that there is a discrepant result consistent with clorazepate (TRANXENE®) or chlordiazepoxide (LIBRIUM®) use (Block 550). If the test for temazepam is positive in Block 552, and patient records indicate that benzodiazepine is prescribed (Block 554), the results are considered consistent with diazepam (VALIUM®) use (Block 556). If, however, the temazepam test is positive in Block 552, and patient records indicate that benzodiazepine is not prescribed (Block 558), then it is determined that there is a discrepant result consistent with diazepam (VALIUM®) use (Block 560). If the test for oxazepam is negative in Block 562, then the presence of nordiazepam is determined in Block 564 (FIG. 16D). If the test for nordiazepam is negative in Block 566, then the presence of temazepam is determined in Block 568. If the test for temazepam is negative in Block 570, and patient records indicate that benzodiazepine is prescribed (Block 572), there is no comment in Block 574. Likewise, if the temazepam test is negative in Block 570, and patient records indicate that benzodiazepine is not prescribed (Block 576), there is no comment in Block 578. If the test for temazepam is positive in Block 580, and patient records indicate that benzodiazepine is prescribed (Block 582), the results are considered consistent with tenazepam (RESTORIL®) use (Block 584). If, however, the temazepam test is positive in Block 580, and patient records indicate that benzodiazepine is not prescribed (Block 586), then it is determined that there is a discrepant result consistent with tenazepam (RESTORIL®) use (Block 588). In contrast, if the test for nordiazepam is positive in Block 590, then the presence of temazepam is determined in Block 592. If the test for temazepam is negative in Block 594, and patient records indicate that benzodiazepine is prescribed (Block 596), the results are considered consistent with clorazepate (TRANXENE®) or chlordiazepoxide (LIBRIUM®) use (Block 598). If, however, the temazepam test is negative in Block 594, and patient records indicate that benzodiazepine is not prescribed (Block 600), then it is determined that there is a discrepant result consistent with clorazepate (TRANXENE®) or chlordiazepoxide (LIBRIUM®) use (Block 602). If the test for temazepam is positive in Block 604, and patient records indicate that benzodiazepine is prescribed (Block 606), the results are considered consistent with diazepam (VALIUM®) use (Block 608). If, however, the temazepam test is positive in Block 604, and patient records indicate that benzodiazepine is not prescribed (Block 610), then it is determined that there is a discrepant result consistent with diazepam (VALIUM®) use (Block 612).

FIG. 16E illustrates a medication/drug interpretation flow chart for flurazepam 614, in which prescription information has been considered. If the test for flurazepam is positive in Block 616, and patient records indicate that benzodiazepine is prescribed at Block 618, the results are considered consistent with flurazepam (DALMANE®) use (Block 620). If the test for flurazepam is positive in Block 616, and patient records indicate that benzodiazepine is not prescribed at Block 622, then it is determined that there is a discrepant result because flurazepam (DALMANE®) should be negative (Block 624). If, however, the test for flurazepam is negative in Block 626, then there is no comment in Block 628.

Figure 16F:
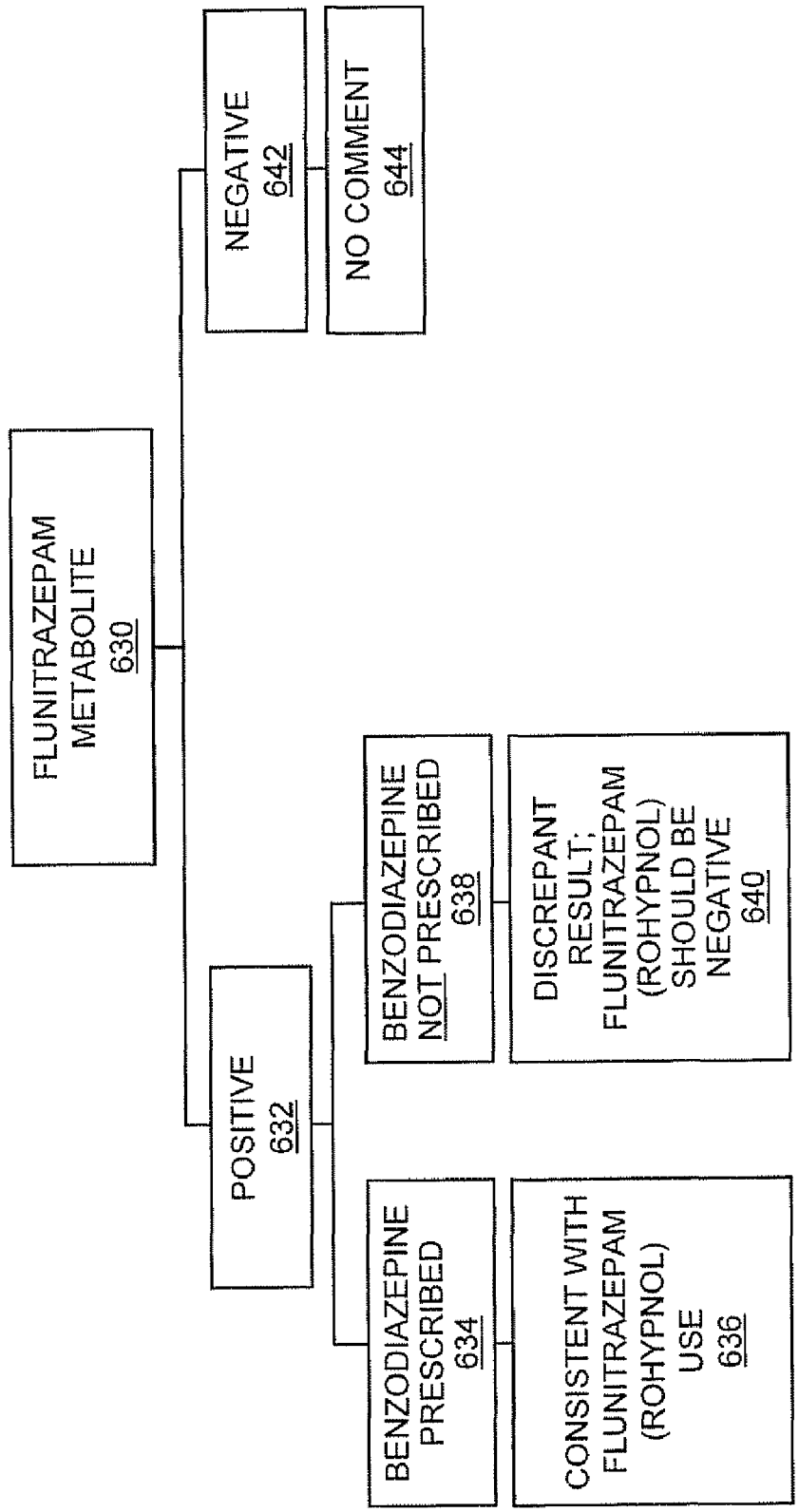

FIG. 16F illustrates a medication/drug interpretation flow chart for flunitrazepam 630, in which prescription information has been considered. If the test for flunitrazepam is positive in Block 632, and patient records indicate that benzodiazepine is prescribed at Block 634, the results are considered consistent with flunitrazepam (Rohypnol) use (Block 636). If the test for flunitrazepam is positive in Block 632, and patient records indicate that benzodiazepine is not prescribed at Block 638, then it is determined that there is a discrepant result because flunitrazepam (Rohypnol) should be negative (Block 640). If, however, the test for flunitrazepam is negative in Block 642, then there is no comment in Block 644.

Figure 16G:
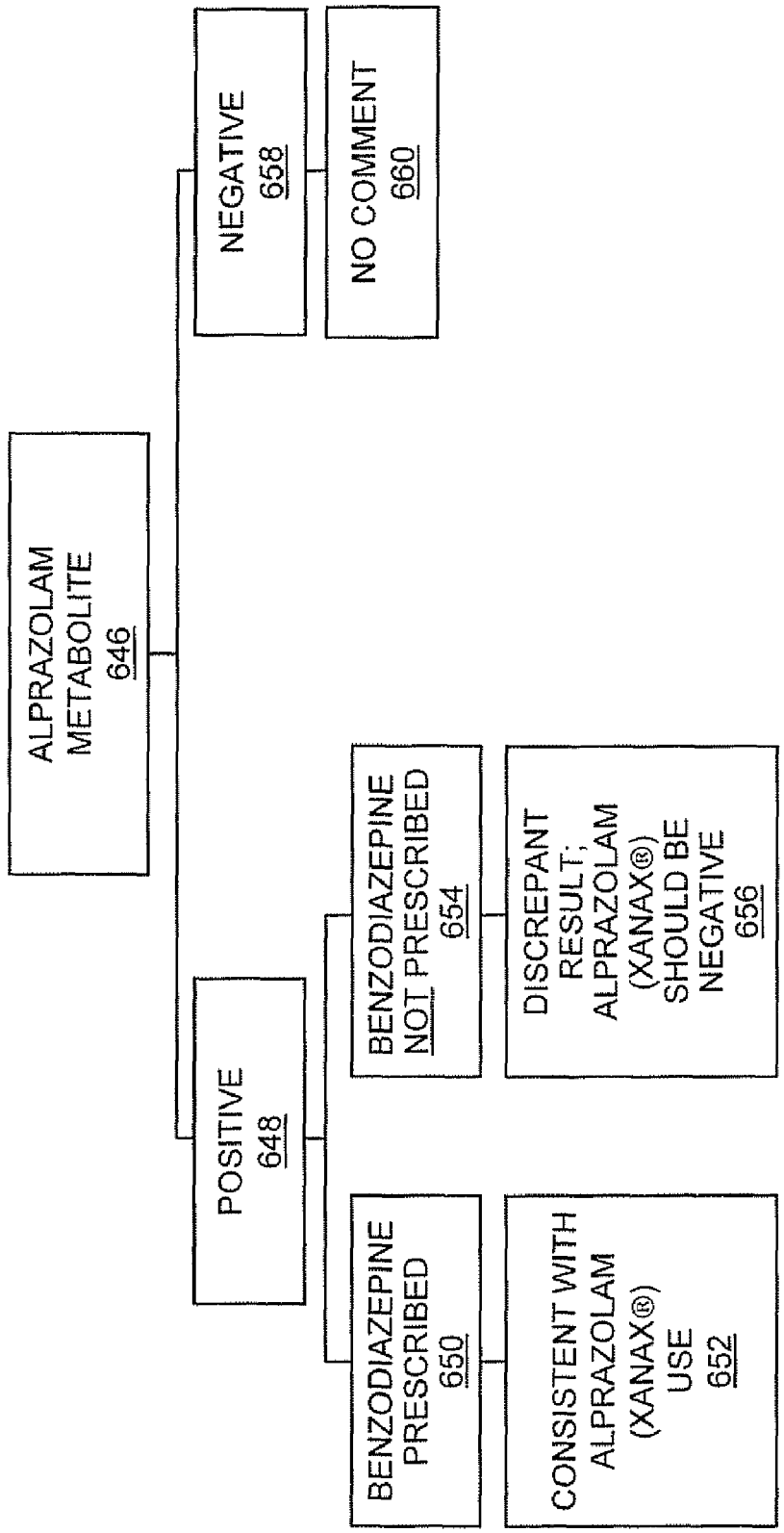

FIG. 16G illustrates a medication/drug interpretation flow chart for alprazolam 646, in which prescription information has been considered. If the test for alprazolam is positive in Block 648, and patient records indicate that benzodiazepine is prescribed at Block 650, the results are considered consistent with alprazolam (XANAX®) use (Block 652). If the test for alprazolam is positive in Block 648, and patient records indicate that benzodiazepine is not prescribed at Block 654, then it is determined that there is a discrepant result because alprazolam (XANAX®) should be negative (Block 656). If, however, the test for alprazolam is negative in Block 658, then there is no comment in Block 660.

Figure 16H:
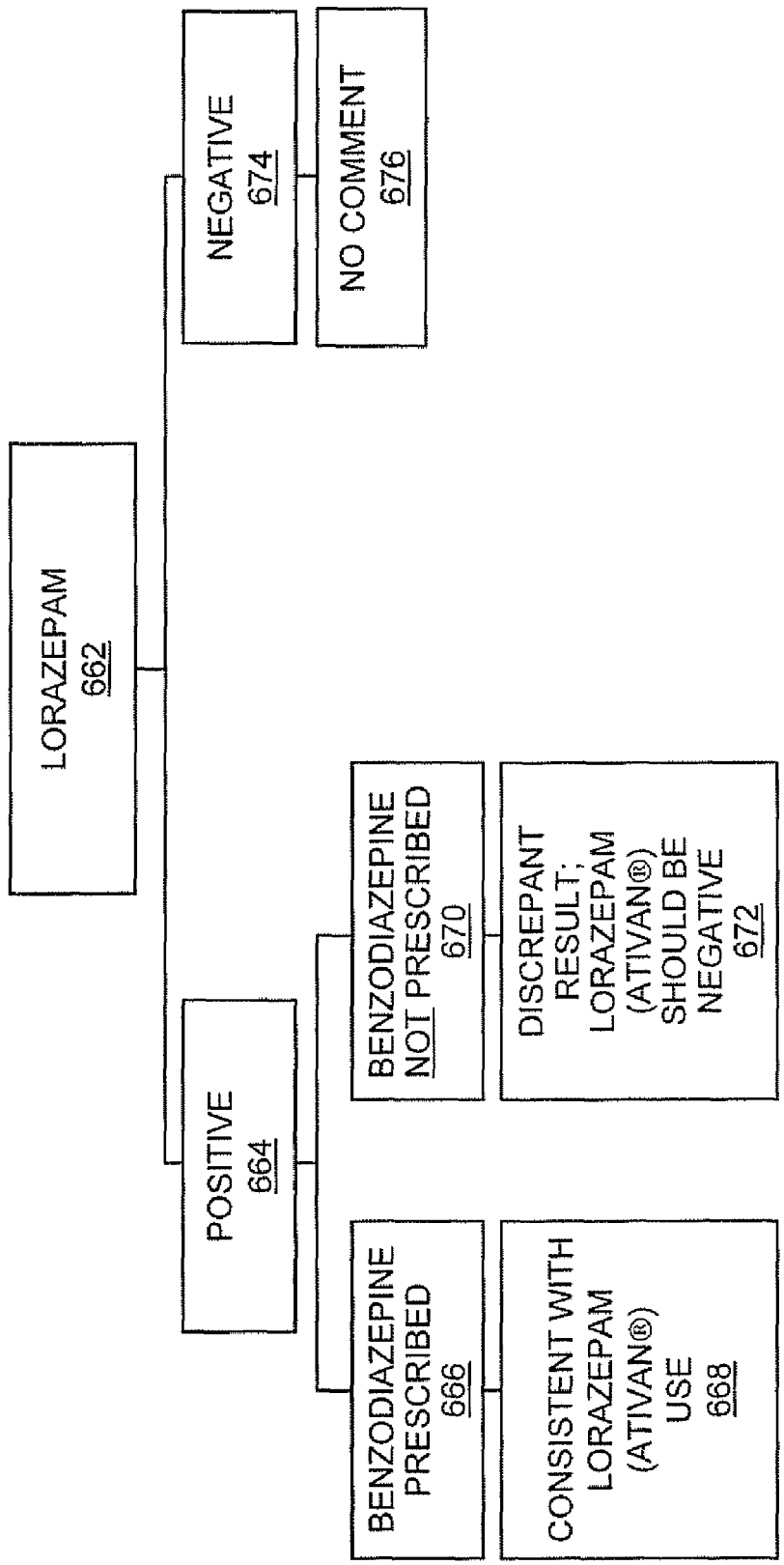

FIG. 16H illustrates a medication/drug interpretation flow chart for lorazepam 662, in which prescription information has been considered. If the test for lorazepam is positive in Block 664, and patient records indicate that benzodiazepine is prescribed at Block 666, the results are considered consistent with lorazepam (ATIVAN®) use (Block 668). If the test for lorazepam is positive in Block 664, and patient records indicate that benzodiazepine is not prescribed at Block 670, then it is determined that there is a discrepant result because lorazepam (ATIVAN®) should be negative (Block 672). If, however, the test for lorazepam is negative in Block 674, then there is no comment in Block 676.

Figure 16I:
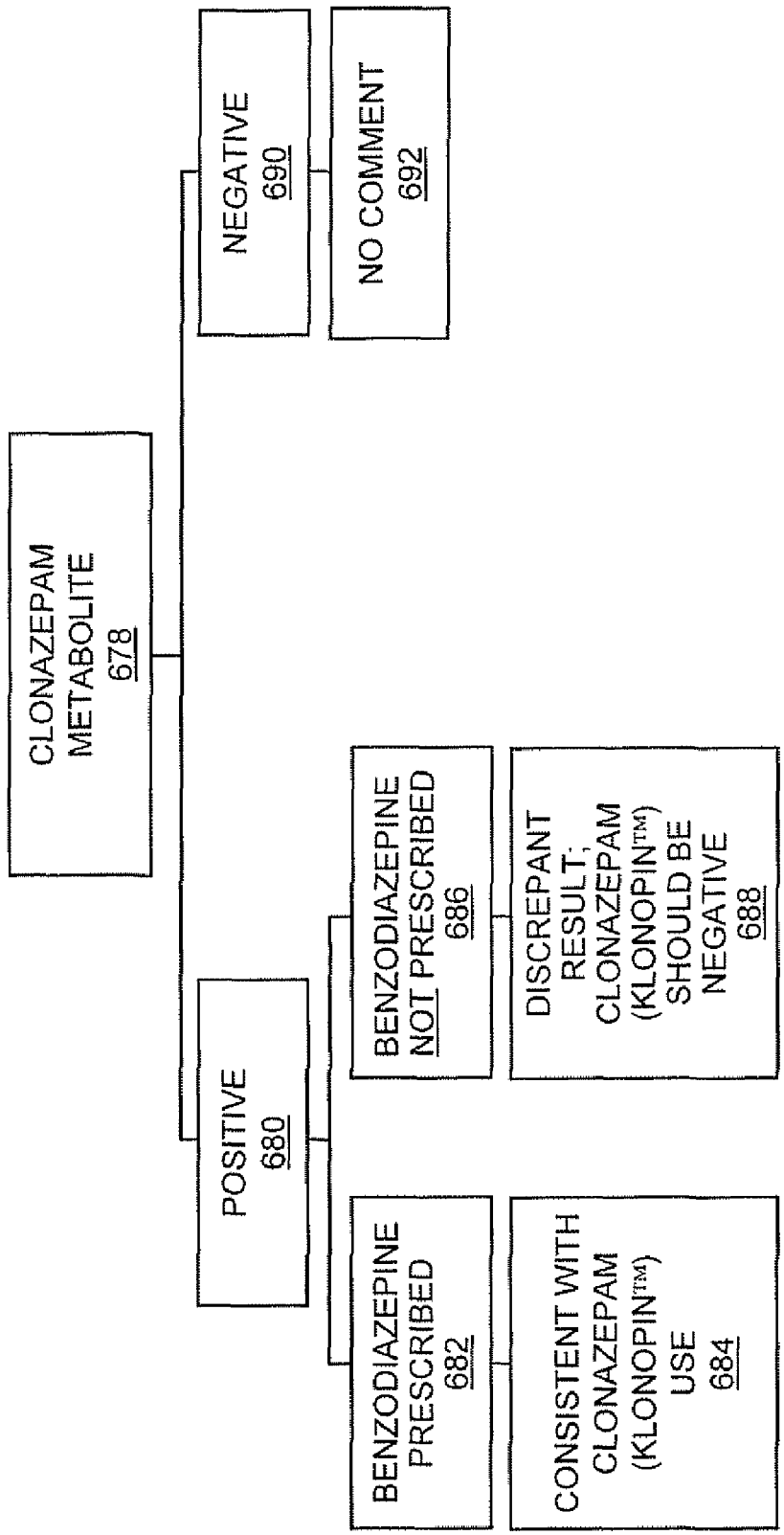

FIG. 16I provides a medication/drug interpretation flow chart for clonazepam 678, in which prescription information has been considered. If the test for clonazepam is positive in Block 680, and patient records indicate that benzodiazepine is prescribed at Block 682, the results are considered consistent with clonazepam (KLONOPIN™) use (Block 684). If the test for clonazepam is positive in Block 680, and patient records indicate that benzodiazepine is not prescribed at Block 686, then it is determined that there is a discrepant result because clonazepam (KLONOPIN™) should be negative (Block 688). If, however, the test for clonazepam is negative in Block 690, then there is no comment in Block 692.

Figure 17:
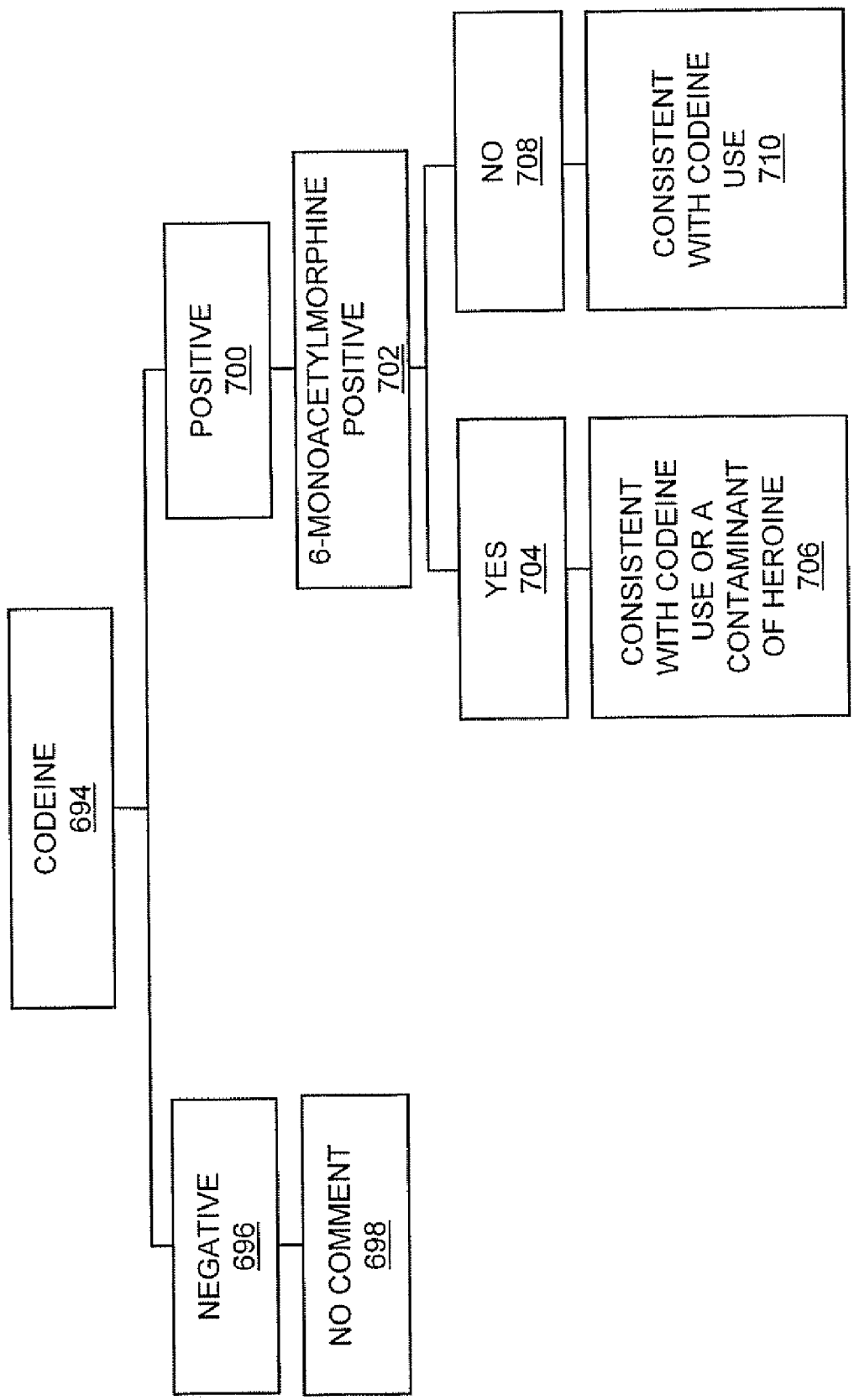
FIG. 17 is a block diagram of a medication/drug interpretation flow chart for codeine, in which prescription information has not been considered according to some embodiments of the present invention.

FIG. 17 illustrates a medication/drug interpretation flow chart for codeine 694, in which prescription information has not been considered. If the test for codeine is negative at Block 696, then there is no comment in Block 698. If, however, the test for codeine is positive in Block 700, then it is determined whether 6-monoacetylmorphine is present at Block 702. If 6-monoacetylmorphine is positive at Block 704, the result is considered consistent with either codeine use or a contaminant of heroine (Block 706). If 6-monoacetylmorphine is negative at Block 708, the results are considered consistent with codeine use (Block 710).

Figure 18:
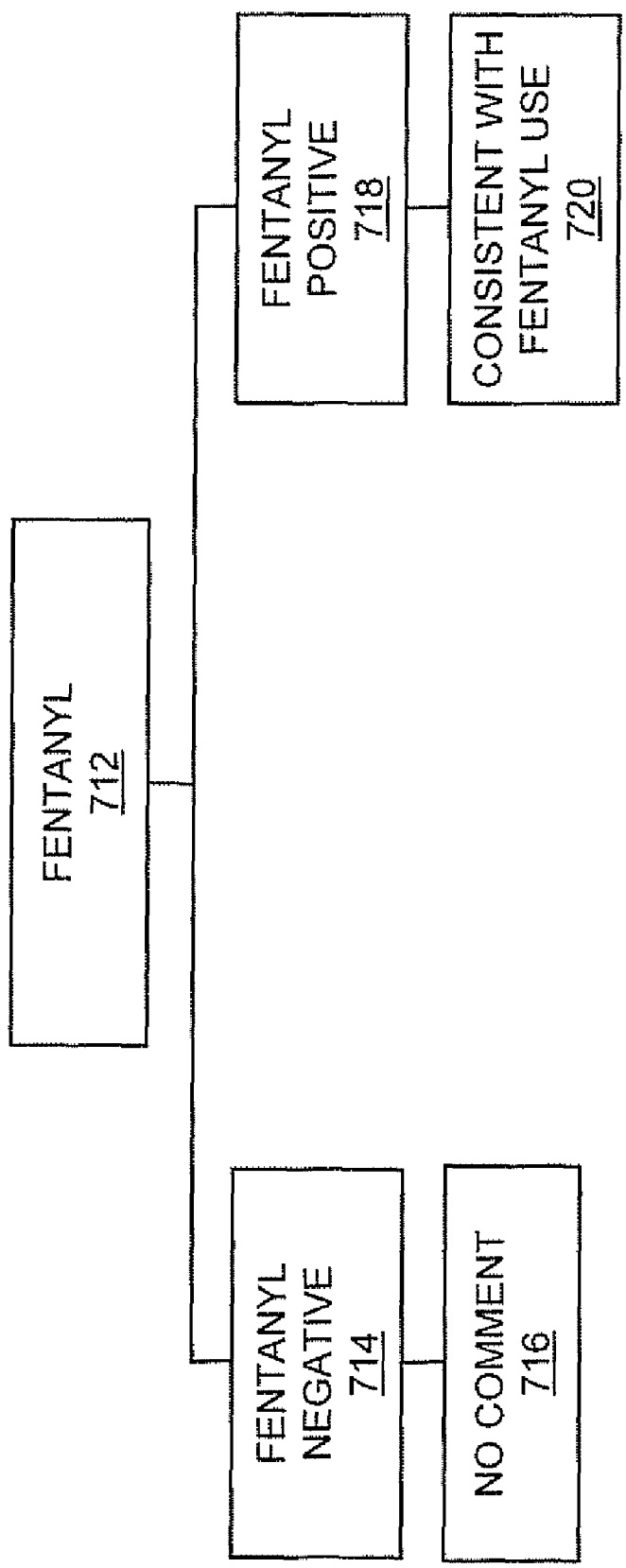
FIG. 18 is a block diagram of a medication/drug interpretation flow chart for fentanyl, in which prescription information has not been considered according to some embodiments of the present invention.

A medication/drug interpretation flow chart for fentanyl 712, in which prescription information has not been considered, is provided in FIG. 18. If the test for fentanyl is negative at Block 714, then there is no comment in Block 716. On the other hand, a positive fentanyl test result at Block 718 is considered consistent with fentanyl use (Block 720).

Figure 19:
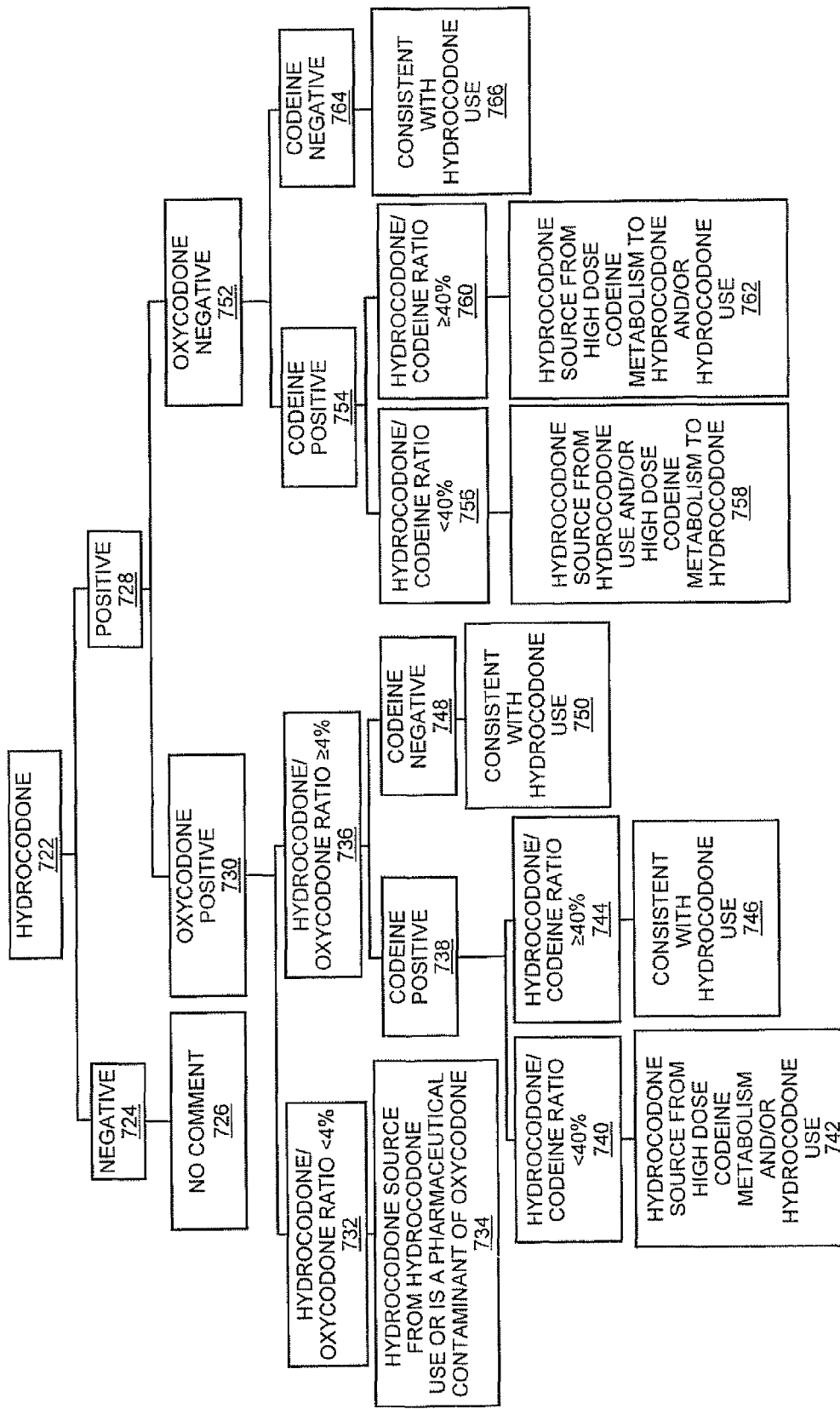
FIG. 19 is a block diagram of a medication/drug interpretation flow chart for hydrocodone, in which prescription information has not been considered according to some embodiments of the present invention.

A medication/drug interpretation flow chart for hydrocodone 722, in which prescription information has not been considered, is provided in FIG. 19. If the test for hydrocodone is negative in Block 724, then there is no comment in Block 726. If, however, the test for hydrocodone is positive in Block 728, then it is determined whether oxycodone is present. If the oxycodone test is positive at Block 730, then the ratio of hydrocodone/oxycodone is determined. If the hydrocodone/oxycodone ratio is <4% at Block 732, then it is determined that the hydrocodone source is from hydrocodone use or is a pharmaceutical contaminant of oxycodone at Block 734. If, however, the hydrocodone/oxycodone ratio is ≧4% at Block 736, then it is determined whether codeine is present. If the codeine test is positive at Block 738, then the ratio of hydrocodone/codeine is determined, in which a hydrocodone/codeine ratio of <40% at Block 740 indicates that the hydrocodone source is from high dose codeine metabolism and/or hydrocodone use (Block 742), whereas a hydrocodone/codeine ratio of ≧40% at Block 744 is considered consistent with hydrocodone use (Block 746). Likewise, if the codeine test is negative at Block 748, then the result is considered consistent with hydrocodone use (Block 750). A negative oxycodone result at Block 752 prompts a determination of whether codeine is present. If the codeine test is positive at Block 754, then the ratio of hydrocodone/codeine is determined, in which a hydrocodone/codeine ratio of <40% at Block 756 indicates that the hydrocodone source is from hydrocodone use and/or high dose codeine metabolism to hydrocodone (Block 758), whereas a hydrocodone/codeine ratio of ≧40% at Block 760 indicates that the hydrocodone source is from high dose codeine metabolism to hydrocodone and/or hydrocodone use (Block 762). If the codeine test is negative at Block 764, then the result is considered consistent with hydrocodone use (Block 766).

Figure 20A:
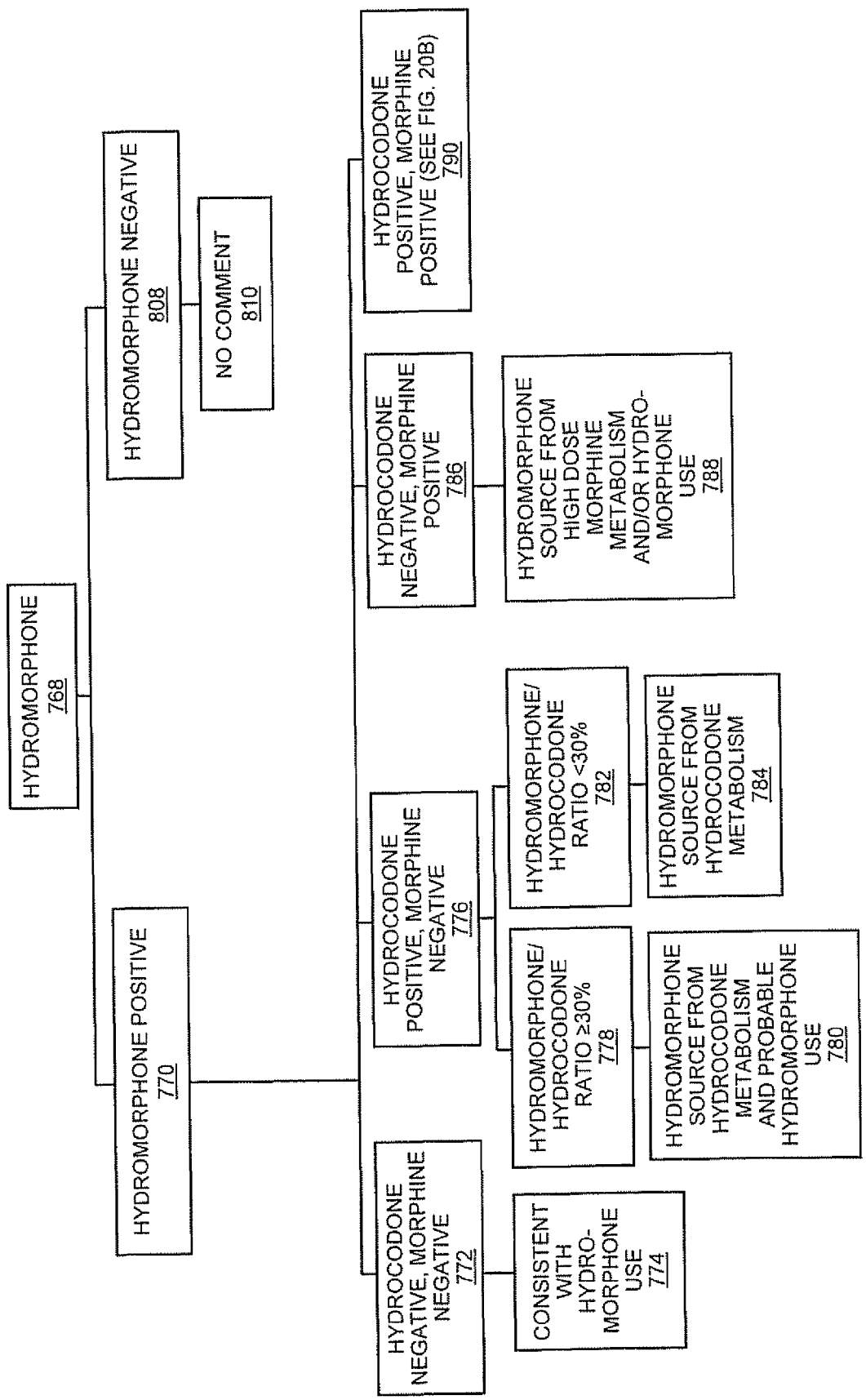
FIGS. 20A-20B are block diagrams of a medication/drug interpretation flow chart for hydromorphone, in which prescription information has not been considered according to some embodiments of the present invention.
Figure 20B:
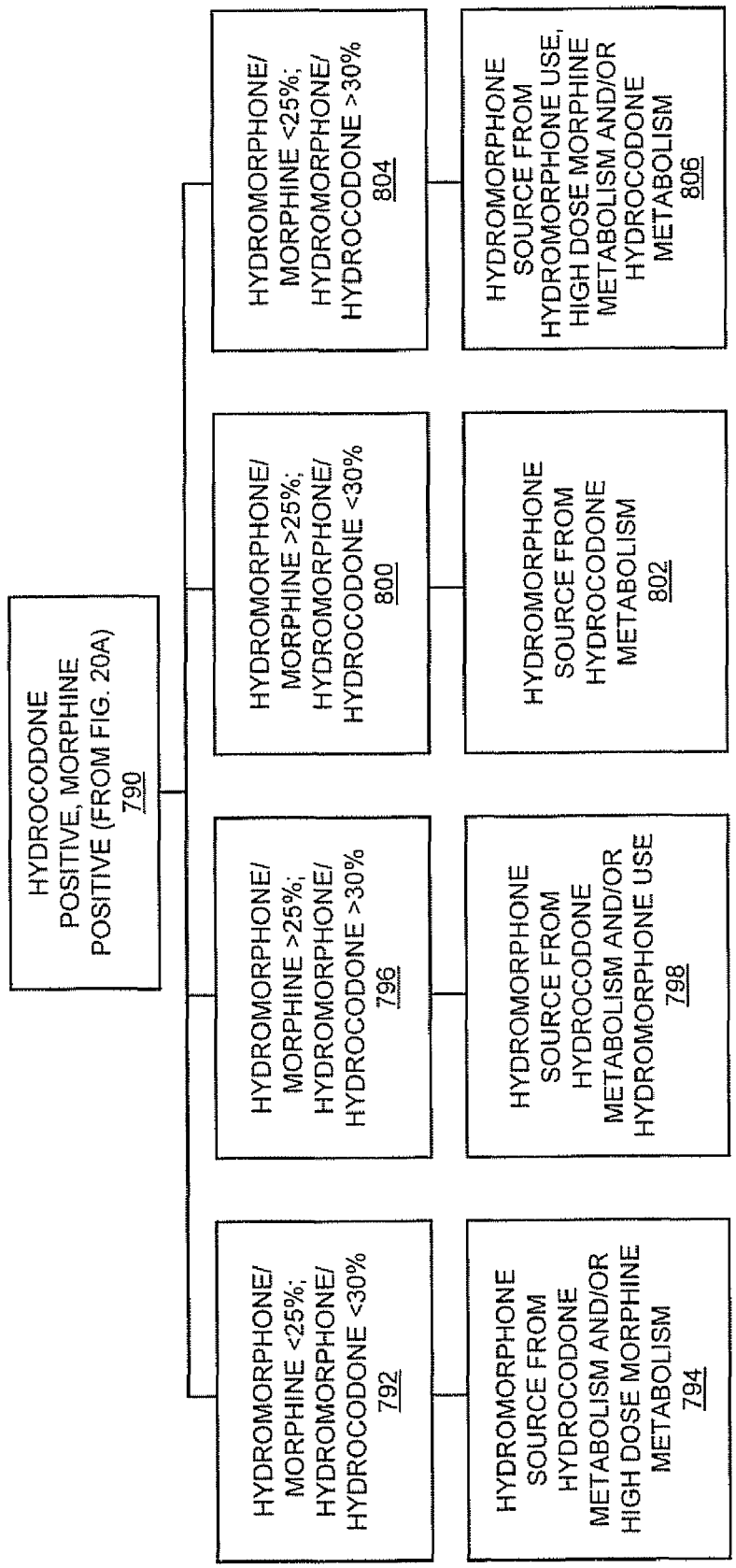

FIGS. 20A and 20B illustrate a medication/drug interpretation flow chart for hydromorphone 768, in which prescription information has not been considered. If the test for hydromorphone is positive at Block 770, then it is determined whether hydrocodone and/or morphine are present. Negative hydrocodone and negative morphine tests at Block 772 is considered consistent with hydromorphone use (Block 774). If the hydrocodone test is positive and the morphine test is negative (Block 776), the ratio of hydromorphone/hydrocodone is determined, in which a hydromorphone/hydrocodone ratio of ≧30% at Block 778 indicates that the hydromorphone source is from hydrocodone metabolism and probable hydromorphone use (Block 780), whereas a hydromorphone/hydrocodone ratio of <30% at Block 782 indicates that the hydromorphone source is from hydrocodone metabolism (Block 784). A negative hydrocodone test and positive morphine test at Block 786 indicates that the hydromorphone source is from high dose morphine metabolism and/or hydromorphone use (Block 788). When both hydrocodone and morphine tests are positive at Block 790, then hydromorphone/morphine and hydromorphone/hydrocodone ratios are determined in FIG. 20B. With continued reference to FIG. 20B, hydromorphone/morphine ratio of <25% and hydromorphone/hydrocodone ratio of <30% (Block 792) indicates that the hydromorphone source is from hydrocodone metabolism and/or high dose morphine metabolism (Block 794). A hydromorphone/morphine ratio of >25% and hydromorphone/hydrocodone ratio of >30% (Block 796) indicates that the hydromorphone source is from hydrocodone metabolism and/or hydromorphone use (Block 798). A hydromorphone/morphine ratio of >25% and hydromorphone/hydrocodone ratio of <30% (Block 800) indicates that the hydromorphone source is from hydrocodone metabolism (Block 802). A hydromorphone/morphine ratio of <25% and hydromorphone/hydrocodone ratio of >30% (Block 804) indicates that the hydromorphone source is from hydromorphone use, high dose morphine metabolism and/or hydrocodone metabolism (Block 806). In contrast, when the hydromorphone test is negative in Block 808, there is no comment in Block 810.

Figure 21:
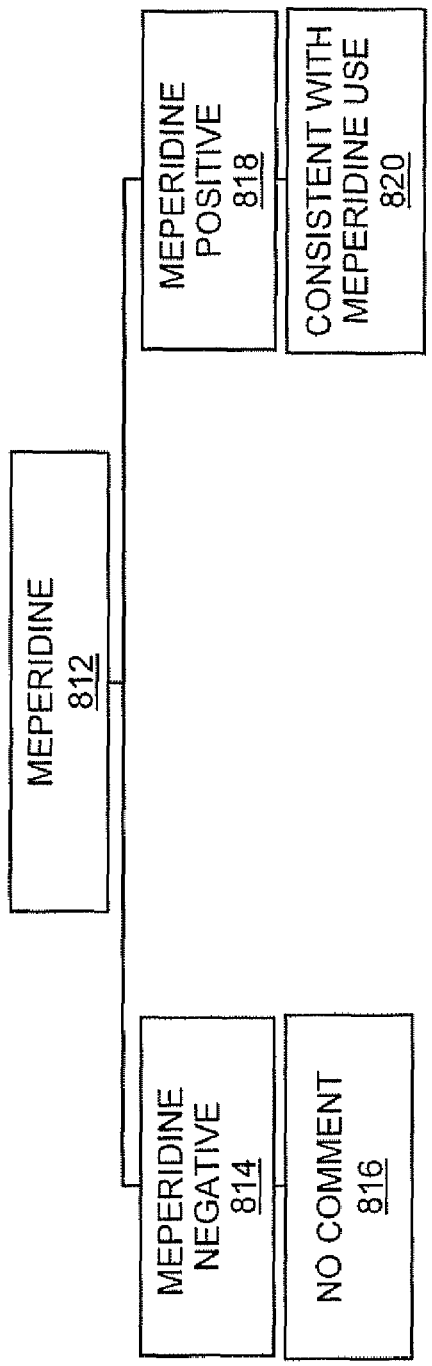
FIG. 21 is a block diagram of a medication/drug interpretation flow chart for meperidine, in which prescription information has not been considered according to some embodiments of the present invention.

FIG. 21 illustrates a medication/drug interpretation flow chart for meperidine 812, in which prescription information has not been considered. If the test for meperidine is negative at Block 814, then there is no comment in Block 816. In contrast, a positive meperidine test result at Block 818 is consistent with meperidine use (Block 820).

Figure 22:
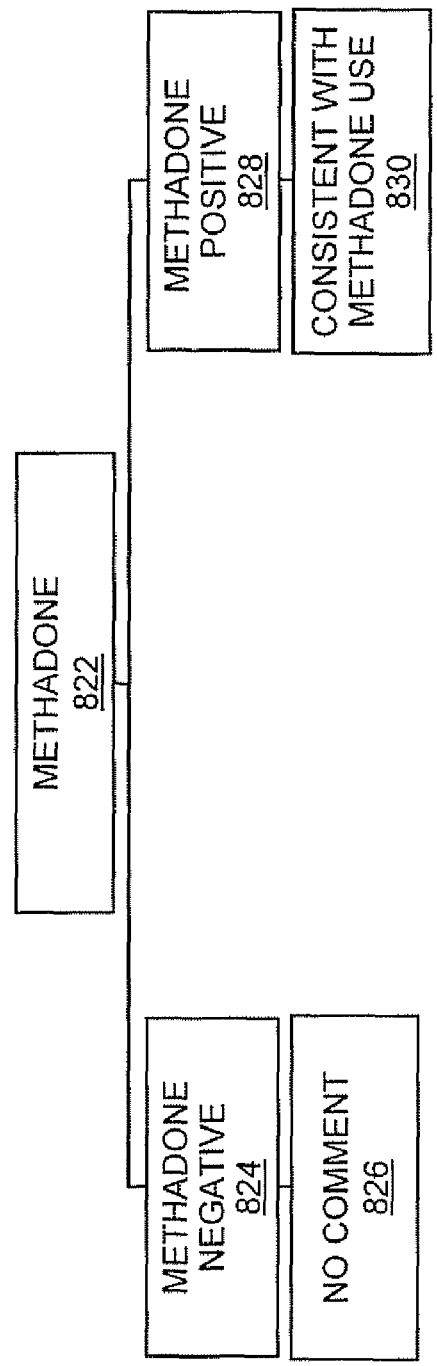
FIG. 22 is a block diagram of a medication/drug interpretation flow chart for methadone, in which prescription information has not been considered according to some embodiments of the present invention.

FIG. 22 illustrates a medication/drug interpretation flow chart for methadone 822, in which prescription information has not been considered. If the test for methadone is negative at Block 824, then there is no comment in Block 826. In contrast, a positive methadone test result at Block 828 is consistent with methadone use (Block 830).

Figure 23:
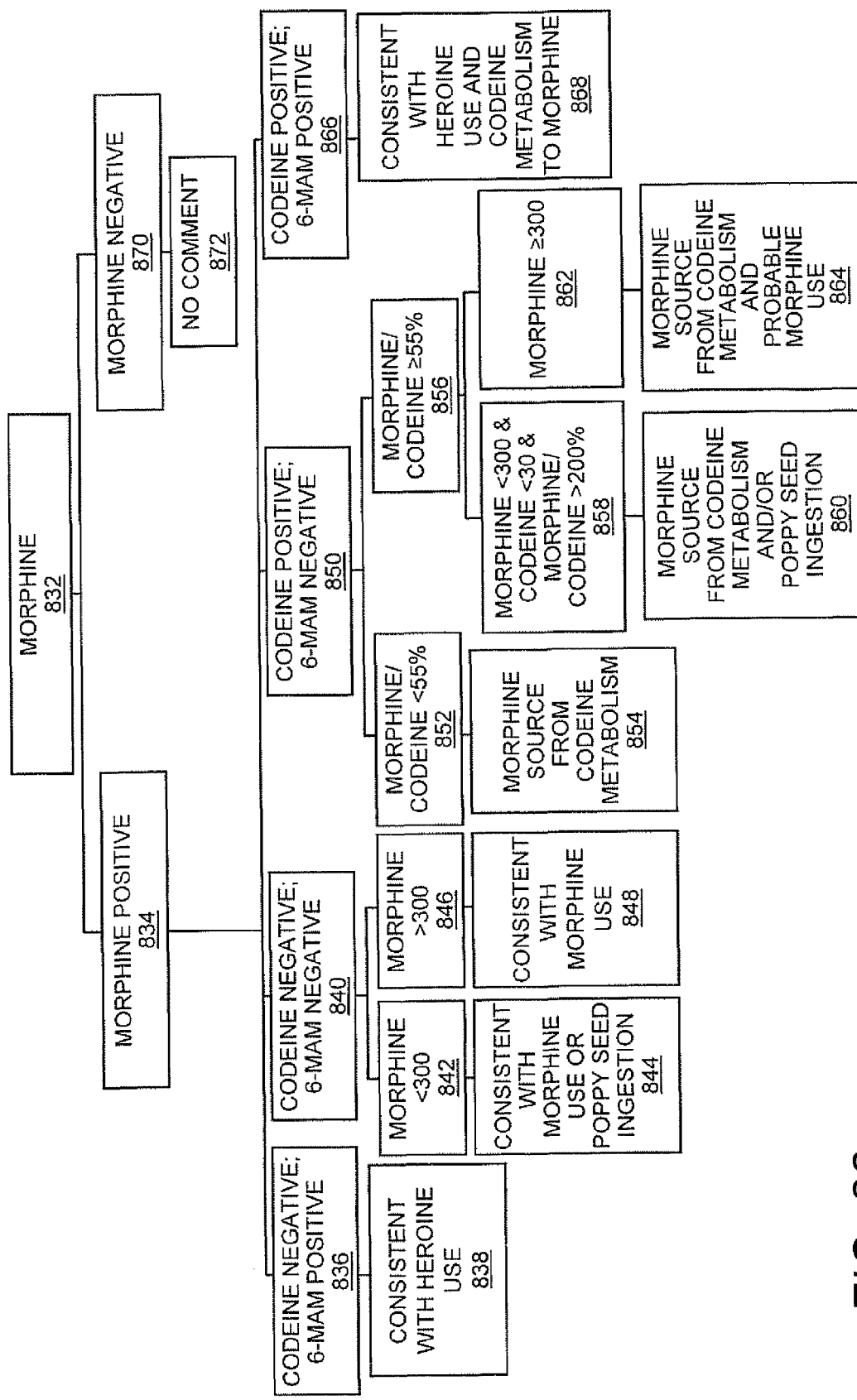
FIG. 23 is a block diagram of a medication/drug interpretation flow chart for morphine, in which prescription information has not been considered according to some embodiments of the present invention.

FIG. 23 provides a medication/drug interpretation flow chart for morphine 832, in which prescription information has not been considered. If the test for morphine is positive in Block 834, then it is determined whether codeine and/or 6-MAM are present. A negative codeine test and positive 6-MAM test at Block 836 is consistent with heroine use (Block 838). When both codeine and 6-MAM tests are negative at Block 840, then the level of morphine is considered, in which levels <300 ng/ml (Block 842) are consistent with morphine use or poppy seed ingestion (Block 844) and levels >300 ng/ml (Block 846) are consistent with morphine use (Block 848). If the codeine test is positive and the 6-MAM test is negative (Block 850), then morphine/codeine ratios are determined. A morphine/codeine ratio <55% at Block 852 indicates that the morphine source is from codeine metabolism (Block 854), whereas a morphine/codeine ratio ≧55% at Block 856 prompts the determination of morphine and codeine levels, in which morphine levels <300 ng/ml, codeine levels <30 ng/ml, and a morphine/codeine ratio of >200% (Block 858) indicates that the morphine source is from codeine metabolism and/or poppy seed ingestion (Block 860) and levels of morphine >300 ng/ml (Block 862) indicate that the morphine source is from codeine metabolism and probable morphine use (Block 864). When both the codeine test and 6-MAM test are positive at Block 866, the results are determined to be consistent with heroine use and codeine metabolism to morphine (Block 868). If, however, the test for morphine is negative at Block 870, then there is no comment in Block 872.

Figure 24:
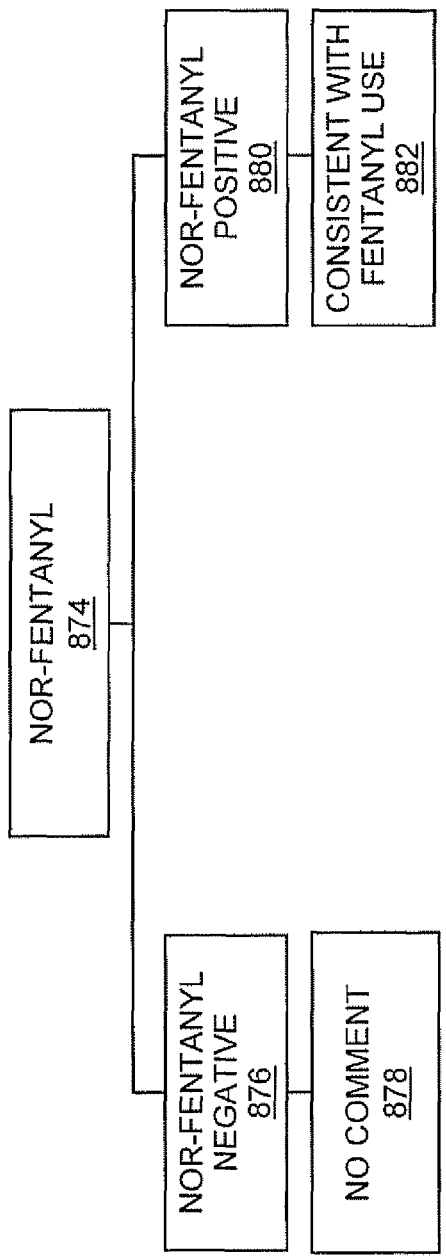
FIG. 24 is a block diagram of a medication/drug interpretation flow chart for nor-fentanyl, in which prescription information has not been considered according to some embodiments of the present invention.

FIG. 24 illustrates a medication/drug interpretation flow chart for nor-fentanyl 874, in which prescription information has not been considered. If the test for nor-fentanyl is negative at Block 876, then there is no comment in Block 878. In contrast, a positive nor-fentanyl test result at Block 880 is consistent with fentanyl use (Block 882).

Figure 25:
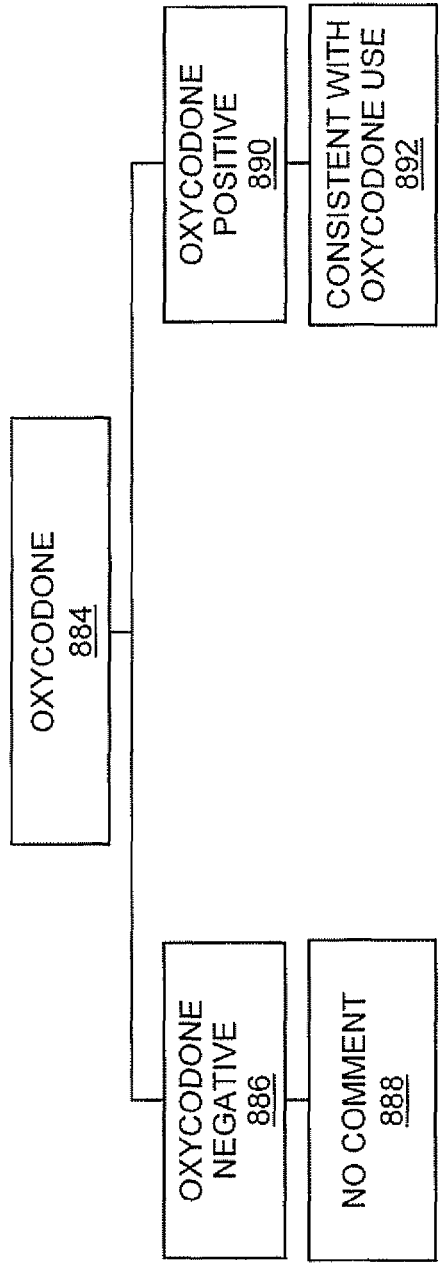
FIG. 25 is a block diagram of a medication/drug interpretation flow chart for oxycodone, in which prescription information has not been considered according to some embodiments of the present invention.

FIG. 25 illustrates a medication/drug interpretation flow chart for oxycodone 884, in which prescription information has not been considered. If the test for oxycodone is negative at Block 886, then there is no comment in Block 888. In contrast, a positive oxycodone test result at Block 890 is consistent with oxycodone use (Block 892).

Figure 26:
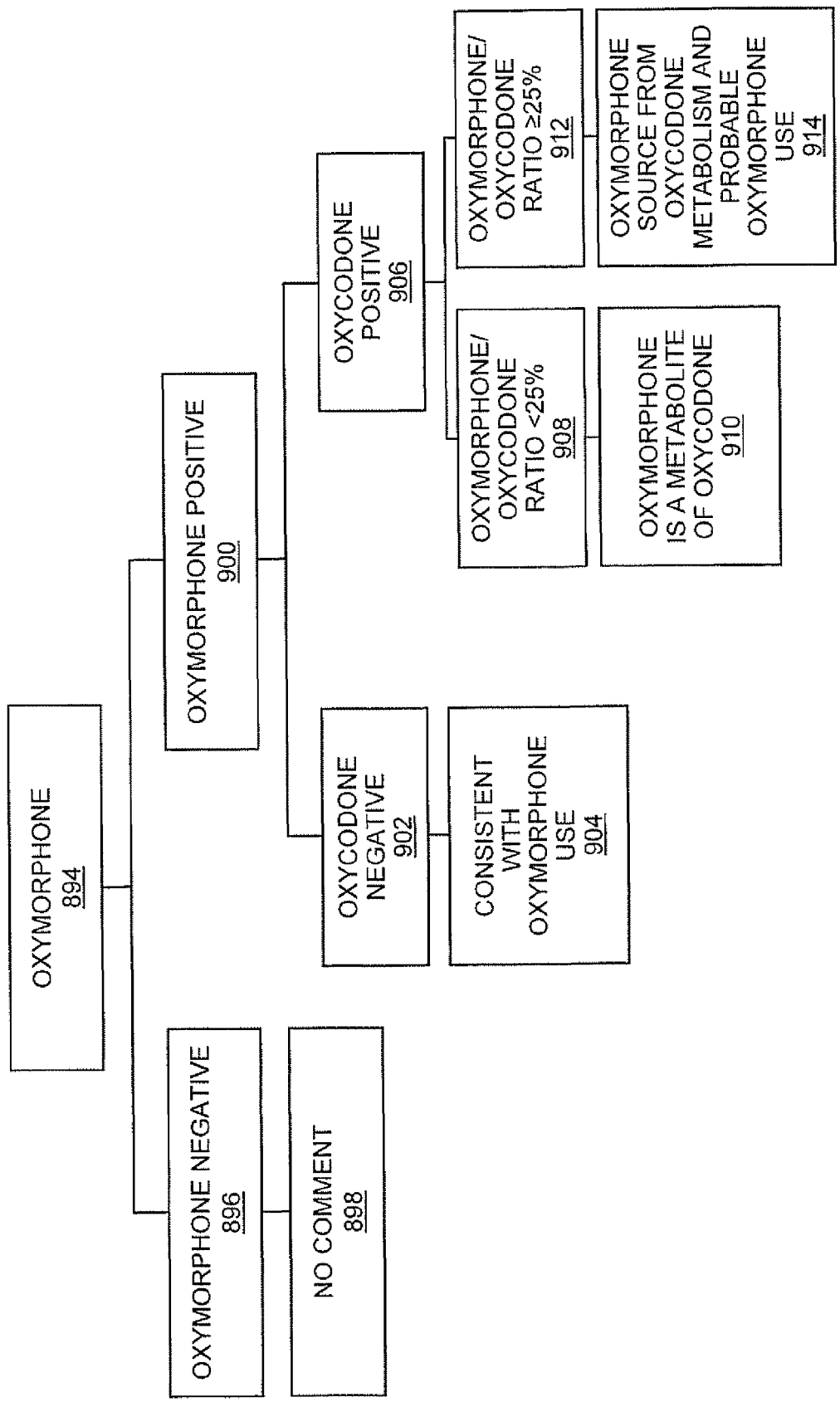
FIG. 26 is a block diagram of a medication/drug interpretation flow chart for oxymorphone, in which prescription information has not been considered according to some embodiments of the present invention.

A medication/drug interpretation flow chart for oxymorphone 894, in which prescription information has not been considered, is provided in FIG. 26. If the test for oxymorphone is negative at Block 896, then there is no comment in Block 898. If, however, the test for oxymorphone is positive at Block 900, then the presence of oxycodone is determined. A negative oxycodone test result at Block 902, is consistent with oxymorphone use (Block 904). If, however, the oxycodone test is positive at Block 906, then the oxymorphone/oxycodone ratio is determined. When the oxymorphone/oxycodone ratio is <25% (Block 908), then the presence of oxymorphone is considered a metabolite of oxycodone (Block 910). If the oxymorphone/oxycodone ratio is ≧25% (Block 912), then the oxymorphone source is from oxycodone metabolism and probable oxymorphone use (Block 914).

Figure 27:
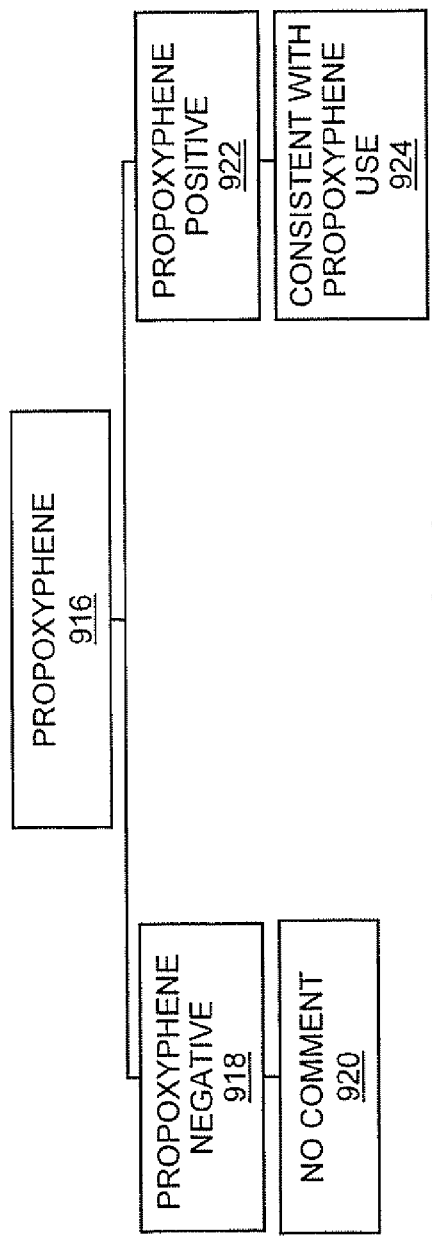
FIG. 27 is a block diagram of a medication/drug interpretation flow chart for propoxyphene, in which prescription information has not been considered according to some embodiments of the present invention.

FIG. 27 illustrates a medication/drug interpretation flow chart for propoxyphene 916, in which prescription information has not been considered. If the test for propoxyphene is negative at Block 918, then there is no comment in Block 920. In contrast, a positive propoxyphene test result at Block 922 is consistent with propoxyphene use (Block 924).

Figure 28A:
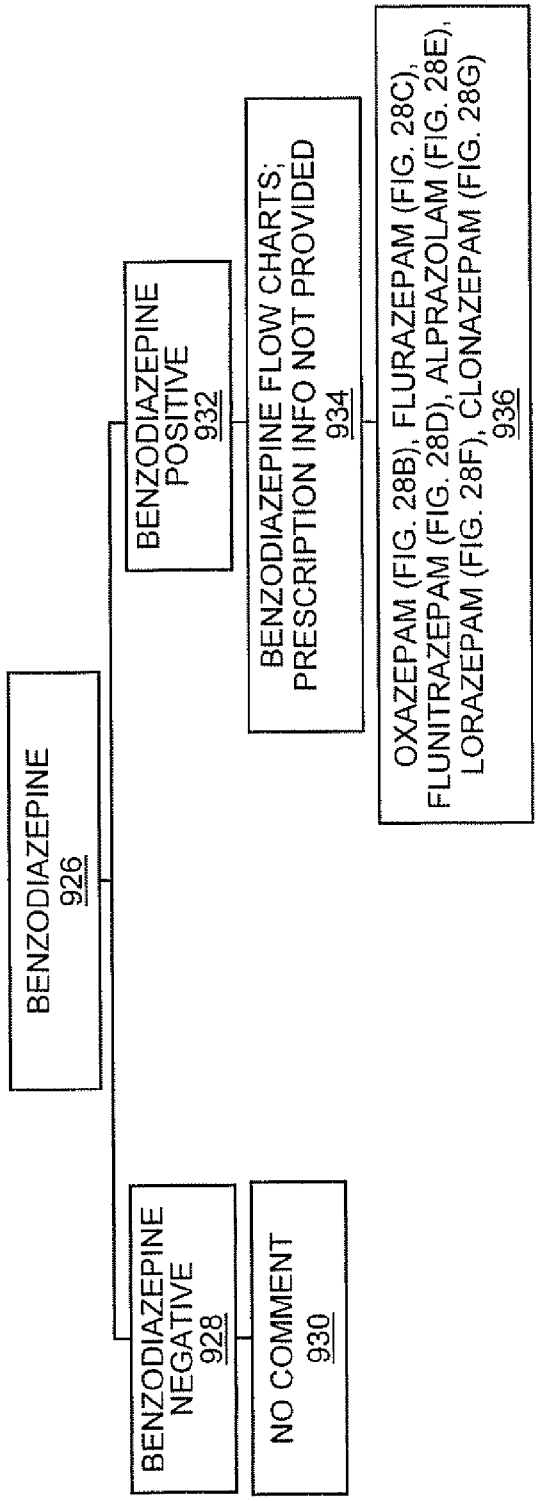
FIGS. 28A-28G are a block diagrams of a medication/drug interpretation flow chart for benzodiazepine (FIG. 28A) and benzodiazepine derivatives oxazepam (FIG. 28B), flurazepam (FIG. 28C), flunitrazepam (FIG. 28D), alprazolam (FIG. 28E), lorazepam (FIG. 28F), and clonazepam (FIG. 28G), in which prescription information has not been considered according to some embodiments of the present invention.

FIG. 28A illustrates a medication/drug interpretation flow chart for benzodiazepine 926, in which prescription information has not been considered. If the test for benzodiazepine is negative at Block 928, then there is no comment at Block 930. If, however, the test for benzodiazepine is positive at Block 932, then the flowcharts for benzodiazepine derivatives are referenced in Block 934, with determinations for oxazepam (FIG. 28B), flurazepam (FIG. 28C), flunitrazepam (FIG. 28D), Alpraxolam (FIG. 28E), lorazepam (FIG. 28F) and clonazepam (FIG. 28G) being made in Block 936.

Figure 28B:
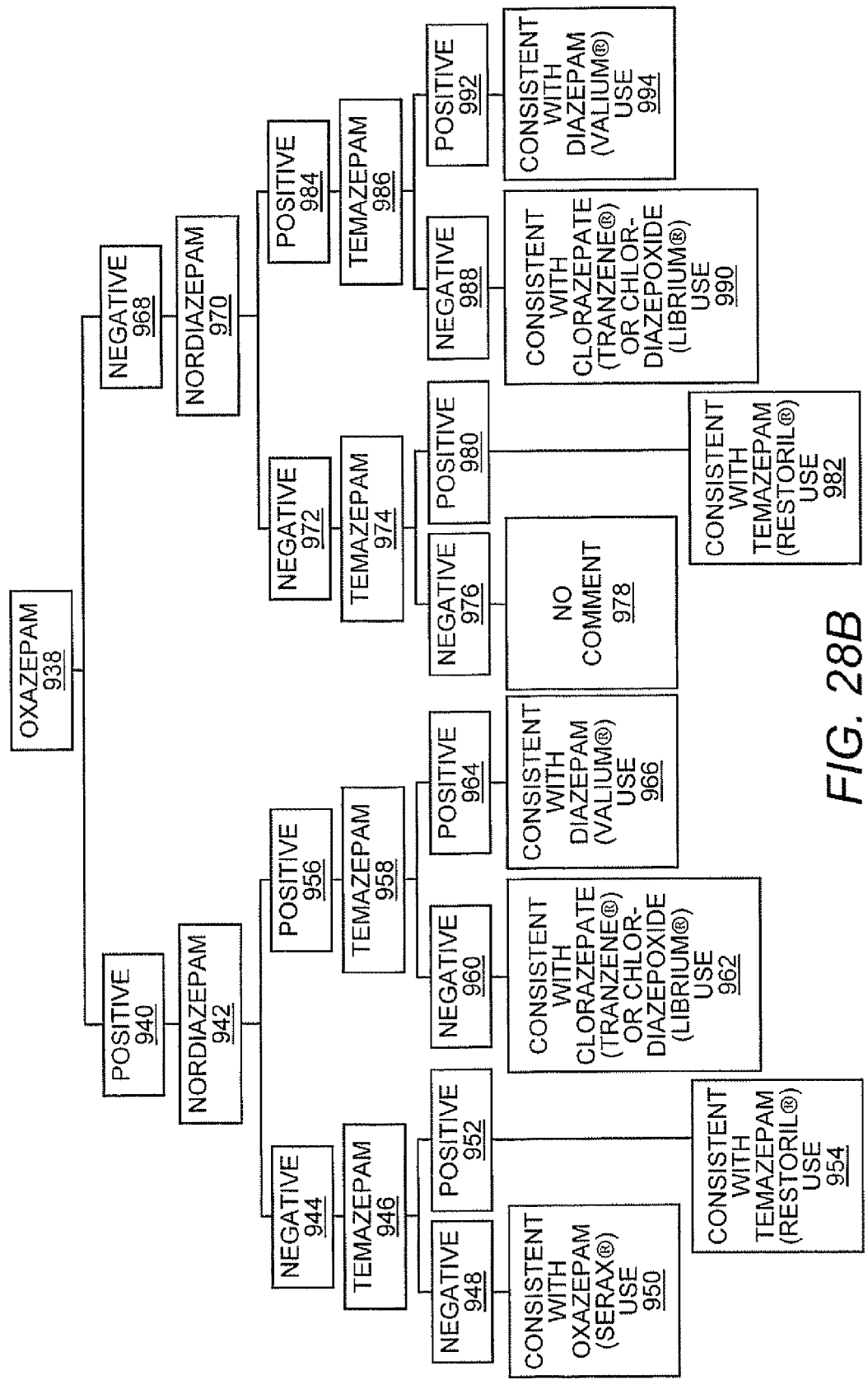

The pain management flow chart for oxazepam 938, in which prescription information has not been considered is illustrated in FIG. 28B. If the test for oxazepam is positive in Block 940, then the presence of nordiazepam is determined in Block 942. If the test for nordiazepam is negative in Block 944, then the presence of temazepam is determined in Block 946. If the test for temazepam is negative in Block 948, the results are considered consistent with oxazepam (SERAX®) use (Block 950). If, however, the temazepam test is positive in Block 952, the results are considered consistent with tenazepam (RESTORIL®) use (Block 954). In contrast, if the test for nordiazepam is positive in Block 956, then the presence of temazepam is determined in Block 958. If the test for temazepam is negative in Block 960, the results are considered consistent with clorazepate (TRANXENE®) or chlordiazepoxide (LIBRIUM®) use (Block 962). If, however, the temazepam test is positive in Block 964, the results are considered consistent with diazepam (VALIUM®) use (Block 966). If the test for oxazepam is negative in Block 968, then the presence of nordiazepam is determined in Block 970. If the test for nordiazepam is negative in Block 972, then the presence of temazepam is determined in Block 974. If the test for temazepam is negative in Block 976, then there is no comment in Block 978. If the test for temazepam is positive in Block 980, the results are considered consistent with temazepam (RESTORIL®) use (Block 982). In contrast, if the test for nordiazepam is positive in Block 984, then the presence of temazepam is determined in Block 986. If the test for temazepam is negative in Block 988, the results are considered consistent with clorazepate (TRANXENE®) or chlordiazepoxide (LIBRIUM®) use (Block 990). If the test for temazepam is positive in Block 992, then the results are considered consistent with diazepam (VALIUM®) use (Block 994).

Figure 28C:
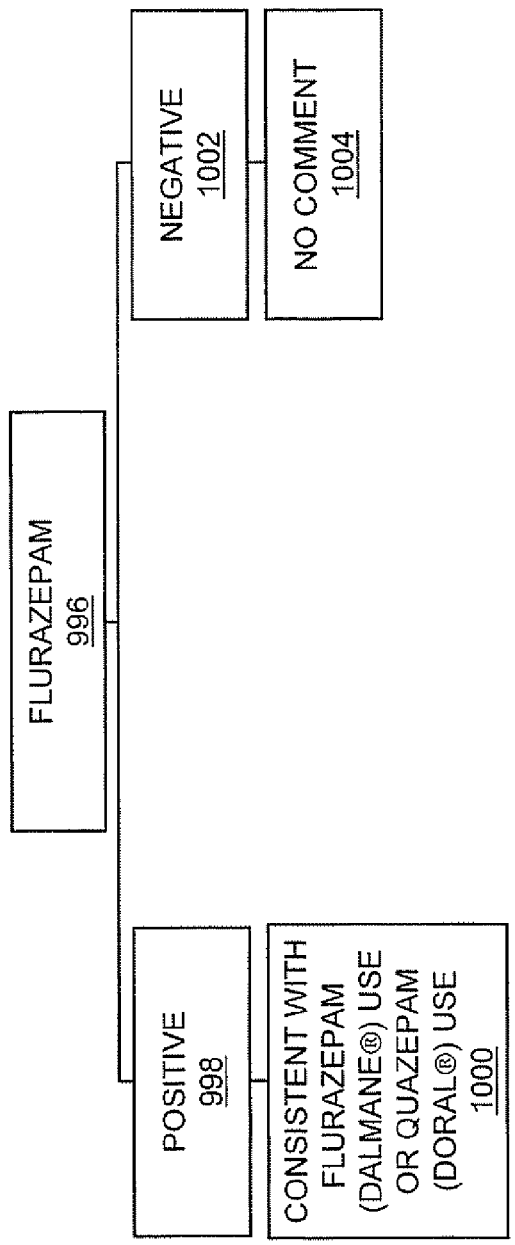

FIG. 28C illustrates a medication/drug interpretation flow chart for flurazepam 996, in which prescription information has not been considered. A positive flurazepam test result at Block 998 is considered consistent with flurazepam (DALMANE®) or quazepam (DORAL®) use (Block 1000). In contrast, if the flurazepam test result is negative at Block 1002, then there is no comment at Block 1004.

Figure 28D:
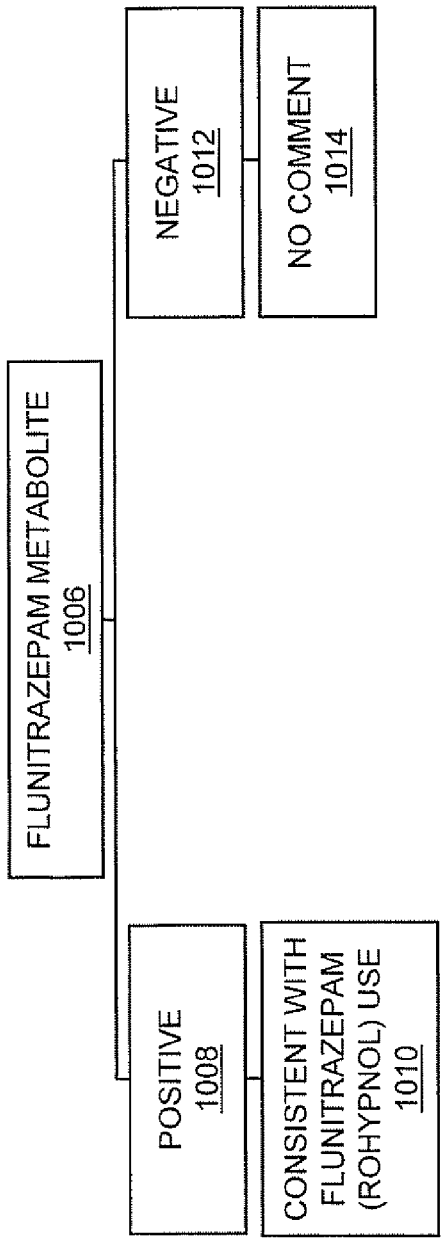

FIG. 28D illustrates a medication/drug interpretation flow chart for flunitrazepam 1006, in which prescription information has not been considered. A positive flunitrazepam test result at Block 1008 is considered consistent with flunitrazepam (Rohypnol) use (Block 1010). In contrast, if the flunitrazepam test result is negative at Block 1002, then there is no comment at Block 1014.

Figure 28E:
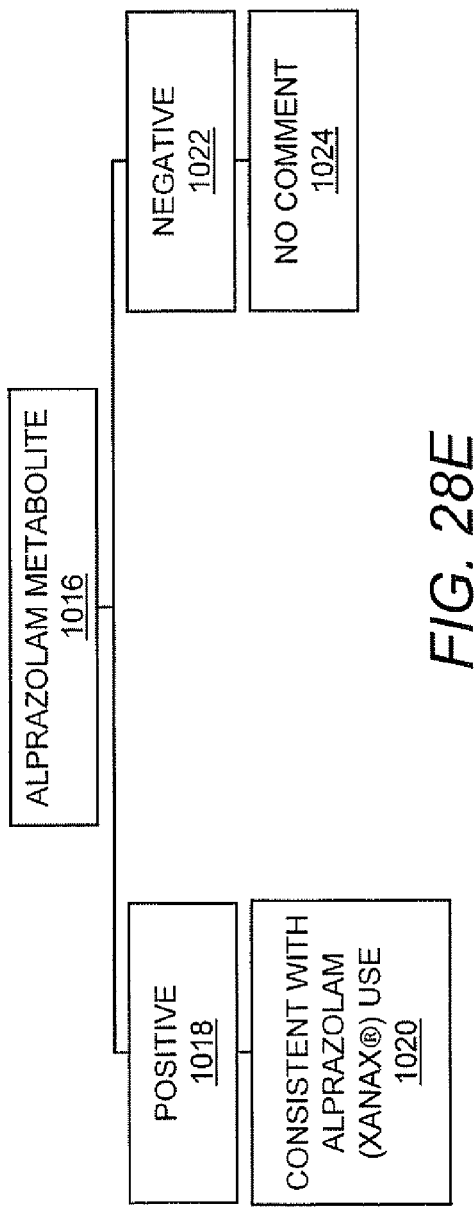

FIG. 28E illustrates a medication/drug interpretation flow chart for alprazolam 1016, in which prescription information has not been considered. A positive alprazolam test result at Block 1018 is considered consistent with alprazolam (XANAX®) use (Block 1020). In contrast, if the alprazolam test result is negative at Block 1022, then there is no comment at Block 1024.

Figure 28F:
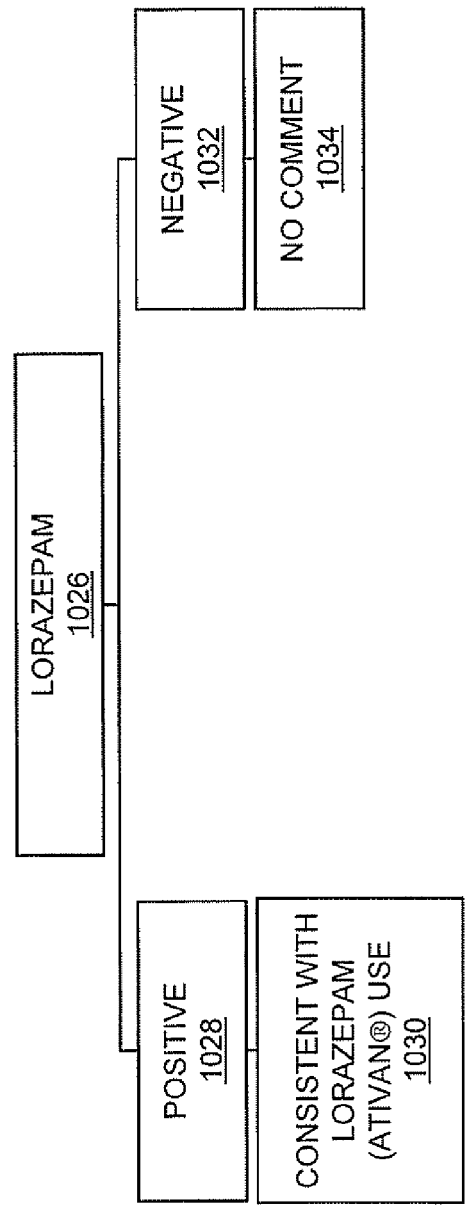

FIG. 28F illustrates a medication/drug interpretation flow chart for lorazepam 1026, in which prescription information has not been considered. A positive lorazepam test result at Block 1028 is considered consistent with lorazepam (ATIVAN®) use (Block 1030). In contrast, if the lorazepam test result is negative at Block 1032, then there is no comment at Block 1034.

Figure 28G:
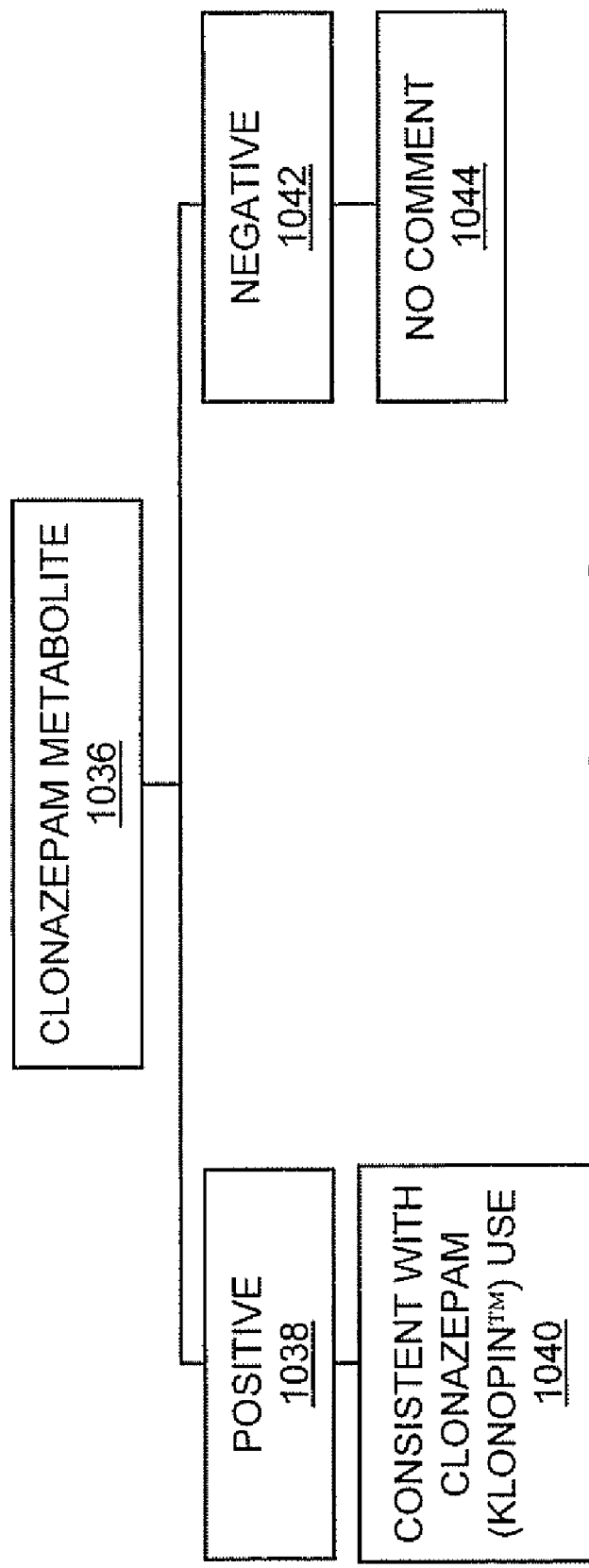

FIG. 28G illustrates a medication/drug interpretation flow chart for clonazepam 1036, in which prescription information has not been considered. A positive clonazepam test result at Block 1038 is considered consistent with clonazepam (KLONOPIN™) use (Block 1040). In contrast, if the clonazepam test result is negative at Block 1042, then there is no comment at Block 1044.

Additional examples of interpretive comments are provided in the following non-limiting examples below.

EXAMPLE 1

When Vicodin® (hydrocodone) is prescribed and both hydrocodone and hydromorphone (Dilaudid® and a metabolite of hydrocodone) are detected in the urine and the ratio of hydromorphone to hydrocodone is consistent with hydromorphone coming from hepatic metabolism of hydrocodone, then two interpretive comments are listed as follows:

| Drug Class | Result | Interpretive Comment |
|---|---|---|
| Hydrocodone | 864 ng/mL | Consistent with hydrocodone prescription |
| Hydromorphone | 214 ng/mL | Hydromorphone source from hydrocodone metabolism |

EXAMPLE 2

When an opiate/opioid is detected in the urine that is not prescribed, for example, oxycodone (Oxycontin®), and the oxymorphone to oxycodone ratio indicates that oxymorphone (Opana®) is also being used (but has not been prescribed) the interpretive comments are listed as follows:

| Drug Class | Result | Interpretive Comment |
|---|---|---|
| Oxycodone | 544 ng/mL | Discrepant result; oxycodone should be negative |
| Oxymorphone | 223 ng/mL | Oxymorphone source from oxycodone metabolism and oxymorphone use |

EXAMPLE 3

An interpretive comment will also be provided if the requisition indicates that prescription use is "unknown" or not provided. For example, if no prescription information is provided and codeine and morphine are detected in the urine and the morphine to codeine ratio indicates that morphine came from codeine metabolism, the interpretive comments would read as indicated below. Heroine is ruled out as the source of morphine since the 6-monoacetylmorphine test is negative. In addition, concentrations of codeine and morphine rule out poppy seeds as the source of morphine.

| Drug Class | Result | Interpretive Comment |
|---|---|---|
| Codeine | 327 ng/mL | Consistent with codeine use |
| Morphine | 104 ng/mL | Morphine source from codeine metabolism |

EXAMPLE 4

A comprehensive pain management panel that includes nine (9) drugs of abuse and ten (10) opioid/opiates was provided to provide the information for physicians to determine medication compliance, patient safety and mitigate practice risk. The flowcharts in FIGS. 5-28G were used to generate patient reports of consistent or discrepant results as compared with likely opioid sources. Discussions by clinical toxicology experts with practicing physicians providing pain management services to patients indicated the misinterpretation of conventional pain management opioid/opiate toxicology report data occurred frequently. The misinterpretation of opioid/opiate toxicology reports put patients and physicians at risk. The unique pain management interpretation techniques were developed to provide physicians with concise, accurate interpretive information based on published opioid/opiate pharmacologic and metabolic information, specimen analysis providing quantitative metabolite to parent drug ratios, combined with or without opiate/opioid prescription information provided by the ordering physician. The interpretations indicate the likely source of an opioid/opiate drug (s) found positive on the pain management panel, either that was prescribed or not prescribed, and whether it is consistent or discrepant with the prescribed drug (s). Prescribed drugs allegedly taken in the last three days and found to be negative on the pain management panel are flagged as discrepant. Testing for 6-monoacetylmorphine, a metabolite of heroin, on every urine specimen, in addition to codeine, morphine and a poppy seed evaluation, allows a comprehensive determination for the probable source of a positive morphine. A comprehensive interpretive evaluation of ten (10) opiate/opioids is provided. Other toxicology laboratories limit their evaluation to six (6) opiate/opioids in their common panels. In summary the Pain Management Panel interpretation methods (see, e.g., FIGS. 5-28G) are designed to save the physician time by providing a unique, concise interpretive summary based on ten urine opioid/opiate analysis results, prescribed opioid/opiates, undisclosed opioids/opiates, and opioid/opiate metabolism. The Pain Management Panel interpretive techniques indicate the likely source of opiate/opioid drugs and whether they are consistent or discrepant with the prescribed opiate/opioid drugs.

Urine Opioid-Opiate Analysis by LC/MS/MS

Principle:

The drug/medication interpretation flow charts can be based on opioid/opiate analysis performed by liquid chromatography tandem mass spectrometry (LC/MS/MS) as described below. In some embodiments, simultaneous identification and quantitation in urine of codeine, fentanyl, hydrocodone, hydromorphone, oxycodone, oxymorphone, meperidine, 6-monoacetyl morphine (6-MAM), morphine and norfentanyl as the "free" non-conjugated drug is performed by LC/MS/MS.

The analysis of the opioid-opiate drugs uses deuterium labeled internal standard analogues in batch calibrators, controls and urine aliquots. Tubes containing each urine batch specimen are placed on the MICROLAB® Hamilton Starlet liquid handling instrument from Hamilton Robotics, Reno, Nev. (USA). where 1% hydrochloric acid and internal standard are added and mixed with the urine. Solid phase extraction (SPE) columns containing sodium bisulfite are conditioned with methanol before each sample is passed through its SPE column. The columns are washed prior to the drugs and internal standard being eluted from the SPE columns with ammoniated elution solvent. After the solvent is evaporated, the residue in each tube is reconstituted with 5% acetonitrile in water. The extract is placed in autosampler vials for LC/MS/MS analysis.

An AGILENT® 6410 Triple Quadrupole LC/MS/MS from Agilent Technologies, Inc., Santa Clara, Calif. (USA) with electrospray ionization (positive ion mode) interfaced with an Agilent 1200 series binary pump SL is programmed to select and allow the positive precursor ion of each opioid-opiate drug and its respective deuterium internal standard to pass through the first quadrupole. In the second quadrupole, collision-induced dissociation (CID) is achieved to produce product ions monitored in the third quadrupole. Quantitative concentrations of the drugs are determined by calculating peak area ratios for the product ions of each drug and its deuterium internal standard.

Pharmacokinetic Information:

Opiates are pharmacologically active agents derived naturally from opium, the dried juice of the unripe seed pod of the opium poppy *Papaver somniferum*. Morphine and codeine belong to this class of natural occurring opiate alkaloids as are thebaine, noscapine and papaverine. Heroin (diacetyl-morphine) is a synthetic opiate and a more potent derivative of morphine; heroin is not legally available in the United States. Opioids are generally synthetic narcotic analgesics that have varying degrees of opiate-like pharmacological effects; some share similarity in chemical structure with morphine. The opioid drugs detected by this test method are listed alphabetically:

Codeine (Tylenol® 3, Robitussin® AC, Phenergan® VC, Many Others)

Codeine is an opiate used for its analgesic, antitussive and antidiarrheal properties. Codeine is a synthesis by-product of illicit heroin production. Codeine is naturally found in opium and opium poppy seeds used for dietary purposes. Codeine is rapidly absorbed after oral dose, with the time to peak plasma concentration estimated at one hour after ingestion. Codeine is extensively metabolized, mostly to codeine glucuronide, while 10-15% of a dose is excreted as morphine and norcodeine conjugates. Therefore codeine (free and conjugated), norcodeine, and morphine (free and conjugated) appear in urine after codeine ingestion. Morphine is not metabolized to codeine in humans. Codeine (free) is detected by LC/MS/MS for up to 3 days after it's administered. Also see the pharmacokinetic information regarding "Morphine" (below).

Fentanyl and Norfentanyl (Duragesic®, Actiq®, Fentanest®, Fentora®, Others)

Fentanyl is an opioid analgesic with a potency about 80 times that of morphine and a short duration of efficacy. Norfentanyl is a metabolite of the drug fentanyl. Fentanyl is administered by injection as an adjunct to surgical anesthesia and with the use of transdermal patches for management of chronic pain. An oral transmucosal dosage form, buccal pellets and lozenges are also available. Illicit fentanyl has been substituted for heroin sold on the black market. Fentanyl and norfentanyl are excreted in urine following fentanyl administration. Norfentanyl was detected in urine for up to 72 hours and fentanyl for less than 24 hours following a single fentanyl dose (50 to 100 ug). In chronic pain patients treated with fentanyl transdermal patches (25 to 100 ug/hr), urine fentanyl concentrations were less than 1080 ng/mL and urine norfentanyl concentrations were less than 5730 ng/mL.

Hydrocodone (Vicodin®, Hycodan®, Lortab®, Others)

Pharmacological effects of hydrocodone as an analgesic and antitussive are similar to codeine; it is available for oral administration. Hydrocodone is metabolized by the liver to hydromorphone and other metabolites. Hydrocodone can be a metabolite of codeine when codeine is used in high doses; following codeine administration the ratio of hydrocodone to codeine concentrations is less than 0.40 without another hydrocodone source. Dihydrocodeine metabolism has been shown to produce urine hydrocodone in very low concentrations. Some oxycodone pharmaceutical preparations have small amounts of hydrocodone as an impurity. An oral dose of hydrocodone may produce hydrocodone (free) for 3 days and hydromorphone for up to 4 days by LC/MS/MS analysis.

Hydromorphone (Dilaudid®)

Hydromorphone is similar to morphine but more potent and has a high abuse liability; it is available for oral, injection and suppository administration. Hydromorphone can be observed in urine as a morphine metabolite after high-dose morphine use; hydromorphone is also a metabolite of hydrocodone. About 6% of a hydromorphone dose is eliminated as free and 36% as conjugated hydromorphone. Hydromorphone use is detected as hydromorphone (free) in urine by LC/MS/MS for up to 4 days.

Oxycodone (Oxycotin®, Percodan®, Percocet®, Tylox®, Others)

Oxycodone is a semi-synthetic narcotic analgesic derived from thebaine; it is similar to but more effective than morphine when administered orally. Oxycodone is metabolized by the liver to oxymorphone and other metabolites. Within 24 hours, approximately 60% of an oral dose of oxycodone is eliminated in urine as total oxycodone and about 14% as oxymorphone. LC/MS/MS can detect oxycodone (free) for up to 3 days after an immediate release dose preparation; following a slow-release dosage form oxycodone (free) can be detected for up to 4 days.

Oxymorphone (Numorphan®, Opana®)

Oxymorphone is a semi-synthetic narcotic analgesic derived from thebaine; it is available for injection use, as a suppository (NUMORPHAN®) and as an oral preparation (OPANA®). Oxymorphone pharmaceutical material may contain 1% oxycodone as an impurity. Oxymorphone is also observed in urine as a metabolite of oxycodone use. Recent studies confirm oxymorphone is not a metabolite of morphine or hydromorphone. About 49% of an oxymorphone dose is excreted in urine, mostly as conjugated oxymorphone and a smaller amount of free oxymorphone. LC/MS/MS can detect oxymorphone (free) for up to 3 days after an immediate release dose preparation and up to 4 days following a slow-release dosage.

Meperidine (Demerol®)

Meperidine is a synthetic opioid analgesic that has pharmacological effects similar to morphine but does not emulate the general chemical structure of opiates. Excessive doses of meperidine may cause CNS excitation (tremors, seizures) largely due to the active metabolite normeperidine. Normeperidine has a longer plasma half-life than meperidine, 20 hours compared with 3 hours, but half the analgesic effect. Following a single dose of meperidine, normeperidine is usually not found in plasma but may accumulate with further administrations to exceed the parent drug concentration and contribute to toxicity.

About 7% of a dose of meperidine is eliminated as unchanged meperidine, and about 17% as normeperidine. Under conditions of acid urine, these values increase to 27% and 23%, respectively, while during alkaline conditions they decline to 0.6% and 3.6%, respectively. The detection time of meperidine in urine after administration will be greatly influenced by urine pH.

6-Monoacetylmorphine ("6-Mam")

Heroin (diacetyl morphine), an illicit opiate narcotic, is a potent analgesic with strong addiction liability. Clandestine synthesis of heroin from morphine or naturally occurring alkaloids found in opium, the dried juice of the unripe seed pod of the opium poppy *Papaver somniferum*, may produce a product having other alkaloid contaminants including small amounts of codeine. Heroin is administered intravenously or smoked. Heroin is rapidly metabolized in tissues to 6-monoacetylmorphine, and subsequently metabolized in the liver to morphine. Morphine is extensively metabolized, with only 2-12% excreted in the urine as unchanged ("free") morphine and up to 80% excreted as conjugated morphine glucuronides. Five to 14% of the morphine produced from heroin is excreted in the feces. Approximately 42% of a heroin dose is excreted as morphine-3-glucuronide over about 40 hours. Because a relatively small amount of codeine may be found in heroin as a synthesis impurity, the urine of a heroin user may contain some codeine; neither morphine nor heroin is metabolized to codeine in humans.

The presence of 6-MAM in urine is a specific marker for recent heroin use. 6-MAM is not present in urine from the use of codeine, morphine or poppy seed ingestion. After a heroin dose, 6-MAM is detected in urine for less than 3 days by LC/MS/MS. 6-MAM is stable in urine.

Morphine (MS Contin®, Roxanol®, Kadian®)

Morphine and codeine belong to the class of drugs called opiates. Other synthetic narcotic analgesics ("opioids") have some degree of opiate pharmacological effects and share some chemical structure similarity to the opiates. Both morphine and codeine are naturally occurring alkaloids from opium, the dried juice of the unripe seed pod of the opium poppy *Papaver somniferum*.

Morphine is rapidly absorbed from oral use but has low bioavailability (0.27) due to first pass metabolism. Morphine may also be smoked or administered by injection. Morphine is extensively metabolized with only 2-12% excreted in the urine as unchanged (free) morphine and up to 80% excreted as conjugated metabolites (glucuronides). A small amount (5-14%) of an administered morphine dose is excreted in the feces. The principle metabolite of morphine in urine is morphine-3-glucuronide which is excreted to the extent of 70% of the dose in 48 hours.

Heroin, after injection or smoking, is rapidly metabolized to 6-mono-acetylmorphine (6-MAM, 6-acetylmorphine) which is subsequently metabolized to morphine. Both heroin and 6-MAM disappear rapidly from the blood due to metabolism and tissue distribution, while morphine levels initially rise and then decline more slowly.

The pattern of urinary excretion of heroin is similar to that of morphine: unchanged morphine (7%) and conjugated morphine (50-60%) with only trace amounts of 6-MAM detectable in urine. The urine of a heroin user may have some codeine present because of concurrently administered codeine or because small amounts of codeine are produced in heroin illicit manufacture as a synthesis by-product.

Some varieties of poppy seeds contain varying amounts of opium resin containing concentrations of morphine and codeine approximately at a 10:1 ratio. Following ingestion, poppy seeds may cause detectable amounts of morphine and (less) codeine in the urine due to the opium resin. 6-MAM has not been found in poppy seeds or in urine after ingestion of poppy seeds.

Exemplary Testing Protocol

The following is a non-limiting, exemplary testing protocol. Although the following example is provided, it should be understood that any suitable protocol can be used. For example, different volumes of materials, solvents, types of materials, calibration standards, equipment and the like may be selected by one of skill in the art without departing from the invention.

Specimen Specifications:

Opiate-Opioid drugs are stable in urine specimens stored at ambient temperature for at least 48 hours; specimens should be refrigerated when transport to the testing laboratory is delayed. The effect of urine preservatives on this assay has not been currently determined; therefore, preservatives may be avoided pending further testing. It is acceptable to centrifuge an aliquot of urine when the specimen displays unusually high turbidity. The standard volume for this test is 30 mL of urine; 15 mL is considered a minimum acceptable volume. The Hamilton pipettes 1.0 mL of urine specimen during the extraction.

Reagents for Solid Phase Extraction:

Opioid Internal Standard

One of each vial listed below (100 ug/mL, 1 mL each from Cerilliant Corporation, Round Rock, Tex. (USA); catalog number noted below) is needed to prepare the internal standard for the opioid-opiates procedure:

| | |
|---|---|
| Fentanyl-d5 | (F-001) |
| Norfentanyl-d5 | (N-030) |
| 6-Acetylmorphine-d6 | (A-026) |
| Meperidine-d4 | (M-036) |
| Oxymorphone-d3 | (O-003) |
| Hydrocodone-d6 | (H-047) |
| Hydromorphone-d3 | (H-006) |
| Morphine-d3 | (M-003) |
| Oxycodone-d6 | (O-007) |
| Codeine-d3 | (C-005) |

Add the contents of each vial to a 1000 mL volumetric flask and add sufficient Type 1 deionized water to a final volume of 1000 mL, cap and mix well. The final concentration or each drug analogue in the internal standard is 0.1 ng/uL. Stable two years when stored refrigerated in labeled brown glass bottles.

25% Sodium Bisulfite, Saturated in 0.1M Phosphate Buffer pH 6.0:

Add 25 grams of sodium bisulfate (from Sigma, S9000; minimum 99%) to 100 mL 0.1M Phosphate Buffer, pH 6.0 prepared as described above. Mix well and store refrigerated; stable one month. Avoid direct contact and inhalation of sodium bisulfate, may cause severe irritation.

1% Hydrochloric Acid

Working in the fume hood, add 950 mL Type 1 water to a 1000 mL volumetric flask and then add 10 mL concentrated HCl and mix. Add sufficient Type 1 deionized water to a final volume of 1000 mL. Store at room temperature. Stable for 6 months. Caustic, avoid fumes and direct contact.

Ammoniated Elution Solvent (Sufficient for 40 SPE Columns Plus Dead-Space)

Prepare under the fume hood by adding 3 mL of isopropanol and 2 mL of 28%-30% ammonium hydroxide to a clean glass 50 mL volumetric flask. Mix well then add sufficient ethyl acetate to the 50 mL mark; cap and mix well. Make fresh each batch, stable one day at room temperature when tightly capped.

Detectabuse Extraction Columns 3 mL small reservoir from Biochemical Diagnostics, contains bisulfite part #GV-65C.

5% Acetonitrile in Water

With a volumetric pipette add 5 mL HPLC-Spectro grade acetonitrile from TEDIA, (#AS-1122) into a 100 mL volumetric flask. Add sufficient high purity water to a final volume of 100 mL (Use "Water, High Purity Solvent" from Burdick & Jackson Cat #365-4. Stable indefinitely when stored at room temperature.

Reagents for LC/MS/MS

NOTE: Do not wash LC/MS/MS reagent bottles using detergents and do not submit them to the dish room for cleaning. Detergents are incompatible with the analytical methods. Rinse with high purity water (e.g., from Honeywell Burdick & Jackson, Morristown, N.J. (USA) (Cat #365-4) and dry well. Ultra clean glassware for transfers of reagents into these bottles is required.

0.5% Formic Acid in 95% Water, 5% Methanol: (Solvent A, Position 1)

Use Formic Acid (98-100% from Honeywell Riedel-de Haën, Hanover, Germany, Cat #33015) and only "high purity water" (Water, High Purity Solvent from Honeywell Burdick & Jackson Cat #365-4) and "high purity methanol" (Methanol, High Purity Solvent from Burdick & Jackson Cat #230-4) for this reagent. Work under the fume hood. Add 10 mL of formic acid, 100 mL high purity methanol and 1890 mL high purity water to a clean empty 4 liter BJ-water bottle for a final volume of 2000 mL; mix well. Label the container. Stable indefinitely at room temperature.

0.5% Formic Acid in Acetonitrile: (Solvent B, Position 1)

Use Formic Acid (98-100% from Honeywell Riedel-de Haën, Cat #33015) and HPLC-Spectro grade acetonitrile from Tedia Company, Inc, Fairfield, Ohio (USA), (#AS-1122) for this reagent. Work under the fume hood. Add 20 mL of formic acid 4 liters of high purity acetonitrile for a final volume of 4000 mL; mix well. Label the container. Stable indefinitely at room temperature.

Needle Wash Solution: (50% Methanol/25% Isopropanol/25% Water)

Use Methanol-High Purity Solvent (from Burdick & Jackson Cat #230-4), Isopropanol (from Fisher Scientific, Pittsburgh, Pa. (USA) Cat # UN1219) and Water-High Purity Solvent (from Burdick & Jackson Cat #365-4) for this reagent. Work under the fume hood. Add 2000 mL of high purity methanol and 1000 mL of isopropanol and 1000 mL high purity water to a clean 4000 mL glass container to a final volume of 4000 mL and mix well. Stable indefinitely at room temperature.

Acetonitrile (Solvent A, Position 2):

Use acetonitrile mL HPLC-Spectro grade acetonitrile from Tedia, (#AS-1122). Work under the fume hood.

Water, high purity (Solvent B, Position 2):

Use only "high purity water" (Water, High Purity Solvent from Honeywell Burdick & Jackson Cat #365-4) for this reagent.

Calibrator Preparation:

1. Solution "A" Preparation (100.000 ng/mL)
  A. Weigh and then add the following neat drug standards to a 100 mL volumetric flask:
    13.3 mg Morphine sulfate pentahydrate (from Sigma, St. Louis, Mo. (USA) M-8777)
    10.0 mg Codeine (from Sigma C-5910)
    15.0 mg Hydrocodone Bitartrate (from Sigma H-4516)
    11.3 mg Hydromorphone HCl (from Sigma H-5136)
    11.2 mg Oxycodone HCl (from Sigma O-1378)
    10.0 mg Oxymorphone (from Alltech Biotechnology, Lexington, Ky. #01398)
  B. Add sufficient Type 1 water to the flask to a final volume of 100 mL. Ultrasound the volumetric flask (parafilm first) and mix well to insure complete dissolution. The concentration of each constituent drug is 100,000 ng/mL. Stable three years stored in the freezer.

2. Solution "B" Preparation (20,000 ng/mL)
  A. Combine the contents of 2 vials of Fentanyl (1.0 mg/mL. F-013 from Cerilliant) into a dram cup labeled "fentanyl". Using a 2.0 mL volumetric pipette, transfer 2.0 mL to a 100 mL volumetric flask labeled "stock". Discard the dram cup.
  B. Combine the contents of 2 vials of Norfentanyl Oxalate (1.0 mg/mL, N-031 from Cerilliant) into a dram cup labeled "norfentanyl". Using a 2.0 mL volumetric pipette, transfer 2.0 mL to the same 100 mL volumetric flask labeled "stock" prepared in step 2.A. above. Discard the norfentanyl dram cup.
  C. Combine the contents of 2 vials of 6-Acetylmorphine (1.0 mg/mL, A-009 from Cerilliant) into a dram cup labeled "6-MAM". Using a 2.0 mL volumetric pipette, transfer 2.0 mL to the same 100 mL volumetric flask labeled "stock" prepared in step 2.A. above. Discard the 6-MAM dram cup.
  D. Add 2.3 mg Meperidine HCl (from Sigma M-3142) to the same 100 mL volumetric flask labeled "stock" prepared in step 2.A. above.

D. To the flask initiated in step 2.A. above, add sufficient Type 1 water to a final volume of 100 mL. Parafilm and mix well. Transfer its contents to a labeled glass container. Final concentration 20,000 ng/mL. Stable three years stored in the freezer.

3. Opioid Calibrator 10.000 ng/mL

Volumetrically pipette 5 mL of Solution "A" and 5 mL of Solution "B" to a 50 mL volumetric flask. Add sufficient type I deionized water to a final volume of 50 mL, parafilm and mix well. Aliquot 4.5 mL into labeled tubes and freeze. Stable one year when frozen. The final concentrations of morphine, codeine, hydrocodone, oxycodone, hydromorphone and oxymorphone are 10,000 ng/mL. Note: This calibrator is not used for calibrating 6-MAM, fentanyl, meperidine and norfentanyl at 10,000 ngmL; the concentration of 6-MAM, fentanyl, meperidine and norfentanyl is 2000 ng/mL each.

4. Opioid Calibrator 2000 ng/mL

Volumetrically pipette 1 mL of Solution "A" and 5 mL of Solution "B" to a 50 mL volumetric flask. Add sufficient type I deionized water to a final volume of 50 mL, parafilm and mix well. Aliquot 4.5 mL into labeled tubes and freeze. Stable one year when frozen. The final concentration of morphine, codeine, hydrocodone, oxycodone, hydromorphone, oxymorphone, meperidine, 6-MAM, fentanyl and norfentanyl is 2000 ng/mL each.

5. Opioid Calibrator 100 ng/mL

Using a volumetric pipette add 5.0 mL of the "Opioid Calibrator 2000 ng/mL" into a 100 mL volumetric flask. Add sufficient type I deionized water to a final volume of 100 mL, parafilm and mix well. Aliquot 4.5 mL into labeled tubes and freeze. Stable one year when frozen. The final concentration of morphine, codeine, hydrocodone, oxycodone, hydromorphone, oxymorphone, meperidine, 6-MAM, fentanyl and norfentanyl is 100 ng/mL each.

6. Opioid Calibrator 50 ng/mL

Using a volumetric pipette add 25 mL of the "Opioid Calibrator 100 ng/mL" into a 50 mL volumetric flask. Add sufficient type I deionized water to a final volume of 50 mL, parafilm and mix well. Aliquot 4.5 mL into labeled tubes and freeze. Stable one year when frozen. The final concentration of morphine, codeine, hydrocodone, oxycodone, hydromorphone, oxymorphone, meperidine, 6-MAM, fentanyl and norfentanyl is 50 ng/mL each.

7. Opioid Calibrator 5 ng/mL

Using a volumetric pipette add 0.5 mL of the "Opioid Calibrator 2000 ng/mL" into a 200 mL volumetric flask. Add sufficient type I deionized water to a final volume of 200 mL, parafilm and mix well. Aliquot 4.5 mL into labeled tubes and freeze. Stable one year when frozen. The final concentration of morphine, codeine, hydrocodone, oxycodone, hydromorphone, oxymorphone, meperidine, 6-MAM, fentanyl and norfentanyl is 5 ng/mL each.

8. Opioid Calibrator 2.5 ng/mL

Using a volumetric pipette add 25 mL of the "Opioid Calibrator 5 ng/mL" into a 50 mL volumetric flask. Add sufficient type I deionized water to a final volume of 50 mL, parafilm and mix well. Aliquot 4.5 mL into labeled tubes and freeze. Stable one year when frozen. The final concentration of morphine, codeine, hydrocodone, oxycodone, hydromorphone, oxymorphone, meperidine, 6-MAM, fentanyl and norfentanyl is 2.5 ng/mL each.

9. Opioid Calibrator 1.0 ng/mL

Using a volumetric pipette add 10 mL of the "Opioid Calibrator 5 ng/mL" into a 50 mL volumetric flask. Add sufficient type I deionized water to a final volume of 50 mL, parafilm and mix well. Aliquot 4.5 mL into labeled tubes and freeze. Stable one year when frozen. The final concentration of morphine, codeine, hydrocodone, oxycodone, hydromorphone, oxymorphone, meperidine, 6-MAM, fentanyl and norfentanyl is 1.0 ng/mL each.

Quality Control Specimens:

Quality control mean values and range limits can be established prior to the use of the following materials.

Near Control (+25%)

A 1:10 dilution of the laboratory's "High Control" (Detectabuse Custom Liquid Control from Biochemical Diagnostics) is used. Using a volumetric pipette add 5.0 mL of the High Control urine into a 50 mL volumetric flask. Add sufficient certified negative urine to a final volume of 50 mL, parafilm and mix well. The target concentration is 6.3 ng/mL for morphine, codeine, hydrocodone, oxycodone, hydromorphone, oxymorphone, meperidine and 6-MAM; the target concentration is 2.5 ng/mL for fentanyl and norfentanyl. See current quality control chart for validated mean, range, lot and expiration date of each drug or drug metabolite. The control is stable for one month when refrigerated.

High Control (×10)

Use Detectabuse Custom Liquid Control from Biochemical Diagnostics without further dilution. The target concentration is 62.5 ng/mL for morphine, codeine, hydrocodone, oxycodone, hydromorphone, oxymorphone, meperidine and 6-MAM; the target concentration is 25 ng/mL for fentanyl and norfentanyl. See current quality control chart for validated mean, range, lot and expiration date of each drug or drug metabolite. The control is stored frozen until expiration date listed on the label. Once thawed, the control is stable for one month when refrigerated.

Negative Control

Use the current lot of lab-made certified negative urine.

Sample Extraction Using the Hamilton MICROLAB® Starlet:

The Hamilton MICROLAB® Starlet instrument is a robotic workstation that provides automated liquid handling functions including gravity-flow solid phase extraction of urine specimens. The Hamilton MICROLAB® Starlet aspirates and dispenses the sample and reagents using monitored air displacement quantitative pipette technologies with disposable pipette tips, liquid level sensing and barcode specimen accession number tracking. The sample extracts are subsequently tested using LC/MS/MS analysis.

General Outline (Overview)—Hamilton Extraction Procedure:

Each batch specimen aliquot tube and two empty tubes, each with matching barcodes, are manually placed on the instrument.

Barcode scanning of each batch specimen aliquot tube is performed; proper placement of the two empty tubes relative to their sample tube is verified by barcode scanning.

1.0 mL of HCl and 0.5 mL of Opioid Internal Standard are pipetted into the first empty tube, the "reation" tube.

Pipette 1.0 mL of specimen into the reaction tube and mix.

Solid phase extraction columns (SPE) initially condition with 1.0 mL methanol and 1.0 mL of 25% sodium bisulfite (drain by gravity) are transferred to the Hamilton to be conditioned twice with 1.0 mL methanol. Drain for 120 seconds.

2.0 mL of acidified sample with internal standard is applied to the conditioned SPE column. Drain for 300 seconds.

SPE column is washed with 1.0 mL type I deionized water, followed by 1.0 mL methanol and then 1.0 mL ethyl acetate. Drain for 120 seconds; the wash is sent to waste.

SPE column is eluted with 1.0 mL Elution Solvent into the second barcode labeled tube, the "elution" tube.

Procedure—Specimen Extraction

A urine sample is partially purified by applying the sample to a cation exchange column, washing the column with an aqueous solution, and then eluting the partially purified sample from the column with an ammoniated organic solvent.

LC/MS/MS Method

The following are exemplary conditions for liquid chromatography and mass spectrometry according to some embodiments of the present invention.

Liquid Chromatography:

| | |
|---|---|
| HPLC: | Agilent 1200 series binary pump SL, thermostatted column |
| Column: | Zorbax Eclipse XDB-C18 Rapid Resolution HT 2.1 × 100 mm 1.8 Micron 600 Bar (from Agilent Technologies PN: 928700-902). |
| Injection Vol: | 4.0 uL |
| Autosampter Temp. | Ambient |
| Needle Wash: | flushport (50% methanol: 25% isopropanol: 25% water), 15 seconds. |
| Mobile Phase: | A = 0.5% formic acid in 5% methanol: 95% water |
| | B = 0.5% formic acid in acetonitrile |
| Gradient Flow: | 0.4 mL/min |
| Gradient: | Time (min) / % B |
| | 0.0 / 0 |
| | 3.5 / 10 |
| | 6.5 / 95 |
| Stop time: | 8.0 min |
| Post time: | 3.0 min |
| Total run: | 11.0 minutes (includes regeneration time) |

Mass Spectrometer Agilent 6410A Triple Quadrupole LC/MS/MS

| | |
|---|---|
| Conditions: | Electrospray ionization (ESI), positive |
| ESI Source conditions: | |
| Gas temperature | 350° C. |
| Drying gas ($N_2$) | 10 L/min |
| Nebulizer gas ($N_2$) | 35 psi |
| Capillary voltage | 4000 V |
| MRM acquisition | peak width 0.7 amu (Q1 and Q2) |
| EM Voltage | 600 V over autotune (time segment 2 & 3) |
| | 250 V over autotune (time segment 4) |

The following table illustrates exemplary LC/MS/MS acquisition parameters.

| Compound Name | Time Segment | Precursor Ion | Product Ion* | Dwell | Frag (V) | CE (V) |
|---|---|---|---|---|---|---|
| Oxymorphone-d3 | 2 | 305.2 | 245.1 | 50 | 110 | 30 |
| Oxymorphone-d3 | 2 | 305.2 | 230.1* | 50 | 110 | 33 |
| Oxymorphone | 2 | 302.2 | 227.1* | 50 | 110 | 33 |
| Oxymorphone | 2 | 302.2 | 198.1 | 50 | 110 | 55 |
| Hydromorphone-d3 | 2 | 289.2 | 157.1 | 50 | 110 | 50 |
| Morphine-d3 | 2 | 289.2 | 152.1 | 50 | 110 | 75 |
| Hydromorphone-d3 | 2 | 289.2 | 128.1* | 50 | 110 | 75 |
| Morphine-d3 | 2 | 289.2 | 128.1* | 50 | 110 | 75 |
| Hydromorphone | 2 | 286.2 | 185.0* | 50 | 110 | 33 |
| Hydromorphone | 2 | 286.2 | 157.0 | 50 | 110 | 50 |
| Morphine | 2 | 286.2 | 152.1 | 50 | 110 | 75 |
| Morphine | 2 | 286.2 | 128.0* | 50 | 110 | 73 |
| 6-MAM-d6 | 3 | 334.2 | 191.3 | 40 | 110 | 30 |
| 6-MAM-d6 | 3 | 334.2 | 165.1* | 40 | 110 | 40 |
| 6-MAM | 3 | 328.2 | 211.0 | 40 | 110 | 27 |
| 6-MAM | 3 | 328.2 | 165.1* | 40 | 110 | 40 |
| Oxycodone-d6 | 3 | 322.2 | 262.1 | 40 | 110 | 30 |
| Oxycodone-d6 | 3 | 322.2 | 247.1* | 40 | 110 | 30 |
| Oxycodone | 3 | 316.2 | 256.0 | 40 | 110 | 27 |
| Oxycodone | 3 | 316.2 | 241.1* | 40 | 110 | 30 |
| Hydrocodone-d6 | 3 | 306.2 | 246.1 | 40 | 110 | 28 |
| Hydrocodone-d6 | 3 | 306.2 | 202.1* | 40 | 110 | 28 |
| Codeine-d3 | 3 | 303.2 | 152.0* | 40 | 110 | 75 |
| Codeine-d3 | 3 | 303.2 | 115.1 | 40 | 110 | 85 |
| Hydrocodone | 3 | 300.2 | 199.0* | 40 | 110 | 28 |
| Codeine | 3 | 300.2 | 152.0* | 40 | 110 | 75 |
| Hydrocodone | 3 | 300.2 | 128.0 | 40 | 110 | 73 |
| Codeine | 3 | 300.2 | 115.0 | 40 | 110 | 85 |
| Fentanyl-d5 | 4 | 342.2 | 188.2* | 50 | 140 | 25 |
| Fentanyl-d5 | 4 | 342.2 | 105.1 | 50 | 140 | 50 |
| Fentanyl | 4 | 337.2 | 188.2 | 50 | 140 | 25 |
| Fentanyl | 4 | 337.2 | 105.1* | 50 | 140 | 45 |
| Meperidine-d4 | 4 | 252.2 | 224.2* | 50 | 140 | 20 |
| Meperidine-d4 | 4 | 252.2 | 178.1 | 50 | 140 | 20 |
| Meperidine | 4 | 248.2 | 220.0* | 50 | 140 | 20 |
| Meperidine | 4 | 248.2 | 174.1 | 50 | 140 | 20 |
| Norfentanyl-d5 | 4 | 238.2 | 155.1 | 50 | 110 | 15 |
| Norfentanyl-d5 | 4 | 238.2 | 84.0* | 50 | 110 | 16 |
| Norfentanyl | 4 | 233.2 | 84.0* | 50 | 110 | 16 |
| Norfentanyl | 4 | 233.2 | 55.0 | 50 | 110 | 43 |

*Denotes quantitative product ion from Multiple Reaction Monitoring (MRM).

NOTE: When nitrogen supply is OFF for less than 3 hours, set the unit to standby conditions. An error prompt will occur but will clear when the nitrogen is restored. When the nitrogen is off longer than 3 hours, vent the system and turn the instrument off to prevent the vacuum from pulling room air into the instrument.

Although embodiments according to the present invention are described herein with respect to urine samples, it should be understood that other body fluids can be used, including blood, serum, plasma, saliva, perspiration, meconium, and/or homogenized cord tissue. Although embodiments according to the present invention are described herein as identifying and interpreting drug tests when prescription information is known or unknown in a clinical setting, it should be understood that embodiments according to the present invention can be used in a forensic setting, a work-place or school drug testing setting, or other suitable areas.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A method for assessing patient compliance with opioid drug therapy, the method comprising:
    simultaneously detecting a set of measurements including an amount of at least ten opioids in a body fluids sample from a patient using a liquid chromatography tandem mass spectrometer (LC/MS/MS), wherein the set of at least ten opioids includes at least oxymorphone and fentanyl; and generating a report of patient compliance based on the set of measurements;

wherein the report of patient compliance comprises ratios of concentrations of opioids and their respective metabolites.

2. The method of Claim 1, further comprising determining a set of discrepant and/or consistent results for a plurality of opioids based on a comparison of the set of measurements with data relating to prescription information for the patient.

3. The method of Claim 1, wherein the discrepant and consistent results indicate whether a patient is taking opioids being prescribed and/or taking additional drug.

4. The method of claim 1, wherein the set of measurements includes detected threshold amounts of each of said opioids below 10 ng/ml in said sample.

5. A method for assessing patient compliance with opioid drug therapy, the method comprising:

simultaneously detecting a set of measurements including an amount of at least ten opioids in a body fluids sample from a patient using a liquid chromatography tandem mass spectrometer (LC/MS/MS), wherein the set of at least ten opioids includes at least oxymorphone and fentanyl; and generating a report of patient compliance based on the set of measurements wherein the set of measurements includes detected threshold amounts of fentanyl and nor-fentanyl as low as 2 ng/ml and detected threshold amounts of oxymorphone, morphine, hydrocodone, hydromorphone, oxycodone, codeine, 6-monoacetylmorphine and meperidine as low as 5 ng/ml in said sample.

6. A method for assessing patient compliance with opioid drug therapy, the method comprising:

simultaneously detecting a set of measurements including an amount of at least ten opioids in a body fluids sample from a patient using a liquid chromatography tandem mass spectrometer (LC/MS/MS), wherein the set of at least ten opioids includes at least oxymorphone and fentanyl; and generating a report of patient compliance based on the set of measurements;

wherein the set of at least ten opioids includes hydrocodone, hydromorphone, oxycodone, oxymorphone, codeine, morphine, 6-monoacetylmorphine, meperidine, fentanyl and nor-fentanyl.

7. The method of claim 1, wherein the set of measurements further includes a detected absence or presence of one or more drugs of abuse.

8. The method of claim 7, wherein the drugs of abuse include alcohol, amphetamines, barbiturates, benzodiazepines, cocaine, marijuana, methadone, phencyclidine and/or propoxyphene.

9. A method for assessing patient compliance with opioid drug therapy, the method comprising:

simultaneously detecting a set of measurements including an amount of at least ten opioids in a body fluids sample from a patient using a liquid chromatography tandem mass spectrometer (LC/MS/MS), wherein the set of at least ten opioids includes at least oxymorphone and fentanyl; and generating a report of patient compliance based on the set of measurements., wherein generating the report of patient compliance comprises, if the set of measurements indicates a ratio of oxymorphone to oxycodone of greater than 20-30%, generating a notice indicating an oxymorphone source from oxycodone metabolism and/or oxymorphone use.

10. A method for assessing patient compliance with opioid drug therapy, the method comprising:

simultaneously detecting a set of measurements including an amount of at least ten opioids in a body fluids sample from a patient using a liquid chromatography tandem mass spectrometer (LC/MS/MS), wherein the set of at least ten opioids includes at least oxymorphone and fentanyl; and generating a report of patient compliance based on the set of measurements;

wherein generating the report of patient compliance comprises, if the set of measurements indicates a ratio of oxymorphone to oxycodone of less than 20-30%, generating a notice indicating an oxymorphone source from oxycodone metabolism.

11. The method of claim 9, wherein generating the report of patient compliance comprises comparing the oxymorphone source with prescription information indicating whether the patient is prescribed the indicated oxymorphone source, and determining if the patient is compliant or non-compliant based on the comparison.

12. A method for assessing patient compliance with opioid drug therapy, the method comprising:

simultaneously detecting a set of measurements including an amount of at least ten opioids in a body fluids sample from a patient using a liquid chromatography tandem mass spectrometer (LC/MS/MS), wherein the set of at least ten opioids includes at least oxymorphone and fentanyl; and generating a report of patient compliance based on the set of measurements;

further comprising partially purifying the sample using gravity flow solid phase extraction before simultaneously detecting a set of measurements using an LC/MS/MS.

13. The method of claim 12, wherein the steps of partially purifying the sample and simultaneously detecting are performed using an automated robotic workstation.

14. The method of claim 12, wherein the step of partially purifying the sample comprises partially purifying the sample by a process comprising applying a body fluid sample to a cation exchange column, washing the column with an aqueous wash solution, and then eluting the partially purified body fluid sample from the column with an ammoniated organic solvent.

15. The method of claim 1, wherein the body fluid is selected from the group consisting of urine, blood, serum, plasma, saliva, perspiration, meconium, and/or homogenized cord tissue.

16. The method of claim 1, one of the at least ten opioids comprises morphine and codeine, and generating a report of patient compliance further comprising:

detecting a negative or positive 6-monoacetylmorphine result as part of the set of measurements;

if 6-monoacetylmorphine is detected and a concentration of codeine is negative, generating a notice indicating a morphine source consistent with heroin use;

if 6-monoacetylmorphine is not detected and a concentration of codeine is negative, generating a notice indicating a morphine source consistent with morphine use;

if 6-monoacetylmorphine is not detected, a concentration of codeine is detected, and a morphine/codeine ratio is less than 55%, generating a notice indicating a morphine source from codeine metabolism;
if 6-monoacetylmorphine is not detected, a concentration of codeine is detected, and a morphine/codeine ratio is greater than 55%, generating a notice indicating a morphine source from codeine metabolism and morphine use; and
if 6-monoacetylmorphine is detected and a concentration of codeine is detected, generating a notice indicating a morphine source from heroin use and codeine metabolism to morphine.

17. The method of claim 1, wherein the set of at least ten opioids includes hydrocodone and codeine, and generating a report further comprises:
if a ratio of hydrocodone to codeine is less than 40%, generating a notice that the hydrocodone source is likely from hydrocodone use and/or high dose codeine metabolism to hydrocodone;
if a ratio of hydrocodone to codeine is greater than 40%, generating a notice that the hydrocodone source is likely from high dose codeine metabolism to hydrocodone and/or hydrocodone use; and
if hydrocodone is detected and codeine is not detected, generating a notice that the hydrocodone source is consistent with hydrocodone use.

18. The method of claim 1, wherein the set of at least ten opioids includes hydromorphone and morphine, and generating a report further comprises:
if a ratio of hydromorphone to morphine is less than 25%, generating a notice that the hydromorphone source is from morphine and/or hydromorphone use; and
if a ratio of hydromorphone to morphine is greater than 25%, generating a notice that the hydromorphone source is from high dose morphine metabolism and/or hydromorphone use.

19. The method of claim 18, wherein the set of at least ten opioids includes hydrocodone, and generating a report further comprises:
if a ratio of hydromorphone to morphine is greater than 25% and a ratio of hydromorphone to hydrocodone is greater than 30%, generating a notice that the hydromorphone source is from hydrocodone metabolism and/or hydromorphone use;
if a ratio of hydromorphone to morphine is greater than 25% and a ratio of hydromorphone to hydrocodone is less than 30%, generating a notice that the hydromorphone source is from hydrocodone metabolism;
if a ratio of hydromorphone to morphine is less than 25% and a ratio of hydromorphone to hydrocodone is greater than 30%, generating a notice that the hydromorphone source is from hydrocodone metabolism and/or hydromorphone use; and
if a ratio of hydromorphone to morphine is less than 25% and a ratio of hydromorphone to hydrocodone is less than 30%, generating a notice that the hydromorphone source is from hydrocodone metabolism and/or high does morphine metabolism.

20. The method of claim 1, one of the at least ten opioids comprises morphine and codeine, and generating a report of patient compliance further comprising:
if a morphine/codeine ratio is less than 55%, generating a notice indicating a morphine source from codeine metabolism; and
if a morphine/codeine ratio is greater than 55%, generating a notice indicating a morphine source from codeine metabolism and morphine use.

21. The method of claim 15, further comprising comparing an indication of opioid source to prescription information to determine if a patient is compliant.

22. A system for assessing patient compliance with opioid drug therapy, the system comprising:
a liquid chromatography tandem mass spectrometer (LC/MS/MS) configured to simultaneously detect a set of measurements including an amount of at least ten opioids (and their metabolites) in a body fluids sample from a patient, wherein the set of at least ten opioids includes at least oxymorphone and fentanyl; and
a module configured to generate a report of patient compliance based on the set of measurements;
wherein the report of patient compliance comprises ratios of concentrations of opioids and their respective metabolites.

23. The system of Claim 22, wherein a set of discrepant and/or non-discrepant results for a plurality of opioids is determined by comparing the set of measurements with data relating to prescription information for the patient.

24. The system of claim 23, wherein the discrepant and consistent results indicate whether a patient is taking opioids being prescribed and/or taking additional drug.

25. The system of claim 22, wherein the set of measurements includes detected threshold amounts of each of said opioids below 10 ng/ml in said sample.

26. A system for assessing patient compliance with opioid drug therapy, the system comprising:
a liquid chromatography tandem mass spectrometer (LC/MS/MS) configured to simultaneously detect a set of measurements including an amount of at least ten opioids (and their metabolites) in a body fluids sample from a patient, wherein the set of at least ten opioids includes at least oxymorphone and fentanyl; and
a module configured to generate a report of patient compliance based on the set of measurements;
wherein the set of measurements includes detected threshold amounts of fentanyl and nor-fentanyl as low as 2 ng/ml and detected threshold amounts of oxymorphone, morphine, hydrocodone, hydromorphone, oxycodone, codeine, 6-monoacetylmorphine and meperidine as low as 5 ng/ml in said sample.

27. A system for assessing patient compliance with opioid drug therapy, the system comprising:
a liquid chromatography tandem mass spectrometer (LC/MS/MS) configured to simultaneously detect a set of measurements including an amount of at least ten opioids (and their metabolites) in a body fluids sample from a patient, wherein the set of at least ten opioids includes at least oxymorphone and fentanyl; and
a module configured to generate a report of patient compliance based on the set of measurements;
wherein the set of at least ten opioids includes hydrocodone, hydromorphone, oxycodone, oxymorphone, codeine, morphine, 6-monoacetylmorphine, meperidine, fentanyl and nor-fentanyl.

28. The system of claim 22, wherein the set of measurements further includes a detected absense or presence of one or more drugs of abuse.

29. The system of claim 28, wherein the drugs of abuse include alcohol, amphetamines, barbiturates, benzodiazepines, cocaine, marijuana, methadone, phencyclidine and/or propoxyphene.

30. A system for assessing patient compliance with opioid drug therapy, the system comprising:
a liquid chromatography tandem mass spectrometer (LC/MS/MS) configured to simultaneously detect a set of measurements including an amount of at least ten opioids (and their metabolites) in a body fluids sample from a patient, wherein the set of at least ten opioids includes at least oxymorphone and fentanyl; and a module configured to generate a report of patient compliance based on the set of measurements;

wherein if the set of measurements indicates a ratio of oxymorphone to oxycodone of greater than 20-30%, the module is configured to generate the report of patient compliance to include a notice indicating an oxymorphone source from oxycodone metabolism and/or oxymorphone use.

31. A system for assessing patient compliance with opioid drug therapy, the system comprising:

a liquid chromatography tandem mass spectrometer (LC/MS/MS) configured to simultaneously detect a set of measurements including an amount of at least ten opioids (and their metabolites) in a body fluids sample from a patient, wherein the set of at least ten opioids includes at least oxymorphone and fentanyl; and a module configured to generate a report of patient compliance based on the set of measurements;

wherein if the set of measurements indicates a ratio of oxymorphone to oxycodone of less than 20-30%, the module is configured to generate the report of patient compliance to include a notice indicating an oxymorphone source from oxycodone metabolism.

32. The system of claim 30, wherein the module is further configured to generate the report of patient compliance by comparing the oxymorphone source with prescription information indicating whether the patient is prescribed the indicated oxymorphone source, and determining if the patient is compliant or non-compliant based on the comparison.

33. A method for assessing opioid drug source, the method comprising:

simultaneously detecting a set of measurements including an amount of at least ten opioids in a body fluids sample from a subject using a liquid chromatography tandem mass spectrometer (LC/MS/MS), wherein the set of at least ten opioids includes at least oxymorphone and fentanyl; and generating a report of potential opioid source(s) based on the set of measurements;

wherein the report of potential opioid source(s) comprises ratios of concentrations of opioids and their respective metabolites.

34. The method of claim 33, wherein the simultaneously detecting is performed before prescribing an opioid to a subject.

35. The method of claim 33, wherein generating a report comprises assessing patient compliance with known prescription information.

36. The method of claim 33, wherein the sample comprises a forensic sample.

37. The method of Claim 33, further comprising identifying the potential opioid source(s) using the ratios of concentrations of opioids and their respective metabolites.

38. A system for assessing patient compliance with opioid drug therapy, the system comprising:

a liquid chromatography tandem mass spectrometer (LC/MS/MS) configured to simultaneously detect a set of measurements including an amount of a plurality of opioids (and their metabolites) in a body fluids sample from a patient, wherein the plurality of opioids includes at least oxymorphone and fentanyl and the body fluids sample is provided with machine-readable codes configured to identify prescription information corresponding to the patient;

a report generation module in communication with the LC/MS/MS;

a prescription reader in communication with the report generation module, wherein the prescription reader is configured to automatically receive the machine-readable codes and to input the codes to the report generation module, wherein the report generation module is configured to generate a report of patient compliance based on the set of measurements and the prescription information provided by the machine-readable codes.

39. The system of claim 38, wherein the codes are barcodes.

* * * * *

UNITED STATES PATENT AND TRADEMARK OFFICE
CERTIFICATE OF CORRECTION

PATENT NO. : 8,067,243 B2  Page 1 of 1
APPLICATION NO. : 12/552596
DATED : November 29, 2011
INVENTOR(S) : Erfurth et al.

It is certified that error appears in the above-identified patent and that said Letters Patent is hereby corrected as shown below:

Column 11, Line 3: Please correct "FIGS 5A and 8B" to read -- FIGS 8A and 8B --

Column 27, Line 6: Please correct "Calibrator 10.000 ng/mL"
to read -- Calibrator 10,000 ng/mL --

Column 31, Claim 5, Line 30: Please correct "of measurements"
to read -- of measurements; --

Signed and Sealed this
Twenty-ninth Day of May, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,067,243 B2 | Page 1 of 1 |
| APPLICATION NO. | : 12/552596 | |
| DATED | : November 29, 2011 | |
| INVENTOR(S) | : Erfurth et al. | |

It is certified that error appears in the above-identified patent and that said Letters Patent is hereby corrected as shown below:

Column 31, Claim 9, Line 67: Please correct "of measurements.,"
to read -- of measurements; --

Signed and Sealed this
Eighteenth Day of September, 2012

David J. Kappos
*Director of the United States Patent and Trademark Office*